US006855866B1

(12) United States Patent
Weterings et al.

(10) Patent No.: US 6,855,866 B1
(45) Date of Patent: Feb. 15, 2005

(54) POLYNUCLEOTIDES USEFUL FOR MODULATING TRANSCRIPTION

(75) Inventors: Koen Weterings, Nijmegen (NL); Nestor R. Apuya, Culver City, CA (US); Robert B. Goldberg, Topanga, CA (US)

(73) Assignee: The Regents of the University of California, Oakland, CA (US)

( * ) Notice: Subject to any disclaimer, the term of this patent is extended or adjusted under 35 U.S.C. 154(b) by 231 days.

(21) Appl. No.: 09/724,857

(22) Filed: Nov. 28, 2000

(51) Int. Cl.[7] .............................. C12N 15/82; A01H 5/00
(52) U.S. Cl. ..................... 800/287; 800/298; 435/320.1; 435/419; 435/468; 424/93.2; 536/24.1
(58) Field of Search .............................. 435/320.1, 419, 435/468; 536/24.1, 23.6; 800/287, 298; 424/93.2

(56) References Cited

U.S. PATENT DOCUMENTS 6,114,605 A * 9/2000 Williamson et al. ..... 800/317.4
6,262,343 B1 * 7/2001 Staskawicz et al. ........ 800/279

OTHER PUBLICATIONS

Kim et al. A 20 nucleotide upstream element is essential for the nopaline synthase (nos) promoter activity. (Plant Molecular Biology, 1994, vol. 24, pp. 105–117).*

McDonald et al. Mutation of either G box or I box sequences profoundly affects expression from the Arabidopsis rbcS–1A promoter.(1990, EMBO Journal, vol. 9, pp. 1717–1726).*

Weterings, Koen: "Regional Localization of Suspensor mRNAs during Early Embryo Development": *The Plant Cell*: Nov. 2001; pp. 2409–2425; vol. 13.

* cited by examiner

*Primary Examiner*—David T. Fox
*Assistant Examiner*—Cynthia Collins
(74) *Attorney, Agent, or Firm*—Townsend and Townsend and Crew LLP

(57) ABSTRACT

The invention provides polynucleotides for expression of genes in suspensor cells in plants and methods for using such polynucleotides.

13 Claims, 21 Drawing Sheets

SCHEMATIC OF A GENE

FIG. 2

```
-4242  GCATGCACTG CCACAAGTAG TGAACTCATG GTTTTACCTC CTCAAGTAGA
-4192  AAACCTTTTG AGTGAATTTG AAGATTTATT CTCCCAAGAA GGACCCATTG
-4142  GGCTTCCTCC TCTTAGGGGG ATAGAACATC AAATTGACTT TATACCGGGG
-4092  GCAAGCCTAC CAAATAGGCC TCCTTATAGA ACCAACCCCG AGGAAACAAA
-4042  GGAGATAGAA TCACAAGTTC AAGACTTGTT GGAGAAGGGT TGGGTTCAAA
-3992  AGAGCCTAAG CCCTTGTGCT GTACCTGTCT TGTTGGTGCC AAAAAAAGAT
-3942  GGAAAATGGC GTATGTGTTG TGATTGTAGA GCAATCAACA ACATCACCAT
-3892  CAAGTATAGG CATCCAATCC CAAGGCTTGA CGATATGCTT GATGAATTGC
-3842  ATGGGTCAAC TCTATTCTCC AAAATTGACC TTAAAAGTGG ATATCACCAA
-3792  ATTCGAATCA AGGAGGGTGA TGAGTGGAAA ACCGCTTTTA AGACCAAATT
-3742  TGGATTATAT GAGTGGTTGG TGATGCCCTT TGGTCTTACT AACGCTCCAA
-3692  GTACATTCAT GAGGCTTATG AATCACACCT TGAGGGATTG TATAGGTAAA
-3642  TATGTAGTAG TTTATTTTGA TGATATCTTA GTATATAGTA AAACCCTAGA
-3592  AGACCATCTA AGTCACCTTA GGGAAGTTCT TCTAGTTCTT AGGAAAAATA
-3542  GTCTTTTTGC CAATAGGGAT AAGTGTACCT TTTGTGTAGA TAGCGTAGTC
-3492  TTTTTAGGCT TTATAGTAAA CCAAAAGGGG GTGCATGTAG ATCCCGAGAA
-3442  AATCAAAGCC ATCCGCGAGT GGCCAACTCC ACAAAATGTA AGTGATGTGA
-3392  GAAGTTTTCA TGGGTTAGCT AGCTTCTATA GAAGGTTTGT TCCCAATTTT
-3342  TCTAGCCTAG CTTCTCCCTT GAATGAACTT GTAAAAAAG ATGTTGCATT
-3292  TTGTTGGAAT GAAAAGCATG AGCAAGCCTT TCAAAGGCTA AAAGCTCACT
-3242  CACCAATGCA CCCATCCTAT CTCTTCCAAA TTTTTCCAAA CTTTTGGAGA
-3192  TAGAGTGTGA TGCATCGGGA GTAGGCATAG TGCGGTTTTG TTGCAAGGTG
-3142  GACACCCCTT GCTTATTTTA GTGAAAAACT CCATGGTGCC ACCCTCACTA
-3092  CCCCACCTAT GACAAAGACT CTATGCTCTT GTGCGACCCT AAAGACTTGG
-3042  GGAACACTAC CTTGnGTCCC AAAGAATTTG GnTATCCATA GTGATCACGA
-2992  GTCTTTAAAA TATTTAAAGG GCCAACACAA GCTCAATAAG AGACATGCTA
-2942  AATGGATGGA ATTTCTTGAA CAATTTCCTT ATGTCATCAA ATACAAGAAA
-2892  GGGAGCACCA ATATAGTGGC CGATGCTCTT TCTAGACGGC ACACTCTCTT
-2842  TTCAAAACTA GGTGCCCAAA TTCTTGGATT TGACCACATA AGAGAGCTTT
-2792  ATCAAGAAGA TCAAGAACTC TCATCCATCT ATGCCCAATG TCTACATAGA
-2742  GCACAAGGAG GTTACTATGT GTCCGAGGGA TATCTTTTTA AAGAAGGAAA
-2692  ACTTTGCATT CCCCAAGGAA CACATAGAAA ACTCCTTGTC AAAGAATCAC
-2642  ATGAAGGGGG ACTCATGGGC CATTTTGGAG TTGATAAAAC TCTAGACTTT
-2592  TAAAAGCAAA ATTTTGTTGG CCACACATGA GGAAAGATGT CCACGACATT
-2542  GTCTAGAGTA TCTCATGTTT AAAAGCAAAG TCTAGAACAA TGCCGCTGGA
-2492  CTCTACACCC CTTTGCCGAT TGCAAAGCTC CTTGTGAAGA CATTAGCATG
-2442  GATTTCATTT TAGGACTTCC TAGGACTGCA AGAGGCCATG ACTCTATCTT
-2392  TGTGGTAGTG GACCGTTTTA GCAAAATGTC TCACTTTATT CCATGCCACA
-2342  AAGTAGATGA TGCTCAAAAT ATTTCTAAAC TCTTCTTTAG AGAAGTGGTG
-2292  AGACTCCATG GTCTCCCTAG AAGTATAGTG TCCGATAGAG ATCACCTTAA
-2242  ATATATAATT ATACACTTGT TTTTTTTCTC TTTTTTATTT TATCAAGTAA
-2192  AAAGTATTTG TTCTAGATTA TTATGAGTAT ATACTTACTT TCTGTATTTC
-2142  ATTTCTTTCT ATTTTTTATG ACGATGAAAT TCTTATTAT ATCCAGACTT
-2092  TTCATATATA TTTTTATTTC TTTTCCATCT AGATGCTCTG TACTTTTCTT
-2042  CAGTTGAAAT TTCCACTCTC CAACAAAACA TCATTCAAGT TTTGTATAAC
-1992  ACTGTGACGT TAACCAGTTA AAATAAGAAA ATCATGTAAT ATAAATTATT
-1942  TCAGTAGATA TTTTAGAATT ACAAATACGA TAAATAATTA AATTTAAAAA
-1892  ATTATTAAAC AATGAATTTT TTTGGAAATT AATATAAAAC TTAGACTTGT
```

FIG. 2 (Continued)

```
-1792  ACATCGAATT TGGGTGCTTT ATGCCGCTTT ATCTTCATCT GCACCTTCAA
-1742  ATTAATAATT TAATTCCGGA AAATAATAAA CCCACACACT GTTTTATGCA
-1692  TATATTAAGA TAAATAAAAG AGAACTATTT TAAAGAATAT AAAATAATAA
-1642  ATGTAACAAA TGATGTCACT AAAGAAGAAA AAAATTAACA AGAATTGTAA
-1592  TATATTTCTT TATGAAATGT TTTGTGCATT ACCGAGAGAG GTCGAACATG
-1542  ATACACGCAA GCATCTAACT AGTTTGGTAA TTCCTTTTCA ACATCGnTAA
-1492  GCACATCACA CTAAAATTAC TTTAAATAGA TAAATTAGAT TCAATTGGAT
-1442  GACATTAATT TATAATACTC TATCCAAAAT TATAACTATA AATAAAAAGT
-1392  TATTTTTAGA AAATAAGTAA TGAAAATTTA ATTCTAAAAT TTATAACACT
-1342  TTTATGCTGT GTTTGTTTCG AAGCATAGAA AAATAAAAAG TTATTGTTGG
-1292  GAATGAAAAG TGAAGAAAAT CATGTAATAA AAACAAAATG ACACGACAAT
-1242  CAAAAAAAAA GTTTTCATGC AAAACTTTTT TCAAAATTTA CACTTTTATG
-1192  ATGTGTTTGT TTCGAAGTGT AGAAAAACGA AAAGTTATTA TTGGTAATGA
-1142  AAAGCGAAGA AAATCACGTA ATAAAAACAA AGCAAGATGG CACGACAATC
-1092  AAAAAAAAGT TTCTACACAA AACTTTATTC AAAATTTACA ACACTTTTAT
-1042  GTTGTTGTTT GTTTCCGAGG TATAGAAAAA CAAAGAATTA GTGTTGGTAA
 -992  TGAAAAGTGA AGAAAACCAT GTAATGAAAA CAAAATGGCA CGACAATCAA
 -942  AAAAAGTTTT CACGCAAAAT TTCTTCAAA ATTTATAACA TTTTCATGTT
 -892  GTGTTTGTTT CAAAGCCTAG AAAAACGAAG AGTTACTATT GGTAATGAAA
 -842  AGCGAAGAAA ACCACATAAT AAAAACAAAA TGGCACGACA ATCAAGAAAA
 -792  AGTTTTCACA CAAAACTTTT TTCAAAATTT ACTATGTTTA TTTCGAAATT
 -742  TAGAAAAACG AAGAGTTATT ATTAGTAATG AAAAGCGAAG AAAACTACGT
 -692  AATAAAAAAC AAAATGGCAC GACAATAAAA AAAGTTTTCA CGCAAAATTT
 -642  TCTTGGTGCG CAGAAAGTTA TATATATTAA TTAATTAATT TTCATTTACT
 -592  TTTTTCCCTT TTTATTTTAA AGTTAAATTA TTATTATTTT CATTTAAAAT
 -542  ATAAATATTA TTTAAATATA AAAAATATAA CCTTAATCAA AACAAAGCCT
 -492  TAATCTAAAA TTTACAACAC TTTTAACCTT AAAATTAACT TTAAAAGGAA
 -442  AATGATAGTG TGACAACTAA AAAAGTTGTA TACAACCCTG TCATAGGTTT
 -392  AGAAATAAAT ATATATAATA AAGAGTAAAT TTGTAATTAA ATGATATAAA
 -342  AAAGTATTAA AATAATAATA TTTAGAGTAG TAATATGGTT GTATAAAAAA
 -292  ATGTGGTTGT CCATATATCA TTATTCACTT TAAAATATCA TGACAAATAT
 -242  TTTCACCGAA AGATGGAAAG AACGAAAAGA GCGTTGGATA ATGGAAAAAT
 -192  ACAAGCAATC TCCCTCCAGT ACTTTGCATA ACATTTGTA TTAGTGATGA
 -142  GTTTTTATC ATATATATTT AGAATATAGG AAAATTTTAG AATCACGTGG
  -92  ATAGCTATAT AATAGTAATA TTTTAATTTA TAATGTAGTT GATTTATTT
  -42  GTCAACTGGT ATACATAAAT ATGTGTTGAT AGTGGGTGAC TTGTGGCTTA
    9  AAGAAATGTC CAGAGGCTGA CAACAACTCT GCACAGACTA GCGTAAAC
   57  ATG AAG TCC AAT TTT GCT ATT TTC GTA GTC TTT TCT CTT CTT CTT
    1   M   K   S   N   F   A   I   F   V   V   F   S   L   L   L
  102  CTG GTACCTCTTCAATCTTCTCTACAAAAACTCTGTTGCTCTTTCACCTCTGTTTGTA
   16   L
  160  ATTTGTTTACACTTTTGGAAAATTGAAGCTGATATATATGTAACAACCTTTCAGTTTT
  219  GTCTGCACTGAAACTGATAGAAAATATACGTTTTGTGGATATATATAG GTT GGC
   17                                                     V   G
  274  AGT TGC AGC TGC GCA AGA AAA GAC ATG AGA GGG TAT TGG AAG GAT
   19   S   C   S   C   A   R   K   D   M   R   G   Y   W   K   D
  319  ATG ATG AAG GAG CAA CCT ATG CCA GAA GCA ATC AAA GAC CTT ATT
   34   M   M   K   E   Q   P   M   P   E   A   I   K   D   L   I
```

FIG. 2 (Continued)

```
    GAG GAT TCA GAA GAA GTG TCA GAA GCA GGG AAG GGT CGT TTT GTT
49   E   D   S   E   E   V   S   E   A   G   K   G   R   F   V
    AGG GAC TTC GAT GTA AAG CCT AAT GTC ATA TTA TAT CAC ACA CAT
64   R   D   F   D   V   K   P   N   V   I   L   Y   H   T   H
    GTT GTG CCC ATG AAG CAG AGG CAG AAG AAT AAA GAT TGA
79   V   V   P   M   K   Q   R   Q   K   N   K   D   •
```

493 AGACTATGTGATTGGCAGTTTCAGACTTATTTGGCACCAAATTTATGATGCTCTTGTTGC
553 TGTTTCAAAATTTGTACTCAAACTTTGAACCCTTTGCAGCATCTTGCTTCTTTTTGGTCT
613 TGCTGAATTTTGTCACAGTTATACTGTCACGAATAGTTTCTCTTCATAATAAGCAACTTT
673 TCCTCTC

FIG. 3

```
101001 CAAAACAAAAGCAAATGCCGGTTTTCTTATTATTATTTCGAACTTTAGAC
100151 CTTTTGTAACGTTTCTTTAATTTTTTTCCTTGATAAAGAACCCTATTAT
100201 ATCTTAGCTAAATATTTACCTCATTTTGTTTATGAGCTAAACCACCCCAA
100251 AAATATTGTAGTTTTGCTTTCGGATTTAACTGCCAAGCAAGTGATTAGAT
100301 ATATTAAAGGAAAATGAATGAAAGGACAAAAAAATATAAACGACAATATT
100351 TGAATACTGATATTTATCTCCATTCTCAAATATTTTGATTTATTGTGAC
100401 AATATTTGGTTGTTTCCCATTTGCTACATCTTTGAGGACATGAAATGATA
100451 ACATATATATGAACGAGTATAATACATTCTCGTTTCATTTTACAAATAAT
100501 GTCAATTTATGCTAACATTTTTATTTAAAAATTATCCTTATAAGATTTC
100551 AGTGTATTATTTTACCATGGTACTGTAAAGTCGGATGCTATATATATATA
100601 TATATATATATATATCAAAAATGACACTGAAGAATTTATTTGAACTAAAA
100651 CTAAAAACGTAAAATAAAAAGAATTTTTCAAAAATCAAAAATTTTATATA
100701 AAAATATAGATAAAATGTTAATATAGTACAACTTCTATTCAAACAGAGAG
100751 AATAAATCTTCTATAGACAGTGAATATCCATTATAATAACGAGCAATAGT
100801 TGTAATGTTGCAGTACAAAAGAGAATTGTAATATTTGTGCATGATTGAG
100851 AAATCTAAGTTGACTTTGAATTAAAAGGCTAATTCCAACAAGTACATGTA
100901 GAAGTTGACTATAGCTATATATTTACTACAAATTGATCATTTCAAGAAAG
100951 ACATTTAAATTAAGATATGCATGCATGACTTGATTGAACCCCACTCGCTT
101001 GCTTCGTGCCATTCGACAAGATGTTACTTTTAAATGCAAGGTAAATTATG
101051 GATATACTCTTCTGTATTTTTGTAGTAGATATTTTACGAAAATTGTTT
101101 TTTTTCCAAAATCAAATGATATTTATTAATTTTCAATATAGAATTAATTA
101151 AATTTTAATTAATTTTGAAGATTTATATGCTGCAGATTAGATTACCATTG
101201 GTGAAATCATGTTTAGGTAAATAATAAATGATGTTGTAGTTTAGGAAAAA
101251 AAAAAATTCTTTAATCTTTATGTAAGAATGTTAAACTTCAATTATAAAAA
101301 TATGAAGCAGTATTATATAAGATGTTTAACTAATCGAATAATATTTTTTG
101351 GGATGAAATTTTCTTGCATATGTTTCTAAAAAAATAATATGTGAAAAATT
101401 AACATTCATTGTATGTTTATAAGAAATATATGTGAGTTTTGTTTAGATAA
101451 ATAATACTTAAAATTAAGAATTTGTAAAGTTATACTGCACTTCAAATATG
101501 TTATTTTTCCTTTTATTTAAAATATCAGCAACATTCTAAATGATTTAT
101551 TTTCTTTAAAAAATTGAAAAAATGAAATTAGCAAATATGTAAAATTTAAA
101601 ACGAATTTAAGAAAAAACTTTGTAAAGATATGATATGCTTTATAAAAAAA
101651 ACTTGGTGGCGTACCTACTAAATATGATCACATTAGAGATTTGTATCCTT
101701 TAGCATATAGTATGTAGTATAGATATCTATATTTTATTTATTAAAGAGC
101751 ATATTCATAATATAGGTATTATATGTTAATTACAATAAACGTTCAATTCG
101801 TTATGTTAGTTTTTAGAAAACTTATTGCGTGTGCATATCAATGTGAGAAA
101851 GCGACTCCACATGTGAGATGTTGGTCTGAGAAAGCTTTCTGCACTTGGTC
101901 GGAACTACTTCATGGACTAGAATGCAATCCATCTATTCAAAGAAAAGCAG
101951 TTGTCCATGCATGCCTCGGTTTTCACATTTGGAAGCAGCGCAACAATGT
102001 CTTACATAATATGCGATCGATCACTCTGCAACCAATATTCAAGTACATAG
102051 ACCATGACATCAAAAACATTATCACACCGAGAAGAAAGAAACGTCAATTT
102101 GGTAACTTAATGGCGTTATGCCTGCGGTGAATTCTCCTAAGAGTTCTCCC
102151 AAATTTATTGATTCCTTGTTTTAACTTTTCGCCAAAGAATCATACAT
102201 ATAGATTTGACACCATTTCAACTTATCAAATACAAGTGAATAAATAATTT
102251 CAAGCTTGAAAGGAATTTAATCATGATCTAAACCTAAACGACAAATTCTT
102301 CACAAGTGAGAATCACTAATTGACTACCCCTTGGTCGCATATACATCATT
102351 GTTGTAAATCTGAAAATTGGTTTGGATTTGATCTGATATGTCATTCATAT
102401 AAAACTTGTATTATTTATTTTAGAATTTTGCCGCAAACAGATAAATCATC
102451 ATCTATTTAGAAAATTTTCATTTGCACCACAATTAATCAGGGGAAAAGGT
```

FIG. 3 (Continued)

```
102551 ACAAATTTTCAAATACCACTTATGAGAAGCACTAAGATCACCTTTTTCTT
102601 TATGACTTTCTTTCTAAAGCTAAGCTGGTAGTCATGACTCATGATTATCC
102651 TTTTCCTAATGGGAATATTGTGGAAGCGGTTTCAAATCTTTAGACAAAAT
102701 TCCATGGCCACTAAAAGTTAGCAAAGTTAAAATAAGTTTAAAAAAATATG
102751 AGTGTACTTGGCCATATGCCATATTGTTGAGATCATAACAAGAGAAATAA
102801 TAGTTTATTGAAGTTTAGATCATAATCACAATACATCATTGCCTTCATCA
102851 ACATTTTCCATGGATTTGAGAGGATCAACTTCAATACTAATGGTGGGGTC
102901 TTATTCATCCATTGCTCTCTAGCCAATTAAGCAGTTAGGTTATTTGTGTA
102951 CTCTAGTAGTTGCCAAATCAATCTTAATATTCACAATGTTGTAATTTCTA
103001 ATTACGTATAGATAAATGACTAGATAACACGTGGCTTTGGTTTTATCAGG
103051 AAAGTTTTCCAAATCATATATATGAATGTAGAATAGTGTTCTTCATTAAT
103101 TATTAATTAGCATCTCACCATCTGAGACTGGGAGCATGTGACAAGTTGAC
103151 ATGTGTATTAAGAGAACTTTGAGAAACCACTTTTATGATACTCCCATCT
103201 GAGACTGGGATGAGTACCATTTTATAAAATATGAGTAGTGAAAAATAT
103251 TCAAAAAAATTCTAACATGTCCTTTAAAACATTTTAACCTTATAATTTT
103301 AACAAACATCTTCCAATATGCGTTATGAAAACTTTATAAAACTTTTTTAT
103351 AACATGCTTTTGAAAATTTTATAAATCTGTATTTTTAGAAACAAAGTGAT
103401 ACTTTTGAAAATAGACAAATGAAGTGCTATTTTTAAAATTGATATCATA
103451 AGTCTTAACTGTGGTTTGTTTGAATTTTATTTATATACTTGTCAAAATAA
103501 AACTAAATAAATAAATTAAATTATTTTATAATCATGAAGATAATATTATC
103551 ATAAAGATAAATATAAAATCAACAAATTTATATTTGTTAATAAAAATAC
103601 TTTGAGCTCTTCTTCATAAGACTTTTCCAGCTTCCATCTAGAAAATCACA
103651 TAAATTAAAAGATAAATAACCGAATAAACATAGTTCACATTCTAACTCTT
103701 AGTCTTAGATTTGTTTAATTTTCAAAGGTTTAGGTATTGTATATGTTTT
103751 TTTTATTGGGTTGCTAGATTTTGATCCAAGAAGAAATGACGGGTTGTAGT
103801 ATAGATGGTTTGTTTGAGTTTTTTCCCCTTGGTTTACTTCGTTTGGTTTT
103851 TGTCCCCAGAATTGTTCTTGTACTCGCTGGTTTATGTCTCTACAAAGTCC
103901 ACGACCATTGCCGGCTCTTTGTATTTCAACTTGAATTCTAAATTCGATTG
103951 ATGAAAAAAAATGTATCTCTTAAAGTCCATTAGTACCAAAAATAACTAT
104001 ATCATTACTACATAAAATAGTCTTGGGTTTTCCAAAGTATTTCGTTGATA
104051 TATGTTAAGAGTTCGAAATAGACACATAGATATAATGTTGAAATG
104101 TCTCACATAATTATCTCCTTTTCTCTTCATTTCTCTACCTCTCAAGTTTC
104151 CAATCCCACCCTAAGGTAATTTATTTCTTAACCTAAGTAAATTTGTTAAC
104201 AAATCTTAACTAGCTACAAATGTGTATTACAAGTCTTAAATAAAAACCTA
104251 CTTTAATTCAAAGGTATTAAACCTTCCTAAATTGATACTTACTTAGTATC
104301 GATCGGTCTAGTTTAGGGTTTGGACAACACACCATCATGGGGACGAAATT
104351 AGTCATTCTACGGTGTCCAAGACACAAATCTCGGACTCGATGTGGATATG
104401 ACACTTCATTATAACTTTAACTTCATAAAAACTAACTATTAGGAGGAAG
104451 AATCGGAATCTGCATATCAATCACAATAGACTATAGTATACTTAGATTTT
104501 GATCTAATCAATGGGCTCCTTCAACTAATAAGTAGCCCACTACCAATAAT
104551 GAAATCATAAGACATTATTAAATTAATCAATGTTCTAAAAATACTTTGGT
104601 TATGTGTCCCGTAGAGCTAATGTGCACACACAATGAAGTTGACCCGTTT
104651 CACTTGTCCCACTTTTATGATCTTTTCTTTTAGGTTAAATCCAACTTTTA
104701 TAATCTCATCTTGTTATCAAACAAAACTTTTGGCCTGTCTTTTTCATAAT
104751 TTAAAGTAACTCTCACGGAGAAAAGCCAACATTTTCTTCTTGTTTTATTC
104801 TTTTTAAGAAAATGAATTCAAGGGGACCCCAAATTTAAAAGGAAAACCA
104851 AAACTCCTTTCTATGTATTTATTACTTGAAGTTTTCTATGTAATCAACAA
104901 TCCTAACAGTAGAGAATAAAAAACATCGTTTTGGGAGGTTTTATATTAGC
```

FIG. 3 (Continued)

```
105001 CCTCTGTCAATGGAGCTATATCACTTGTCATTTTGCTTAACCCTTTGCGG
105051 GAAGATTGTTATGAAACAGTTTTAATGGAATTCTAGTTGCCAATGTCACG
105101 TTTAATATGTTTGTCCCTATACTTATTGAATCTTATAATCTTTGTTAT
105151 AGAATTATCTACTTTTAGTATTTTACATTAACATAATCTATAGAATTCTT
105201 CTTTGTTCTATACAATTAAACAAGTAATATATTCTTAATACATATTAAAA
105251 ATGGTGGTGTTGCTATCTGAGCTGTAATAGTTGATTGCTCCAGAGAAGAA
105301 TAGACAAAATCCTTACTTAAGAGGCCCACCACTCTGAAAATTTAGACAA
105351 GAAAAATTAAACAAAATTAGGTTACACATATTATCATTTATÁTATATGCA
105401 CAACACAAAGTTGACCTTGCAATGTACTATTGAATAAAATAAATAAATGC
105451 AAGAAGAGAGGGAATTATCACTGTTACCAAGAAAACAACTTCCTCTAAAC
105501 AGGTCTCTATATATATAAACTTTAACACCTAAAGAATTAACACAGATCAA
105551 GAAAAAATCCTCAAAACAAAAGTTAAAGCAGAC ATG AAG CAA CAG CAA
                                            1       M   K   Q   Q   Q
105599 CGT TAC TTG GTC GTC TTC ATC GTC CTT TTA AGC TTT CTT
        6   R   Y   L   V   V   F   I   V   L   L   S   F   L
105638 CTG GTAAAGCTTCTTCCTTAATTATATTAAAACCCTAATTAAGATCTCATATA
       19   L
105691 TCTGAATGTTGTATATATTTGTTGGTATAG TTT GTG AAT CTG AGT
       20                                 F   V   N   L   S
105736 GAA GGA AGA ACA GGA GGA GTT GCA GAA GAA TAT TGG AAG
       25   E   G   R   T   G   G   V   A   E   E   Y   W   K
105775 AAG ATG ATG AAG AAT GAA CCG TTG CCT GAA CCA ATC AAA
       38   K   M   M   K   N   E   P   L   P   E   P   I   K
105814 GAG CTT CTC AAC AAT CCT TTT AGG ACC GCA CAA GAG AGA
       51   E   L   L   N   N   P   F   R   T   A   Q   E   R
105853 TTC ATC CAG AAT TTC GAC ACC AAA TCT GTT GTC ATC ATC
       64   F   I   Q   N   F   D   T   K   S   V   V   I   I
105892 TAC CAC AAT CCT AAT GAA TAA TCAATGAAGTCTCTCATATAG
       77   Y   H   N   P   N   E   •
105934 ATATCTATGACTTTAATTTGTGTTTATGTATGGATCGACTTATACGTGCA
105984 CGTATATGTTATTAATTAAGAAAGAAAAGCTGCTTGAGTTGTTGTGTT
106034 ATACACGTATACTAAATATGTTCTGTTTAGTGCAGAAATGTTAACCCTAG
106094 CTATAAGGGATTTTTGTTCTTTTTTTTGTTACCATTAATGTGAGTGA
106144 GTGAGTTTTGTGTGATGAAAATTAGATTTGCTTCACATTTTGTTTTGATA
106194 TATATAAATCAATATACTGTGCCTTTCGTGTCTTGTTTCTTATATTATTT
106244 TGTGACATTAATTAATTATCTTATCAAAAATTTATTTATTAACTGTGTC
106294 CTATGGAAAAGATGAACAATATGAGTTAACCTCATCTCAAGGAGATTCT
106344 TTTTTGTTTGTTTTC
```

FIG. 4

```
   1 AAGCTTTACAAATGTCCCCCAAAGATGAAACCACGTTATTATTAGTAAATCCTGAAAAGG
  61 TTAACGCTTCTGTTCCTCGAATTCTAAACCATCTGAAATATCTAGTGGTTTAAAATGGAG
 121 ACTTGAGGATATAGTCTCCTGAACCAGCTGTCACGGCTGAGTTAGATAACATTACTGAAT
 181 TTCTACGGGAGCGGTTGAAATCACTTTCGCCCCTTTAAGAAGAAGCCTACACCGGGCACC
 241 TTCTTTACGCAATTCGAAATTTAGTCTTGCCAGGCAGTCGTTGGATCGAAGGTCTTTTTC
 301 GATACCGAGGAATCTGACTTTGCAAGGAATAATTCCTAATCACACCACCCCAACCCCTGA
 361 ATACACTTCAGGACCCTCTGAAACCAACTTCGTTTCGGCTAAATCACAAGAATCTCCCAC
 421 TCATTCCGATTTTAGCCAATTAAATATGATATCGGTCTGGGAAGCCGATAAGGAAATTCT
 481 ACAAAAAGAGTTTATGAATGAGGAAAATAAGGAAAAGAGAGAACTATTTTTTAGGTACCC
 541 TGAAAGAGAACGAGAAAAATTTAGAAAAAAATACTACTCTCATCTGTACACTGTTCAAAA
 601 GAATATCCnnnnnnAATGGTTAGATAATATAAGAAAAGGATAAGTATGATTAAACTGAAAC
 661 CACGTCGGCAGAAACAAAGTGAATTCCCCCCTTTAGAGGAAGTTCGTTTCTTAAATATAG
 721 AAAACAAAGAAGTAGTCGCCTCCCCTTTTAAAATGATCTCAGAAAAACGAGAAGTAAGTA
 781 TAAAAGATATTCAAAATCTACACAGTCAACTAAATTTTACTAATCAAATGCTTTTTCAAT
 841 TAGCAAATAAAAAACAAAGAAAAAGmGAAAATTGAAGAAAAATCGTTAATAAAACCAT
 901 TTAAATTCTCAGAAGAAGAGATAAAACAGTTAAAAATTGGTCAAACTTTGGATTCTTTAT
 961 ACGATGAAGTAAAACAAAAGTTATCTATCTCGGTAATAAAAGAAAAACCGAAATCTAATA
1021 ATGATATGCCCAAAAGGACAAATCCAAATCAAGAAGTTTTAGACGAAATCGAAAAGAGAT
1081 TAAAACAAACTCTGAACGACACAATAAATGTGATAGAAGAAACTAAAAACTCAGACTCAT
1141 GTTCAGAGTCTCCCGATCGTATTGAAAAAATAAAACGTAATAAATCAGAGATTTCCAGTA
1201 AGCCGAAATTTTTACACTCGCCCCACCTTCGATATCATCGAGATGGCGATGGACACCTCA
1261 GCATTGATGGAATGGATACTGAGTGATATGATGGATGACAGATGATGAATATAGAAAAAC
1321 TCACGAAATAACAATGGCCGCTACAGCATATAGAGTAAAACATACCGAGGAACAAACAAT
1381 AAAATTAATTATATCTGGATTCACGGGAGTATTAAAAGGCTGGTGGGATAATTACCTCAT
1441 GCCAGAACAAAAGAATTATGTTCTAAGCTGTGTAAAAATAGAAAACGAAGAAGGAATACC
1501 ACTAATGGTGGAAACATTGGTGGTAGCAATAATTCATAACTTTATAGGAGATCCAAAGAT
1561 TTTTGAAGAAAGAACATCTTTATTACTTCATAATCTAAGATGTCCAACCTTAGGTGACTT
1621 TAGATGGTATTCAGAAAATTTTTTAGCTATGGTTTTAACAAGGGAAGATTGTAGAGAACC
1681 TTTCTGGAAAGAACGGTTTATAGCTGGATTACCGGATATCTTTGCTGAAAAGGTAAAAGA
1741 AAATTTACAAAAGGAATGCCCAAACACCCAATTAAAAGATGTACCATACGGGAAAATAAG
1801 TTCAGTTGTAAAAAATACAGGTCTTCAGTTATGCAATAATATGAAAATAGAAAATAAGAT
1861 AAAAAAGAGTGAGAGTCAGGGCATCAAGGAATTAGGGGAATTTTGTACTCAATACGGTTA
1921 TGAACGAAATACCCCTCCATCAAAAAATAAAAGAAAATAGCAAAAGAAGAACAgGGAG
1981 AAACAAGCGCTAAAACAAGCGCTAAACCAGCACGTAAAAATTTTAGAAAAACGGTTAATT
2041 TTAGAAAACCATGAAAGTCTAATGATAAGCCCACTATAGTCTGTTATAAATGTGGACGCA
2101 TAGGACACATGAAGCGAGACTGTAGACTAAAAGAAAAATTAGTAATTTGACCATAAGTG
2161 ATGAATTAAAAGAACAAATGGAAAAACTTCTGATAAATTCCTCCAGAAGAGGAAGAAACA
2221 GAAGAATCAATAGGAGATTCTGATTACGAAGTATTGGACATGAGGATAACAATTGTAATT
2281 GTGTCTATAAAATAAATACGATAAGTAGTGAATTAAAATTTGCGTTAGATTGCATTGATA
2341 AAATTAATAATCCGGAGGAAAAGACCAAAGCCTTAATAGACATGAAAAGGCTACTCGTTG
2401 AAAAGATGAACCCAGTTCATCTTCACAAAAACCTGAATTTATAGGATATGATTTTAAAG
2461 AAATATTGAGAAAAGCGAAAACATCACATAAAGAAATAACCATTAGCGATCTTAATAGTG
2521 AAATAAATAAATTAAAAGCCGAAATCGAATCTATAAAAGTCGAGCTACAAGAATTAAAAG
2581 ATAAAATTATACATGAGGAATCCATCTCCTCTGCCGACGAAAATTCACAAGAAGAGGAAG
2641 CTAGTAGACCTTCCATCAAAGAAATAACATACAAAAGACAAAAGTGGCATGTAAAAATAG
2701 CCCTAGAATTTGTTTGTTTTGTGACCGTTTCATTGTGGTCAAAGATGAGTCCTTACCTAA
2761 CACAATAAAAAACGTTACTCTTAAATATCAAAGGAGAGCTACAAATATCAATGAATGAAT
2821 GACATTAATATTTTTCTTTAGTTTTAAAACTTGAATGAGTTGTTTTCATAAATATCTGAC
```

FIG. 4 (Continued)

```
2941 ATATTTTTATCTCAAAGTCAACGAAATATTATAAAAGAATCAATTAAAAAAAATTATTCT
3001 TTTGCAGAAAAAAAAATTAAAAATATGAAACTCCTCCACACCATATTACCATATTATAAA
3061 TATAAAAAAACCTCTCACAAATGTGCATTCTGGAATTCTTTATGTTGAGAGATTAATCTC
3121 TAAAGAAAAAGGTTGAGAAAGGTGCAGCAACA ATG TCT CCA TTC TGT AGA
   1                                    M   S   P   F   C   R
3172 AAC TTT TCA ATG GCA TGG GTG CTT ATG GCA TTT GTG TTG TTT
   7  N   F   S   M   A   W   V   L   M   A   F   V   L   F
3214 GCA AAC AGT GCT ATG CCC ACA AAT GGA TCC ACT GTT GGG GTA
  21  A   N   S   A   M   P   T   N   G   S   T   V   G   V
3256 AAA AAC ATG TTG GGT GGT AAA TTG ATG CTA AAC GTT TTA TGT
  35  K   N   M   L   G   G   K   L   M   L   N   V   L   C
3298 CCC CAT ATT GAT AAG CAA CAC ATT ATC CCG AAT GGT GGT TCA
  49  P   H   I   D   K   Q   H   I   I   P   N   G   G   S
3340 TTT GAG TGG AAG TAC AAT GGT GGT GCT CCA CCA ATA GGA CAA
  63  F   E   W   K   Y   N   G   G   A   P   P   I   G   Q
3382 TCA CCA TTC ATG TGT TTC TTT CGG TGG AAT AAT GTT CAT CAC
  77  S   P   F   M   C   F   F   R   W   N   N   V   H   H
3424 TCC CTT GAT CTG TGT TCA CCA AGC AAG TAT ACT GGT TGT GAA
  91  S   L   D   L   C   S   P   S   K   Y   T   G   C   E
3466 AAT GCC ATT TGG GAA ATC AAA GAA AAG CAA TTT TGT AGG TAC
 105  N   A   I   W   E   I   K   E   K   Q   F   C   R   Y
3508 AGA GGT GGA CCT ATT AAT TAT TTT TGC TAT GAC TGG GAT GAT
 119  R   G   G   P   I   N   Y   F   C   Y   D   W   D   D
3550 TAG TTATATAGATTATTCATGTTTCATCTCAATAAAAAATGACTTTAGAGTGATTCTT
3609 AGTTTGCTTAACATTCTTACATATTCCTAACTATTCCGTCACTACCACCCGTAACTATAT
3669 TTATTTAAAATTAGTATCTGTCACAGTTTTATTTTTAAAAAAGGTTATGTGGATTAGAAG
3729 AGAGATAAATATGTAGACGGTCACCAACCTTAATTTTTGAACTATGTAAGACTATATTGA
3789 CCAAGAATATATGTTTAAACTCATTCATTTAAAGACTATATCTCCATTTATGATTATGCA
3849 AATGCAATTAGTTTTTTTTTCATTGAAGAATTCAAAAGAAAGTTATCATTAAAAAGTAT
3909 CATTAAATCACTTATATGTTGTTTCTTAATATCCTTATTGTTAATAGAATAATTTTTTT
3969 ATCCTTTAATTAAGGTTATTACTACTTTTTTTTCATATCTTCATTATTTTGAAATATTTT
4029 TAAAATTTATCAATTTTGTAACACCCCAGAAAATACATGTAACTATCACTTTTTTTTA
4089 TATTACAAATTTATGACTTATAGAAATACAAATATTAAAAATATAAGGTTCAAAACTACA
4149 TCCTAAAGTCTTTCAGACCCTCTGACACATGTATCATCTGCTCGTATATGTGATACAGTC
4209 ATCGCAGTTCACAAGATAACAAGAAAACCAAGGGTAAGCTAATGAAAAAAAATTCCATAA
4269 CATATTTAATTCATGCAAAAAGAACCAGTCAAAGTAATCATTTATAAACATTTCTTTAAA
4329 TATTGTTATATAAAATTTCAATATCAATTTCATCATTCATATAGACCACACATGGATCTA
4389 TTTTCAATCACAATCATTGGATTTCATTTTAATCCTACTTCGnCTTCCAGAAGACTCATT
4449 AAGTATGCCCCTACCAGAGACTAACACCTAATCAAAGAGAAATGATCAAGGTAAGTTCAA
4509 ACATCCAATAACGAGTGCCTACAGTGGGACCCAATGTGTATGAACTCCTTATCAGCTTCT
4569 CACCACCTGATATCTTATTCTATATGACGTAGATCATCAGTGAAACTAGAGGATCTCCGT
4629 TAAACATATGTTTTTATACTTAATGTCATCAAACAACAACTCACACATTATCCCAAATG
4689 TATGACATCAATTTCATACAATTTTCATCATTCATATATAATACATATCATTGAATCACA
4749 TAACATTTAAAAATTCATACCATTCAAGAACTTTTCCAACATCAAAAGCAATATTTACTT
4809 TCAAACTATCAAAATATAATTATTATTTAATAAAGCTt
```

FIG. 5

```
142000  TTATCTTATTTCCATATAATTGTTGTTTTACTTTCAAAATTTTTAATTTT
141950  TTATATTTATCTTTTTACAGTTTAAAATTAATAAAATGAAACTTTTTTTC
141900  TTAAATGTGTTAAAATATAAAATCAAAAAAGTTGTTATATGGTACATGGC
141850  ACAATCTTATAAATTATTAATTTGAAAACGATACTTTATATAATAAAATT
141800  ATCTTAGTTGACATTTTTATTAGTGTTTTCAATCATATTTTTGTTTGCTT
141750  GATAAGCGTAAAACAAATCAAACTTAACGATACTTTATATAATAAAATTA
141700  TCTTAGTTGACATTTTTATTAGTGTCTTCAATCATATCTTTGTTTGCTTG
141650  ATAAGCGTAAAACAAATCAAGTAAAGTTGGGCACCTCAATTGTTTTAAAA
141600  AAGTTTGGGTACCTCAAAAATTAATAGGTCTTGTCAGATTCTTACAAAAA
141550  AAATCTGGAAGAATTTATGAAAGAAGGGGGGGGAGGGGGGGAGGGGGGGG
141500  AAGTGAAGATGAATATTCAACAAAAGAGGGTAGGCATGATGTTAAGTGAG
141450  TTAAAAAACTATGTTAATGGAGACAATTTTCTGTTAACAAACCCGTTAAT
141400  TGAAAACGATAGCATTCTTCTCTAACAATGTAAAACGATATTGTTTTATC
141350  ATAACTACTCATTAAATTTCTGAGTTTCAAATCATATAAAGATTTAGGGG
141300  GGTGTATTCAATTAAGGATTTGAAATGATTTGTATTAAAATGACAAATCC
141250  CATGTTATTTCAAACATGAATTGTAAAACTTTTTTAAAATCAAGTGTTA
141200  TTAGATTAGTGATTTTAAAATGTACAACCAAACCCACTGTTATTGGAAAC
141150  ATTTTAAGTAGTGGATTTAAAATGACTTGAGTGATTTGGGTGGGATTGC
141100  AGAAAATTTCTTAGTTAAGAATTCAAACATCCAAATCTCATGGTTTCAAG
141050  TAGAATTTGGGAGAATTTTAATAACAAATCTCCTAATTTACCAAAAGTCA
141000  CCAAAATCATTTAAAAACTCATTAAAATTTAAATGATTTCAAATCTCCAG
140950  TTGAATACATCCCCTTGGAATTAGAGATTTTGCTCGATTTGGGACCTAAG
140900  ATTGAATTTTGGGGATTTAGTTTAATCGTTACAACAAAATGACATCGTAT
140850  TATTGTTATAGGAAACAATGTCGTTTTCAGTTGACATGTATGTTAATAGA
140800  AAATTAACTCTATTAACGGGATTTGCTAACCCATTTAACATCGTAACTAA
140750  ATGGTCAAGTCAATAAAAGTTTGGTATTTATTTGAAAAGTCAACGTAAGT
140700  TTGATATTTATTTGAAAAGTCAACATAAATTTGATATCTTATTTCGTTTC
140650  GACAGACATAAGGATTTACATCAATGTTTTTAATAAATTAAAGATTATTA
140600  TGACATTTTTTCCATTTAAAATTGCCAATGTTTTCGAAACCAAGATACTC
140550  AAAATTGACATACCTAATTCAATCTACATTTGTTTGACAGCAATTCACGT
140500  GCCTTGACCACATGGCACATACTGGCAATACATCAATTTTAAGGAAAAGG
140450  TAGATTCGGATACAATATAATGGAAATAAGTGGAAAGGATCATTGACTAC
140400  TTGACTTGTAACAAACAACACACAGTATATAACTCATTCGACATTTACAA
140350  ACAACATTGTGCTAGCTTAAACTCCCTCTCCTATTCAAAAAA ATG
     1                                              M
140305  GAT ATT CCA AAG CAA TAT CTA TCA CTA TTC ATA TTG
     2   D   I   P   K   Q   Y   L   S   L   F   I   L
140269  ATT ATC TTC ATA ACT ACA AAA TTA TCA CAA GCC GAC
    14   I   I   F   I   T   T   K   L   S   Q   A   D
140233  CAT AAA AAC GAC ATT CCA GTT CCC AAC GAT CCA TCA
    26   H   K   N   D   I   P   V   P   N   D   P   S
140197  TCA ACA AAT TCT GTG TTT CCT ACC TCG AAA AGA ACC
    38   S   T   N   S   V   F   P   T   S   K   R   T
140161  GTG GAA ATC AAT AAT GAT CTC GGT AAT CAG CTA ACG
    50   V   E   I   N   N   D   L   G   N   Q   L   T
140125  TTA CTG TAT CAT TGT AAA TCA AAA GAC GAT GAT TTA
    62   L   L   Y   H   C   K   S   K   D   D   D   L
140089  GGT AAC CGG ACT CTG CAA CCA GGT GAG TCG TGG TCT
```

FIG. 5 (Continued)

```
140053  TTT AGT TTC GGG CGT CAA TTC TTT GGA AGG ACG TTG
    86   F   S   F   G   R   Q   F   F   G   R   T   L
140017  TAT TTT TGT AGT TTT AGT TGG CCA AAT GAA TCG CAT
    98   Y   F   C   S   F   S   W   P   N   E   S   H
139981  TCG TTC GAT ATA TAT AAA GAC CAT CGA GAT AGC GGC
   110   S   F   D   I   Y   K   D   H   R   D   S   G
139945  GGT GAT AAC AAG TGC GAG AGC GAC AGG TGT GTG TGG
   122   G   D   N   K   C   E   S   D   R   C   V   W
139909  AAG ATA AGA AGA AAC GGA CCT TGT AGG TTT AAC GAT
   134   K   I   R   R   N   G   P   C   R   F   N   D
139873  GAA ACG AAG CAG TTT GAT CTT TGT TAT CCT TGG AAT
   146   E   T   K   Q   F   D   L   C   Y   P   W   N
139837  AAA TCT TTG TAT TGA CAACAATATGCTGATGTTCTGTCTTTTAC
   158   K   S   L   Y   *
139793  GACTCATGGAGTTTCATTGTTTGAAACAATAATATAAAACATATAAAATT
139743  TCTATTATTCCAAGTTCCAACTTATAATAATTTGATAATCATATCATATT
139693  ATCATCTTAAGCATTCAATGCTACAAAGATAATACCCCCAAGCTATTTTA
139643  CATTAAAAGCTGAAACAGAGACACAATACTAACGATAAAAGTTCGT
139593  TCTTTATGCAACCATACATACATATACACAAAGATAGACAGGTAGTGTCC
139543  TAATAATTCTACTTGGGTGAGGTATGAACAGCAGCAACAGTAGATACCATA
139493  TGTATCCATACCACACATATTATGAGGCCCTCTGCAGATTTTGTAGTAAC
139443  CATGCTCTCCCCACATCGCTCCCCACGAGTTCTTGATAATCCAA
```

G564 promoter:
Gain of function constructs

⊕ = Gus Activity in Suspensor
⊖ = No Gus Activity in suspensor
▨ = Region Required for Bus Activity in the Suspensor

```
Web Signal Scan Program

Database searched: PLACE
URL: http://www.dna.affrc.go.jp/btdocs/PLACE/

This is the sequence you submitted
>G564 promoter (-921 to -662), 450 bases, 3D1AOBF4 checksum.
TGAAAAGTGAAGAAAACCATGTAATGAAAACAAAATGGCACGACAATCAA
AAAAAGTTTTCACGCAAAATTTTCTTCAAAATTTATAACATTTTCATGTT
GTGTTTGTTTCAAAGCCTAGAAAAACGAAGAGTTACTATTGGTAATGAAA
AGCGAAGAAAACCACATAATAAAAACAAAATGGCACGACAATCAAGAAAA
AGTTTTCACACAAAACTTTTTTCAAAATTTACTATGTTTATTTCGAAATT
TAGAAAAACGAAGAGTTATTATTAGTAATGAAAAGCGAAGAAAACTACGT
AATAAAAAACAAAATGGCACGACAATAAAAAAGTTTTCACGCAAAATTT
TCTTGGTGCGCAGAAAGTTATATATATTAATTAATTAATTTTCATTTACT
TTTTTCCCTTTTTATTTAAAGTTAAATTATTATTATTTTCATTTAAAAT Notation:   H = A, C, or T
            R = A or G
            K = G or T
            W = A or T

RESULTS OF YOUR SIGNAL SCAN SEARCH REQUEST

/tmp/signalseqdone.9437:   450 base pairs
Signal Database File:
```

| Factor or Site Name | Loc.(Str.) | Signal | Sequence | SITE # |
|---|---|---|---|---|
| -300ELEMENT | site | 1 | (+) TGHAAARK | S000122 |
| 2SSEEDPROTBANAP | site | 101 | (-) CAAACAC | S000143 |
| ACGTABOX | site | 296 | (+) TACGTA | S000130 |
| ACGTABOX | site | 296 | (-) TACGTA | S000130 |
| AP3SV40 | site | 159 | (-) TGTGGWWW | S000169 |
| CAATBOXI | site | 44 | (+) CAAT | S000028 |
| CAATBOXI | site | 189 | (+) CAAT | S000028 |
| CAATBOXI | site | 323 | (+) CAAT | S000028 |
| CAATBOXI | site | 138 | (-) CAAT | S000028 |
| CANBNNAPA | site | 101 | (-) CNAACAC | S000148 |
| CCAATBOXI | site | 138 | (-) CCAAT | S000030 |
| CEREGLUBOX2PSLE | site | 55 | (-) TGAAAACT | S000033 |
| CEREGLUBOX2PSLE | site | 201 | (-) TGAAAACT | S000033 |
| CEREGLUBOX2PSLE | site | 333 | (-) TGAAAACT | S000033 |
| DOFCOREZM | site | 4 | (+) AAAG | S000265 |
| DOFCOREZM | site | 53 | (+) AAAG | S000265 |
| DOFCOREZM | site | 112 | (+) AAAG | S000265 |
| DOFCOREZM | site | 149 | (+) AAAG | S000265 |
| DOFCOREZM | site | 199 | (+) AAAG | S000265 |
| DOFCOREZM | site | 282 | (+) AAAG | S000265 |
| DOFCOREZM | site | 331 | (+) AAAG | S000265 |
| DOFCOREZM | site | 364 | (+) AAAG | S000265 |
| DOFCOREZM | site | 419 | (+) AAAG | S000265 |
| DOFCOREZM | site | 216 | (-) AAAG | S000265 |
| DOFCOREZM | site | 399 | (-) AAAG | S000265 |
| DOFCOREZM | site | 408 | (-) AAAG | S000265 |
| GT1CONSENSUS | site | 120 | (+) GRWAAW | S000198 |
| GT1CONSENSUS | site | 141 | (+) GRWAAW | S000198 |
| GT1CONSENSUS | site | 196 | (+) GRWAAW | S000198 |
| GT1CONSENSUS | site | 253 | (+) GRWAAW | S000198 |

Figure 8

| | | | | | |
|---|---|---|---|---|---|
| GT1CONSENSUS | - | site | 69 | (-) | GRWAAW | S000198 |
| GT1CONSENSUS | | site | 90 | (-) | GRWAAW | S000198 |
| GT1CONSENSUS | | site | 347 | (-) | GRWAAW | S000198 |
| GT1CONSENSUS | | site | 388 | (-) | GRWAAW | S000198 |
| GT1CONSENSUS | | site | 436 | (-) | GRWAAW | S000198 |
| GT1CONSENSUS | | site | 218 | (-) | GRWAAW | S000198 |
| GT1CONSENSUS | | site | 401 | (-) | GRWAAW | S000198 |
| GT1CONSENSUS | | site | 402 | (-) | GRWAAW | S000198 |
| MAMMALENHAN | | site | 158 | (-) | GTGGTTTK | S000121 |
| MARTBOX | | site | 324 | (-) | TTWTWTTWTT | S000067 |
| MRE1 | | site | 356 | (-) | TGCRCNC | S000068 |
| NTBBF1ARROLB | | site | 418 | (-) | ACTTTA | S000273 |
| POLASIG1 | | site | 168 | (+) | AATAAA | S000080 |
| POLASIG1 | | site | 301 | (+) | AATAAA | S000080 |
| POLASIG1 | | site | 324 | (+) | AATAAA | S000080 |
| POLASIG1 | | site | 237 | (-) | AATAAA | S000080 |
| POLASIG1 | | site | 411 | (-) | AATAAA | S000080 |
| POLASIG3 | | site | 268 | (-) | AATAAT | S000088 |
| POLASIG3 | | site | 427 | (-) | AATAAT | S000088 |
| POLASIG3 | | site | 430 | (-) | AATAAT | S000088 |
| POLASIG3 | | site | 433 | (-) | AATAAT | S000088 |
| POLLEN1LELAT52 | | site | 11 | (+) | AGAAA | S000245 |
| POLLEN1LELAT52 | | site | 119 | (+) | AGAAA | S000245 |
| POLLEN1LELAT52 | | site | 156 | (+) | AGAAA | S000245 |
| POLLEN1LELAT52 | | site | 195 | (+) | AGAAA | S000245 |
| POLLEN1LELAT52 | | site | 252 | (+) | AGAAA | S000245 |
| POLLEN1LELAT52 | | site | 289 | (+) | AGAAA | S000245 |
| POLLEN1LELAT52 | | site | 362 | (+) | AGAAA | S000245 |
| POLLEN1LELAT52 | | site | 71 | (-) | AGAAA | S000245 |
| POLLEN1LELAT52 | | site | 349 | (-) | AGAAA | S000245 |
| PYRIMIDINEBOXHV | | site | 400 | (+) | TTTTTTCC | S000298 |
| RAV1AAT | | site | 97 | (-) | CAACA | S000314 |
| ROOTMOTIFTAPOX1 | | site | 374 | (+) | ATATT | S000098 |
| SEF4MOTIFGM7S | | site | 170 | (-) | RTTTTR | S000103 |
| SP8BFIBSP8BIB | | site | 134 | (+) | TACTATT | S000184 |
| TATABOX2 | | site | 81 | (-) | TATAAAT | S000109 |
| TATABOX3 | | site | 375 | (+) | TATTAAT | S000110 |
| TATABOX4 | | site | 368 | (-) | TATATAA | S000111 |
| TATABOX5 | | site | 238 | (+) | TTATTT | S000203 |
| TATABOX5 | | site | 412 | (+) | TTATTT | S000203 |
| TATABOX5 | | site | 434 | (+) | TTATTT | S000203 |

For more information about the SignalScan Program, please contact Dr Dan S. Prestridge Tele:(612) 625-3744 Advanced Biosciences Computing Center. E-mail:danp@biosci.umn.edu 1479 Gortner Ave. University of Minnesota St. Paul, MN 55108
The TFD data is at the gopher site, gopher://genome-gopher.stanford.edu. For more information about the WebSignalScan service, please contact Meena Sakharkar, meena@biomed.nus.sg, BioInformatics centre, NUS .

Figure 8 (cont'd)

Database Searched: PlantCARE
URL : http://sphinx.rug.ac.be:8080/PlantCARE/

Sequence submitted:

>G564 promoter (-921 to -662) 11/21/00

+ GAAAAGTGAA GAAAACCATG TAATGAAAAC AAAATGGCAC GACAATCAAA AAAAGTTTTC ACGCAAAATT

+ TTCTTCAAAA TTTATAACAT TTTCATGTTG TGTTTGTTTC AAAGCCTAGA AAAACGAAGA GTTACTATTG

+ GTAATGAAAA GCGAAGAAAA CCACATAATA AAAACAAAAT GGCACGACAA TCAAGAAAAA GTTTTCACAC

+ AAAACTTTTT TCAAAATTTA CTATGTTTAT TTCGAAATTT AGAAAAACGA AGAGTTATTA TTAGTAATGA

+ AAAGCGAAGA AAACTACGTA ATAAAAAACA AAATGGCACG ACAATAAAAA AAGTTTTCAC GCAAAATTTT

+ CTTGGTGCGC AGAAAGTTAT ATATATTAAT TAATTAATTT TCATTTACTT TTTTCCCTTT TTATTTTAAA

+ GTTAAATTAT TATTATTTTC ATTTAAAA

- CTTTTCACTT CTTTTGGTAC ATTACTTTTG TTTTACCGTG CTGTTAGTTT TTTTGAAAAG TGCGTTTTAA

- AAGAAGTTTT AAATATTGTA AAAGTACAAC ACAAACAAAG TTTCGGATCT TTTTGCTTCT CAATGATAAC

- CATTACTTTT CGCTTCTTTT GGTGTATTAT TTTTGTTTTA CCGTGCTGTT AGTTCTTTTT CAAAAGTGTG

- TTTTGAAAAA AGTTTTAAAT GATACAAATA AAGCTTTAAA TCTTTTTGCT TCTCAATAAT AATCATTACT

- TTTCGCTTCT TTTGATGCAT TATTTTTTGT TTTACCGTGC TGTTATTTTT TTCAAAAGTG CGTTTTAAAA

- GAACCACGCG TCTTTCAATA TATATAATTA ATTAATTAAA AGTAAATGAA AAAAGGGAAA AATAAAATTT

- CAATTTAATA ATAATAAAAG TAAATTTT

3-AF1_binding_sit

| Site Name | Organism | Position | Strand | Core simil. | Matrix simil | sequence |
|---|---|---|---|---|---|---|
| 3-AF1_binding_sit | ST | 260 | + | 1.000 | 0.860 | AAGAgttatt |

Function:

AAGAA-motif

| Site Name | Organism | Position | Strand | Core simil. | Matrix simil | sequence |
|---|---|---|---|---|---|---|
| AAGAA-motif | Avena sativa | 6 | + | 1.000 | 0.903 | gtgAAGAa |
| AAGAA-motif | Avena sativa | 151 | + | 1.000 | 0.870 | gcgAAGAa |
| AAGAA-motif | Avena sativa | 284 | + | 1.000 | 0.870 | gcgAAGAa |

Function:

ABRE

Figure 8 (cont'd)

| Site Name | Organism | Position | Strand | Core simil. | Matrix simil | sequence |
|---|---|---|---|---|---|---|
| ABRE | Hordeum vulgare | 293 | + | 1.000 | 0.854 | actACGTaat |

Function: cis-acting element involved in the abscisic acid responsiveness

ACE

| Site Name | Organism | Position | Strand | Core simil. | Matrix simil | sequence |
|---|---|---|---|---|---|---|
| ACE | Petroselinum crispum | 293 | + | 1.000 | 0.908 | actACGTaat |

Function: cis-acting element involved in light responsiveness

AE-box

| Site Name | Organism | Position | Strand | Core simil. | Matrix simil | sequence |
|---|---|---|---|---|---|---|
| AE-box | Arabidopsis thaliana | 67 | - | 1.000 | 0.852 | AGAAaatt |
| AE-box | Arabidopsis thaliana | 345 | - | 1.000 | 0.852 | AGAAaatt |
| AE-box | Arabidopsis thaliana | 361 | + | 1.000 | 0.852 | AGAAagtt |

Function: part of a module for light response

AT1-motif

| Site Name | Organism | Position | Strand | Core simil. | Matrix simil | sequence |
|---|---|---|---|---|---|---|
| AT1-motif | Solanum tuberosum | 409 | + | 1.000 | 0.859 | ttttATTTaaa |

Function: part of a light responsive module

Box_4

| Site Name | Organism | Position | Strand | Core simil. | Matrix simil | sequence |
|---|---|---|---|---|---|---|
| Box_4 | PC | 375 | + | 1.000 | 1.000 | ATTAat |
| Box_4 | PC | 379 | + | 1.000 | 1.000 | ATTAat |
| Box_4 | PC | 383 | - | 1.000 | 1.000 | ATTAat |

Function:

Box_I

| Site Name | Organism | Position | Strand | Core simil. | Matrix simil | sequence |
|---|---|---|---|---|---|---|
| Box_I | PS | 107 | + | 1.000 | 1.000 | TTTCaaa |
| Box_I | PS | 203 | + | 1.000 | 0.857 | TTTCaca |
| Box_I | PS | 219 | + | 1.000 | 1.000 | TTTCaaa |
| Box_I | PS | 240 | + | 1.000 | 0.857 | TTTCgaa |
| Box_I | PS | 241 | - | 1.000 | 0.857 | TTTCgaa |
| Box_I | PS | 249 | - | 1.000 | 0.857 | TTTCtaa |

Figure 8 (cont'd)

Function:

Box_II

| Site Name | Organism | Position | Strand | Core simil. | Matrix simil | sequence |
|---|---|---|---|---|---|---|
| Box_II | ST | 139 | + | 1.000 | 0.889 | TGGTaatga |
| Box_II | AT | 161 | + | 1.000 | 0.954 | CCACat_aat |

Function:

CAAT-box

| Site Name | Organism | Position | Strand | Core simil. | Matrix simil | sequence |
|---|---|---|---|---|---|---|
| CAAT-box | Hordeum vulgare | 43 | + | 1.000 | 1.000 | CAAT |
| CAAT-box | Arabidopsis thaliana | 137 | - | 1.000 | 1.000 | aCCAAt |
| CAAT-box | Hordeum vulgare | 188 | + | 1.000 | 1.000 | CAAT |
| CAAT-box | Hordeum vulgare | 322 | + | 1.000 | 1.000 | CAAT |
| CAAT-box | Arabidopsis thaliana | 351 | - | 1.000 | 0.857 | aCCAAg |

Function: common cis-acting element in promoter and enhancer regions

ERE

| Site Name | Organism | Position | Strand | Core simil. | Matrix simil | sequence |
|---|---|---|---|---|---|---|
| ERE | Dianthus caryophyllus | 239 | + | 1.000 | 0.875 | ATTTcgaa |
| ERE | Dianthus caryophyllus | 241 | - | 1.000 | 0.875 | ATTTcgaa |
| ERE | Dianthus caryophyllus | 413 | + | 1.000 | 0.875 | ATTTaaaa |
| ERE | Dianthus caryophyllus | 441 | + | 1.000 | 0.875 | ATTTaaaa |
| ERE | Dianthus caryophyllus | 442 | - | 1.000 | 0.875 | ATTTtaaa |

Function: ethylene-responsive element

G-box

| Site Name | Organism | Position | Strand | Core simil. | Matrix simil | sequence |
|---|---|---|---|---|---|---|
| G-box | Zea mays | 17 | + | 0.842 | 0.870 | CATGta |
| G-box | Zea mays | 38 | + | 1.000 | 0.903 | CACGac |
| G-box | Zea mays | 94 | + | 0.842 | 0.886 | CATGtt |
| G-box | Zea mays | 183 | + | 1.000 | 0.903 | CACGac |
| G-box | Zea mays | 317 | + | 1.000 | 0.903 | CACGac |

Function: cis-acting regulatory element involved in light responsiveness

GC-repeat

Figure 8 (cont'd)

| Site Name | Organism | Position | Strand | Core simil. | Matrix simil | sequence |
|---|---|---|---|---|---|---|
| GC-repeat Function: ? | Oryza sativa | 351 | - | 1.000 | 1.000 | gCACCaag |

HSE

| Site Name | Organism | Position | Strand | Core simil. | Matrix simil | sequence |
|---|---|---|---|---|---|---|
| HSE | Brassica oleracea | 49 | + | 0.944 | 0.878 | aAAAAagtt |
| HSE | Brassica oleracea | 50 | + | 0.944 | 0.912 | aAAAAgttt |
| HSE | Brassica oleracea | 52 | - | 0.944 | 0.874 | gAAAActtt |
| HSE | Brassica oleracea | 66 | - | 1.000 | 0.978 | aGAAAattt |
| HSE | Brassica oleracea | 77 | - | 0.833 | 0.868 | aTAAAtttt |
| HSE | Brassica oleracea | 87 | - | 1.000 | 0.853 | tGAAAatgt |
| HSE | Brassica oleracea | 196 | + | 0.944 | 0.912 | aAAAAgttt |
| HSE | Brassica oleracea | 198 | - | 0.944 | 0.874 | gAAAActtt |
| HSE | Brassica oleracea | 210 | + | 0.944 | 0.874 | cAAAActtt |
| HSE | Brassica oleracea | 212 | - | 0.944 | 0.912 | aAAAAgttt |
| HSE | Brassica oleracea | 213 | - | 0.944 | 0.878 | aAAAAagtt |
| HSE | Brassica oleracea | 327 | + | 0.944 | 0.878 | aAAAAagtt |
| HSE | Brassica oleracea | 328 | + | 0.944 | 0.912 | aAAAAgttt |
| HSE | Brassica oleracea | 330 | - | 0.944 | 0.874 | gAAAActtt |
| HSE | Brassica oleracea | 344 | - | 1.000 | 0.978 | aGAAAattt |
| HSE | Brassica oleracea | 361 | + | 1.000 | 0.888 | aGAAAgtta |

Figure 8 (cont'd)

| | | | | | | | |
|---|---|---|---|---|---|---|---|
| HSE | Brassica oleracea | 385 | | 1.000 | 0.853 | tGAAAatta | |

Function: cis-acting element involved in heat stress responsiveness

I-box

| Site Name | Organism | Position | Strand | Core simil. | Matrix simil | sequence |
|---|---|---|---|---|---|---|
| I-box | Pisum sativum | 93 | - | 0.857 | 0.883 | aACATga |
| I-box | Pisum sativum | 162 | + | 0.857 | 0.883 | cACATaa |
| I-box | Solanum tuberosum | 163 | - | 1.000 | 1.000 | tATTAtgt |
| I-box | Pisum sativum | 237 | - | 0.857 | 0.941 | gAAATaa |
| I-box | Pisum sativum | 367 | - | 1.000 | 1.000 | tATATaa |
| I-box | Pisum sativum | 372 | + | 1.000 | 0.941 | tATATta |
| I-box | Pisum sativum | 391 | - | 0.857 | 0.941 | tAAATga |
| I-box | Pisum sativum | 411 | - | 0.857 | 0.883 | aAAATaa |
| I-box | Pisum sativum | 423 | + | 0.857 | 0.883 | tAAATta |
| I-box | Solanum tuberosum | 424 | - | 1.000 | 0.903 | aATAAttt |
| I-box | Arabidopsis thaliana | 426 | - | 1.000 | 0.863 | aATAAtaat |
| I-box | Arabidopsis thaliana | 429 | - | 1.000 | 0.863 | aATAAtaat |
| I-box | Solanum tuberosum | 431 | + | 1.000 | 0.951 | tATTAttt |
| I-box | Pisum sativum | 433 | - | 0.857 | 0.883 | aAAATaa |
| I-box | Pisum sativum | 439 | - | 0.857 | 0.941 | tAAATga |

Function: part of a light responsive element

P-box

| Site Name | Organism | Position | Strand | Core simil. | Matrix simil | sequence |
|---|---|---|---|---|---|---|
| P-box | Oryza sativa | 406 | + | 1.000 | 0.857 | CCTTttt |

Function: gibberellin-responsive element

Prolamin_box

| Site Name | Organism | Position | Strand | Core simil. | Matrix simil | sequence |
|---|---|---|---|---|---|---|
| Prolamin-box | oryza sativa | 145 | + | 1.000 | 0.913 | tgaAAAGc |
| Prolamin-box | Oryza sativa | 278 | + | 1.000 | 0.913 | tgaAAAGc |

Function: cis-acting regulatory element associated with GCN4

TATA-box

| Site Name | Organism | Position | Strand | Core simil. | Matrix simil | sequence |
|---|---|---|---|---|---|---|
| TATA-box | Daucus carota | 79 | - | 1.000 | 1.000 | TATAaatt |
| TATA-box | Brassica juncea | 80 | - | 1.000 | 1.000 | TATAaat |
| TATA-box | Helianthus annuus | 81 | - | 1.000 | 1.000 | TATAaa |
| TATA-box | Brassica oleracea | 82 | + | 1.000 | 0.908 | tTATAac |
| TATA-box | Brassica napus | 83 | - | 1.000 | 0.892 | gtTATA |
| TATA-box | Oryza sativa | 117 | + | 0.818 | 0.912 | TAGAaaa |
| TATA-box | Oryza sativa | 169 | + | 0.818 | 0.872 | TAAAaac |
| TATA-box | Zea mays | 248 | + | 0.909 | 0.879 | TTTAgaaa |

Figure 8 (cont'd)

| | | | | | | |
|---|---|---|---|---|---|---|
| TATA-box | Oryza sativa | 250 | + | 0.818 | 0.912 | TAGAaaa |
| TATA-box | Oryza sativa | 302 | + | 0.818 | 0.912 | TAAAaaa |
| TATA-box | Oryza sativa | 325 | + | 0.818 | 0.912 | TAAAaaa |
| TATA-box | Daucus carota | 364 | - | 1.000 | 0.863 | TATAactt |
| TATA-box | Brassica juncea | 365 | - | 1.000 | 0.857 | TATAact |
| TATA-box | Zea mays | 366 | - | 1.000 | 0.879 | TATAtaac |
| TATA-box | Oryza sativa | 367 | - | 1.000 | 0.956 | TATAtaa |
| TATA-box | Oryza sativa | 368 | + | 1.000 | 0.929 | TATAtat |
| TATA-box | Oryza sativa | 369 | - | 1.000 | 0.929 | TATAtat |
| TATA-box | Solanum tuberosum | 370 | - | 1.000 | 1.000 | TATAta |
| TATA-box | Glycine max | 372 | + | 1.000 | 0.891 | TATAtt |
| TATA-box | Oryza sativa | 407 | - | 0.818 | 0.872 | TAAAaag |
| TATA-box | Zea mays | 413 | - | 0.909 | 0.879 | TTTAaaat |
| TATA-box | Zea mays | 442 | + | 0.909 | 0.879 | TTTAaaat |

Function: core promoter element around -30 of transcription start

TC-rich_repeats

| Site Name | Organism | Position | Strand | Core simil. | Matrix simil | sequence |
|---|---|---|---|---|---|---|
| TC-rich_repeats | NT | 7 | - | 1.000 | 0.952 | gTTTTcttca |
| TC-rich_repeats | NT | 68 | + | 1.000 | 1.000 | aTTTTcttca |
| TC-rich_repeats | NT | 152 | - | 1.000 | 0.909 | gTTTTcttcg |
| TC-rich_repeats | NT | 191 | - | 1.000 | 0.885 | tTTTTcttga |
| TC-rich_repeats | NT | 248 | - | 1.000 | 0.914 | tTTTTctaaa |
| TC-rich_repeats | NT | 285 | - | 1.000 | 0.909 | gTTTTcttcg |
| TC-rich_repeats | NT | 346 | + | 1.00D | 0.915 | aTTTTcttgg |

Function:

WUN-motif

| Site Name | Organism | Position | Strand | Core simil. | Matrix simil | sequence |
|---|---|---|---|---|---|---|
| WUN-motif | Brassica oleracea | 18 | - | 1.000 | 0.948 | tCATTacat |
| WUN-motif | Brassica oleracea | 139 | - | 1:000 | 1.000 | tCATTacca |
| WUN-motif | Brassica oleracea | 237 | + | 0.857 | 0.948 | tTATTtcga |
| WUN-motif | Brassica oleracea | 242 | - | 1.000 | 1.000 | aAATTtcga |
| WUN-motif | Brassica oleracea | 272 | - | 1.000 | 0.948 | tCATTacta |
| WUN-motif | Brassica oleracea | 296 | - | 0.857 | 0.948 | tTATTacgt |

Function: wound-responsive element

Figure 8 (cont'd)

POLYNUCLEOTIDES USEFUL FOR MODULATING TRANSCRIPTION

This invention was made with Government support under Contract No. DE-FG0397ER20263, awarded by the Department of Energy, and under Grant No. 97353044740, awarded by the U.S. Department of Agriculture. The Government has certain rights in this invention.

In most higher plants, the first division of the zygote is asymmetric giving rise to two daughter cells differing in size and developmental fate (Goldberg, R. B., et al., *Science*, 266:605–614 (1994); Embryology of Angiosperms (Johri, B. M., ed., 1984); Kaplan, D. R., et al., *Plant Cell*, 9:1903–1919 (1997); Laux, T., et al., *Plant Cell*, 9:898–1000 (1997); Embryogenesis in Angiosperms: A Developmental and Experimental Study (Raghavan, V., ed. 1986); West, M. A. L., et al., *Plant Cell*, 5:1361–1369 (1993)). The small terminal, or apical cell, is cytoplasmically dense and differentiates into the embryo proper containing one or two cotyledons and an axis with shoot and root meristems. By contrast, the large, highly-vacuolate basal cell differentiates into the bypophysis and suspensor. The hypophysis contributes to the formation of the root meristem within the embryo proper (van Den Berg, C., et al., *Planta Berlin*, 205:483–491 (1998)). The suspensor, on the other hand, is a terminally-differentiated embryonic region that anchors the embryo proper to the surrounding maternal tissue, serves as conduit for nutrients and growth regulators supporting embryo-proper development, and degenerates by the end of embryogenesis (Natesh, S., et al., Embryology of Angiosperms, (B. M. Johri, ed., 1984) 377–444; Schwartz, B. W., et al., Cellular and Molecular Biology of Plant Seed Development, (B. Vasil, ed. 1997) 53–72,; Walthall, E. D., et al., *Cell Differentiation*, 18:37–44 (1986); Yeung, E. C., et al., Can. J Bot., 57:120–136 (1979); Yeung, E. C., et al., *Plant Cell*, 5:1371–1381 (1993)).

The suspensor provides a novel opportunity to use molecular biology in order to understand how the zygote gives rise to daughter cells with distinct developmental fates. It is highly differentiated and contains cells that are direct clonal descendents of the basal cell and, ultimately the basal region of the egg (Goldberg, R. B., et al., *Science*, 266:605–614 (1994); Schwartz, B. W., et al., Cellular and Molecular Biology of Plant Seed Development, (B. Vasil, ed. 1997) 53–72; Yeung, E. C., et al., *Plant Cell*, 5:1371–1381 (1993)). Fully developed *Arabidopsis* and tobacco suspensors, for example, are only three to four cell divisions removed from the basal cell (Mansfield, S. G., et al., *Canadian Journal of Botany*, 69:461–476 (1991); Soueges, R., *Compt. Rend. Acad. Sci. Paris*, 170:1125–1127 (1920)). It is possible, therefore, that the mechanisms regulating suspensor-specific gene expression are linked directly to the processes specifying the developmental fate of the basal cell. An understanding how suspensor gene expression is regulated should provide insight into the molecular mechanisms specifying the fate of the basal cell.

Scarlet Runner Bean (*Phaseolus coccineus*) suspensors are approximately 100 times larger than the suspensors of either *Arabidopsis* or tobacco (Yeung, E. C., et al., *Plant Cell*, 5:1371–1381 (1993)). Because of their large size, Scarlet Runner Bean suspensors can be microdissected from embryos during the early stages of embryogenesis (e.g., globular stage) and used for cDNA cloning, transcript profiling, and EST sequencing studies in order to identify and investigate suspensor-specific gene sets.

Control of the expression of genes in suspensor cells in plants is useful in the production of plants with a range of desired traits. For example, control of gene expression in suspensor cells can be used to make seedless fruit or to regulate embryo size or shape. These and other advantages are provided by the present application.

SUMMARY OF THE INVENTION

The present invention provides polynucleotides comprising a promoter control element, which comprises 1) a nucleotide sequence at least 50% identical to nucleotides 3321 to 3580 of SEQ ID NO:1, or 2) a nucleotide sequence that hybridizes to nucleotides 3321 to 3580 of SEQ ID NO:1 under a condition establishing a $T_m$ of 20° C. In some embodiments, the isolated polynucleotides of the invention comprise a polynucleotide comprising 1) a nucleotide sequence at least 50% identical to SEQ ID NO:1, or 2) a nucleotide sequence that hybridizes to SEQ ID NO:1 under a condition establishing a $T_m$ of 20° C. In some embodiments, the polynucleotides of the invention comprise nucleotides 3321 to 3580 of SEQ ID NO:1. In some embodiments, the polynucleotides of the invention modulate transcription in a cell. In some embodiments, the polynucleotides of the invention specifically modulate transcription in a plant suspensor cell and/or basal region of a plant embryo.

The present invention also provides expression cassettes comprising a promoter sequence comprising a nucleotide sequence at least 50% identical to nucleotides 3321 to 3580 of SEQ ID NO:1 and a promoter polynucleotide with at least basal promoter activity, which promoter polynucleotide is operably linked to a heterologous polynucleotide, wherein when the expression cassette is inserted into a plant, the heterologous polynucleotide is specifically expressed in a suspensor cell and/or basal region of a plant embryo.

The present invention also provides polynucleotides comprising 1) a nucleotide sequence at least 50% identical to SEQ ID NO:1 or nucleotides 1–3154 or SEQ ID NO:6, or 2) a nucleotide sequence that hybridizes to SEQ ID NO:1 or nucleotides 1–3154 or SEQ ID NO:6 under a condition establishing a $T_m$ of 20° C. In some embodiments, the isolated polynucleotides further comprise a G654 or C541 polynucleotide operably linked to the promoter. Examples of such polynucleotides include SEQ ID NO:2 and SEQ ID NO:6. Alternatively, the invention provides for a heterologous polynucleotide operably linked to a promoter. In some embodiments, the polynucleotides of the invention comprise a promoter that modulates transcription in a cell. In some embodiments, the polynucleotides of the invention specifically modulate transcription in a plant suspensor cell and/or basal region of a plant embryo.

The present invention also provides for vectors comprising the above-referenced promoter operably linked to a heterologous polynucleotide. For instance, in some embodiments, the promoter is SEQ ID NO:1 or nucleotides 1 to 3154 of SEQ ID NO:6.

The present invention also provides for a host cell comprising the above-referenced promoters. For instance, in some embodiments, the promoter is SEQ ID NO:1 or nucleotides 1 to 3154 of SEQ ID NO:6. In some embodiments, the host cell comprises a vector comprising the promoters of the invention operably linked to a heterologous nucleic acid.

The invention also provides for plants comprising a promoter comprising 1) a nucleotide sequence at least 50% identical to SEQ ID NO:1 or nucleotides 1–3154 or SEQ ID NO:6, or 2) a nucleotide sequence that hybridizes to SEQ ID NO:1 or nucleotides 1–3154 or SEQ ID NO:6 under a condition establishing a $T_m$ of 20° C., wherein the promoter is operably linked to a heterologous polynucleotide. For instance, in some embodiments, the promoter is SEQ ID NO:1 or nucleotides 1 to 3154 of SEQ ID NO:6. In some embodiments, the plant comprises a vector comprising the promoters of the invention operably linked to a heterologous nucleic acid.

The invention also provides methods of modulating transcription in a suspensor cell comprising introducing into the plant an expression cassette comprising a promoter comprising 1) a nucleotide sequence at least 50% identical to SEQ ID NO:1 or nucleotides 1–3154 or SEQ ID NO:6, or 2) a nucleotide sequence that hybridizes to SEQ ID NO:1 or nucleotides 1–3154 or SEQ ID NO:6 under a condition establishing a $T_m$ of 20° C. For instance, in some embodiments, the promoter is SEQ ID NO:1 or nucleotides 1 to 3154 of SEQ ID NO:6. In some embodiments, a G654 or C541 polynucleotide is operably linked to the promoter. In some embodiments, the promoter is operably linked to a heterologous polynucleotide. In some embodiments, the promoter is operably linked to the heterologous polynucleotide in an antisense orientation.

The present invention also provides isolated nucleic acids comprising a polynucleotide sequence, or complement thereof, encoding a G654 polypeptide at least 50% identical to SEQ ID NO:3 or a C541 polypeptide at least 50% identical to SEQ ID NO:7. In some embodiments, the G654 polypeptide is SEQ ID NO:3. In some embodiments, the C541 polypeptide is SEQ ID NO:7. In some embodiments, the polynucleotide is operably linked to a promoter. For example, the promoter can be a constitutive promoter. In some embodiments, the polynucleotide is linked to the promoter in an antisense orientation.

The invention also provides an expression cassette comprising a promoter operably linked to a heterologous polynucleotide, or complement thereof, encoding a G654 or C541 polypeptide at least 50% identical to SEQ ID NO:3 or SEQ ID NO:7, respectively. In some embodiments, the G654 polynucleotide comprises nucleotides 4242 to 4901 of SEQ ID NO:2. In some embodiments, the C541 polynucleotide comprises nucleotides 3155 to 3552 of SEQ ID NO:6. In some embodiments, the polynucleotide is operably linked to a promoter. For example, the promoter can be a constitutive promoter. In some embodiments, the polynucleotide is linked to the promoter in an antisense orientation.

The present invention also provides for host cells and transgenic plants comprising an exogenous nucleic acid comprising a polynucleotide, or complement thereof, encoding a G654 polypeptide at least 50% identical to SEQ ID NO:3 or a C541 polypeptide at least 50% identical to SEQ ID NO:7.

The present invention also provides for isolated polypeptides comprising an amino acid sequence at least 50% identical to SEQ ID NO:3 or SEQ ID NO:7. The invention also provides for antibodies capable of binding the isolated polypeptides.

The invention also provides methods of introducing an isolated polynucleotide into a host cell. The method comprises providing an isolated polynucleotide that comprises 1) a nucleotide sequence at least 50% identical to SEQ ID NO:1 or nucleotides 1–3154 or SEQ ID NO:6, or 2) a nucleotide sequence that hybridizes to SEQ ID NO:1 or nucleotides 1–3154 or SEQ ID NO:6 under a condition establishing a $T_m$ of 20° C. The method also provides contacting the polynucleotide with the host cell under conditions that permit insertion of the polynucleotide into the host cell.

The invention also provides methods of detecting a polynucleotide in a sample. The methods comprise providing a polynucleotide that comprises 1) a nucleotide sequence at least 50% identical to SEQ ID NO:1 or nucleotides 1–3154 or SEQ ID NO:6, or 2) a nucleotide sequence that hybridizes to SEQ ID NO:1 or nucleotides 1–3154 or SEQ ID NO:6 under a condition establishing a $T_m$ of 20° C. The method also comprises contacting the polynucleotide with a sample under conditions that permit a comparison of the sequence of the polynucleotide with a sequence of DNA in the sample and analyzing the result of the comparison. In some embodiments, the polynucleotide and the sample are contacted under conditions that permit formation of a duplex between complementary nucleic acid sequences.

The present invention also provides polynucleotides comprising SEQ ID NO:10 or SEQ ID NO:11. In some embodiments, the polynucleotides of the invention comprise an expression cassette comprising a promoter sequence comprising SEQ ID NO:10 or SEQ ID NO:11 and a promoter polynucleotide with at least basal promoter activity, which promoter polynucleotide is operably linked to a heterologous polynucleotide, wherein when the expression cassette is inserted into a plant, the heterologous polynucleotide is specifically expressed in a suspensor cell and/or basal region of a plant embryo.

The invention also provides methods of constructing a promoter that specifically induces transcription in a plant suspensor cell and/or basal region of a plant embryo, the method comprising (i) providing a promoter polynucleotide capable of at least basal promoter activity in a plant; (ii) inserting a nucleic acid comprising SEQ ID NO: 10 or SEQ ID NO:11 within or adjoining the promoter polynucleotide, thereby constructing a test promoter; and (iii) assaying the test promoter to determine whether the test promoter specifically initiates transcription in a suspensor cell and/or basal region of a plant embryo. In some embodiments, the nucleic acid is SEQ ID NO:10 or SEQ ID NO:11.

Definitions

The term "basal promoter activity" refers to the ability of a polynucleotide sequence to initiate transcription of an operably linked polynucleotide. Typically, basal activity will provide a low level of constitutive expression that is not inducible under most conditions or that is not cell-specific under most conditions. A basal promoter typically comprises a TATA box and transcriptional start sequence, but does not contain additional stimulatory and repressive elements. An exemplary plant minimal promoter is positions −50 to +8 of the 35S CaMV promoter.

The term "basal region of a plant embryo" refers to the basal cell, i.e., the cell of a two-celled embryo that contacts the suspensor cell. The "basal region" also encompasses derivative or descendent cells of the basal cell.

The term "chimeric" is used to describe polynucleotides or genes, as defined supra, or constructs wherein at least two of the elements of the polynucleotide or gene or construct, such as the promoter and the polynucleotide to be transcribed and/or other regulatory sequences and/or filler sequences and/or complements thereof, are heterologous to each other.

Promoters referred to herein as "constitutive promoters" actively promote transcription under most, but not necessarily all, environmental conditions and states of development or cell differentiation. Examples of constitutive promoters include the cauliflower mosaic virus (CaMV) 35S transcript initiation region and the 1' or 2' promoter derived from T-DNA of *Agrobacterium tumefaciens*, and other transcription initiation regions from various plant genes, such as the maize ubiquitin-1 promoter, known to those of skill.

"Domains" are fingerprints or signatures that can be used to characterize protein families and/or parts of proteins. Such fingerprints or signatures can comprise conserved (1) primary sequence, (2) secondary structure, and/or (3) three-dimensional conformation. A similar analysis can be applied to polynucleotides. Generally, each domain has been associated with either a conserved primary sequence or a sequence motif. Generally these conserved primary sequence motifs have been correlated with specific in vitro and/or in vivo activities. A domain can be any length, including the entirety of the polynucleotide to be transcribed. Examples of domains include, without limitation, AP2, helicase, homeobox, zinc finger, etc.

The term "endogenous," within the context of the current invention refers to any polynucleotide, polypeptide or protein sequence which is a natural part of a cell or organisms regenerated from said cell.

An "enhancer" is a DNA regulatory element that can increase the steady state level of a transcript, usually by increasing the rate of transcription initiation. Enhancers usually exert their effect regardless of the distance, upstream or downstream location, or orientation of the enhancer relative to the start site of transcription. In contrast, a "suppressor" is a corresponding DNA regulatory element that decreases the steady state level of a transcript, again usually by affecting the rate of transcription initiation. The essential activity of enhancer and suppressor elements is to bind a protein factor(s). Such binding can be assayed, for example, by methods described below. The binding is typically in a manner that influences the steady state level of a transcript in a cell or in an in vitro transcription extract.

As referred to within, "exogenous" is any polynucleotide, polypeptide or protein sequence, whether chimeric or not, that is introduced into the genome of a host cell or organism regenerated from said host cell by any means other than by a sexual cross. Examples of means by which this can be accomplished are described below, and include *Agrobacterium*-mediated transformation (of dicots—e.g. Salomon et al. *EMBO J.* 3:141 (1984); Herrera-Estrella et al., *EMBO J.* 2:987 (1983); of monocots, representative papers are those by Escudero et al., *Plant J.* 10:355 (1996), Ishida et al., *Nature Biotechnology* 14:745 (1996), May et al., *Bio/Technology* 13:486 (1995)), biolistic methods (Armaleo et al., *Current Genetics* 17:97 1990)), electroporation, in planta techniques, and the like. Such a plant containing the exogenous nucleic acid is referred to here as a $T_0$ for the primary transgenic plant and $T_1$ for the first generation. The term "exogenous" as used herein is also intended to encompass inserting a naturally found element into a non-naturally found location.

An "expression cassette" refers to a nucleic acid construct, which when introduced into a host cell, results in transcription and/or translation of an RNA or polypeptide, respectively. Antisense or sense constructs that are not or cannot be translated are expressly included by this definition.

The term "gene," as used in the context of the current invention, encompasses all regulatory and coding sequence contiguously associated with a single hereditary unit with a genetic function (see FIG. 1). Genes can include non-coding sequences that modulate the genetic function that include, but are not limited to, those that specify polyadenylation, transcriptional regulation, DNA conformation, chromatin conformation, extent and position of base methylation and binding sites of proteins that control all of these. Genes encoding proteins are comprised of "exons" (coding sequences), which may be interrupted by "introns" (non-coding sequences). In some instances complexes of a plurality of protein or nucleic acids or other molecules, or of any two of the above, may be required for a gene's function. On the other hand, a gene's genetic function may require only RNA expression or protein production, or may only require binding of proteins and/or nucleic acids without associated expression. In certain cases, genes adjacent to one another may share sequence in such a way that one gene will overlap the other. A gene can be found within the genome of an organism, in an artificial chromosome, in a plasmid, in any other sort of vector, or as a separate isolated entity.

A "G564 polynucleotide" is a nucleic acid sequence or subsequence that encodes a polypeptide with substantial identity (as defined below) to SEQ ID NO:3 or SEQ ID NO:5. Alternatively, a G564 polynucleotide includes polynucleotide sequences that are substantially identical to SEQ ID NO:1, SEQ ID NO:2, or SEQ ID NO:4 or that hybridize to SEQ ID NO:1, SEQ ID NO:2, or SEQ ID NO:4 under defined conditions.

A "promoter from a G564 gene" or "G564 promoter" will typically be about 500 to about 5000 nucleotides in length, usually from about 2500 to 4000. Exemplary promoter sequences are shown as SEQ ID NO:1 or nucleotides 1–4242 of SEQ ID NO:2. A G564 promoter can also be identified by its ability to direct expression in suspensor cells.

"Increased or enhanced G564 activity or expression of the G564 gene" refers to an augmented change in G564 activity. Examples of such increased activity or expression include the following. G564 activity or expression of the G564 gene is increased above the level of that in wild-type, non-transgenic control plants (i.e. the quantity of G564 activity or expression of the G564 gene is increased). G564 activity or expression of the G564 gene is in an organ, tissue or cell where it is not normally detected in wild-type, non-transgenic control plants (i.e. spatial distribution of G564 activity or expression of the G564 gene is increased). G564 activity or expression is increased when G564 activity or expression of the G564 gene is present in an organ, tissue or cell for a longer period than in a wild-type, non-transgenic controls (i.e. duration of G564 activity or expression of the G564 gene is increased).

A "C541 polynucleotide" is a nucleic acid sequence or subsequence that encodes a polypeptide with substantial identity (as defined below) to SEQ ID NO:7 or SEQ ID NO:9. Alternatively, a C541 polynucleotide includes polynucleotide sequences that are substantially identical to SEQ ID NO:6, or SEQ ID NO:8 or that hybridize to SEQ ID NO:6 or SEQ ID NO:8 under defined conditions.

A "promoter from a C541 gene" or "C541 promoter" will typically be about 500 to about 5000 nucleotides in length, usually from about 2500 to 4000. Exemplary promoter sequences are shown as nucleotides 1–3154 of SEQ ID NO:6 or nucleotides 1–1609 of SEQ ID NO:8. A C541 promoter can also be identified by its ability to direct expression in suspensor cells.

"Increased or enhanced C541 activity or expression of the C541 gene" refers to an augmented change in C541 activity. Examples of such increased activity or expression include the following. C541 activity or expression of the C541 gene is increased above the level of that in wild-type, non-transgenic control plants (i.e. the quantity of C541 activity or expression of the C541 gene is increased). C541 activity or expression of the C541 gene is in an organ, tissue or cell where it is not normally detected in wild-type, non-transgenic control plants (i.e. spatial distribution of C541 activity or expression of the C541 gene is increased). C541 activity or expression is increased when C541 activity or expression of the C541 gene is present in an organ, tissue or cell for a longer period than in a wild-type, non-transgenic controls (i.e. duration of C541 activity or expression of the C541 gene is increased).

"Inserting a first polynucleotide within or adjoining" a second polynucleotide is discussed below. "Inserting a first polynucleotide within a second polynucleotide" refers to manipulating or constructing a first and second polynucleotide such that the first polynucleotide interrupts the second polynucleotide (e.g., the first polynucleotide is inserted between the 5' end and the 3' end of the second polynucleotide). "Inserting a first polynucleotide adjoining a second polynucleotide" refers to manipulating or constructing a polynucleotide such that the first and second polynucleotides are linked, i.e., the first polynucleotide is adjacent to the second polynucleotide. Of course, one of skill in the art will recognize that the first and the second polynucleotide can be linked in either orientations (e.g., 1→2 or 2→1) or can be linked via a polynucleotide spacer. In the context of promoter sequences, polynucleotides comprising TATA boxes and other basal promoter elements are typically at the 3' end of a promoter and can be operably linked at their 3' end to a polynucleotide that is to be transcribed. Moreover, in some embodiments, promoter sequences comprise fewer than 10,000 base pairs, more typically fewer than 5,000 base pairs, sometimes fewer than 3,000, 1,000 or 500 base pairs. However, as noted elsewhere within this application, enhancer elements can function independently of their distance from a basal promoter. Therefore, in some embodiments, the active elements of a promoter can be separated by more than 10,000 base pairs.

"Heterologous sequences" are those that are not operatively linked or are not contiguous to each other in nature. For example, a promoter from corn is considered heterologous to an *Arabidopsis* coding region sequence. Also, a promoter from a gene encoding a growth factor from maize is considered heterologous to a sequence encoding the maize receptor for the growth factor. Regulatory element sequences, such as UTRs or 3' end termination sequences that do not originate in nature from the same gene as the coding sequence originates from, are considered heterologous to said coding sequence. Elements operatively linked in nature and contiguous to each other are not heterologous to each other.

In the current invention, a "homologous" gene or polynucleotide or polypeptide refers to a gene or polynucleotide or polypeptide that shares sequence similarity with the gene or polynucleotide or polypeptide of interest. This similarity may be in only a fragment of the sequence and often represents a functional domain such as, examples including without limitation a DNA binding domain or a domain with tyrosine kinase activity. The functional activities of homologous polynucleotide are not necessarily the same.

An "inducible promoter" in the context of the current invention refers to a promoter, the activity of which is influenced by certain conditions, such as light, temperature, chemical concentration, protein concentration, conditions in an organism, cell, or organelle, etc. A typical example of an inducible promoter, which can be utilized with the polynucleotides of the present invention, is PARSK1, the promoter from an *Arabidopsis* gene encoding a serine-threonine kinase enzyme, and which promoter is induced by dehydration, abscissic acid and sodium chloride (Wang and Goodman, Plant J. 8:37 (1995)). Examples of environmental conditions that may affect transcription by inducible promoters include anaerobic conditions, elevated temperature, the presence or absence of a nutrient or other chemical compound or the presence of light.

As used herein, the phrase "modulate transcription" describes the biological activity of a promoter sequence or promoter control element. Such modulation includes, without limitation, includes up- and down-regulation of initiation of transcription, rate of transcription, and/or transcription levels.

In the current invention, "mutant" refers to a heritable change in nucleotide sequence at a specific location. Mutant genes of the current invention may or may not have an associated identifiable phenotype.

An "operable linkage" is a linkage in which a promoter sequence or promoter control element is connected to a polynucleotide sequence (or sequences) in such a way as to place transcription of the polynucleotide sequence under the influence or control of the promoter or promoter control element. Two DNA sequences (such as a polynucleotide to be transcribed and a promoter sequence linked to the 5' end of the polynucleotide to be transcribed) are said to be operably linked if induction of promoter function results in the transcription of mRNA encoding the polynucleotide and if the nature of the linkage between the two DNA sequences does not (1) result in the introduction of a frame-shift mutation, (2) interfere with the ability of the promoter sequence to direct the expression of the protein, antisense RNA or ribozyme, or (3) interfere with the ability of the DNA template to be transcribed. Thus, a promoter sequence would be operably linked to a polynucleotide sequence if the promoter was capable of effecting transcription of that polynucleotide sequence.

"Orthologous" is a term used herein to describe a relationship between two or more polynucleotides or proteins. Two polynucleotides or proteins are "orthologous" to one another if they serve a similar function in different organisms. In general, orthologous polynucleotides or proteins will have similar catalytic functions (when they encode enzymes) or will serve similar structural functions (when they encode proteins or RNA that form part of the ultra-structure of a cell).

"Percentage of sequence identity," as used herein, is determined by comparing two optimally aligned sequences over a comparison window, where the fragment of the polynucleotide or amino acid sequence in the comparison window may comprise additions or deletions (e.g., gaps or overhangs) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman *Add. APL. Math.* 2:482 (1981), by the homology alignment algorithm of Needleman and Wunsch *J. Mol. Biol.* 48:443 (1970), by the search for similarity method of Pearson and Lipman *Proc. Natl. Acad. Sci. (USA)* 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by inspection. Given that two sequences have been identified for comparison, GAP and BESTFIT are preferably employed to determine their optimal alignment. Typically, the default values of 5.00 for gap weight and 0.30 for gap weight length are used.

A "plant promoter" is a promoter capable of initiating transcription in plant cells and can modulate transcription of a polynucleotide. Such promoters need not be of plant origin. For example, promoters derived from plant viruses, such as the CaMV35S promoter or from *Agrobacterium tumefaciens* such as the T-DNA promoters, can be plant promoters. A typical example of a plant promoter of plant origin is the maize ubiquitin-1 (ubi-1) promoter known to those of skill.

The term "plant tissue" includes differentiated and undifferentiated tissues or plants, including but not limited to roots, stems, shoots, cotyledons, epicotyl, hypocotyl, leaves, pollen, seeds, tumor tissue and various forms of cells and culture such as single cells, protoplast, embryos, basal and apical cells, suspensor cells and callus tissue. The plant tissue may be in plants or in organ, tissue or cell culture.

"Preferential transcription" is defined as transcription that occurs in a particular pattern of cell types or developmental times or in response to specific stimuli or combination thereof. Non-limiting examples of preferential transcription include: high transcript levels of a desired sequence in suspensor cells; detectable transcript levels of a desired sequence in certain cell types during embryogenesis; and low transcript levels of a desired sequence under drought conditions. Such preferential transcription can be determined by measuring initiation, rate, and/or levels of transcription.

A "promoter" is a DNA sequence that directs the transcription of a polynucleotide. Typically a promoter is located in the 5' region of a polynucleotide to be transcribed, proximal to the transcriptional start site of such polynucleotide. More typically, promoters are defined as the region upstream of the first exon; more typically, as a region upstream of the first of multiple transcription start sites; more typically, as the region downstream of the preceding gene and upstream of the first of multiple transcription start sites; more typically, the region downstream of the polyA signal and upstream of the first of multiple transcription start sites; even more typically, about 3,000 nucleotides upstream of the ATG of the first exon; even more typically, 2,000 nucleotides upstream of the first of multiple transcription start sites. The promoters of the invention comprise at least a core promoter as defined below. Additionally, the promoter may also include at least one control element such as an upstream element. Such elements include UARs and optionally, other DNA sequences that affect transcription of a polynucleotide such as a synthetic upstream element.

The term "promoter control element" as used herein describes elements that influence the activity of the promoter. Promoter control elements include transcriptional regulatory sequence determinants such as, but not limited to, enhancers, scaffold/matrix attachment regions, TATA boxes, transcription start locus control regions, UARs, URRs, other transcription factor binding sites and inverted repeats. Exemplary promoter control elements include, e.g., SEQ ID NO:10 and SEQ ID NO:11.

The term "public sequence," as used in the context of the instant application, refers to any sequence that has been deposited in a publicly accessible database prior to the filing date of the present application. This term encompasses both amino acid and nucleotide sequences. Such sequences are publicly accessible, for example, on the BLAST databases on the NCBI FTP web site (accessible at ncbi.nlm.gov/blast). The database at the NCBI GTP site utilizes "gi" numbers assigned by NCBI as a unique identifier for each sequence in the databases, thereby providing a non-redundant database for sequence from various databases, including GenBank, EMBL, DBBJ, (DNA Database of Japan) and PDB (Brookhaven Protein Data Bank).

The term "regulatory sequence," as used in the current invention, refers to any nucleotide sequence that influences transcription or translation initiation and rate, or stability and/or mobility of a transcript or polypeptide product. Regulatory sequences include, but are not limited to, promoters, promoter control elements, protein binding sequences, 5' and 3' UTRs, transcriptional start sites, termination sequences, polyadenylation sequences, introns, certain sequences within amino acid coding sequences such as secretory signals, protease cleavage sites, etc.

"Related sequences" refer to either a polypeptide or a nucleotide sequence that exhibits some degree of sequence similarity with a reference sequence.

The term "substantial identity" of polynucleotide sequences means that a polynucleotide comprises a sequence that has at least 25% sequence identity. Alternatively, percent identity can be any integer from 25% to 100%. More preferred embodiments include at least: 25%, 30%, 35%, 40%, 45%, 50%, 55%, 60%, 65%, 70%, 75%, 80%, 85%, 90%, 95%, or 99%. compared to a reference sequence using the programs described herein; preferably BLAST using standard parameters, as described below. For instance, promoter sequences of the invention sequences of the invention include nucleic acid sequences that have substantial identity to SEQ ID NO:1 or other sequences of the invention such as nucleotides 1–4582 of SEQ ID NO:4, nucleotides 1–3154 of SEQ ID NO:6 or nucleotides 1–1609 of SEQ ID NO:8. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 40%. Preferred percent identity of polypeptides can be any integer from 40% to 100%. More preferred embodiments include at least 60%, 65%, 70%, 75%, 80%, 85%, 90%, 95%, or 99%. Most preferred embodiments include 67%, 68%, 69%, 70%, 71%, 72%, 73%, 74% and 75%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

In the context of the current invention, "specific promoters" refers to a subset of promoters that have a high preference for modulating transcript levels in a specific tissue or organ or cell and/or at a specific time during development of an organism, i.e., that are "specifically initiated" or "specifically modulated" in a specific tissue or at a specific developmental time. By "high preference" is meant at least 3-fold, preferably 5-fold, more preferably at least 10-fold still more preferably at least 20-fold, 50-fold or 100-fold increase in transcript levels under the specific condition and/or a specific tissue over the transcription under any other reference condition and/or in any other reference tissue considered. Examples of tissue-specific promoters under developmental control include promoters that initiate transcription only in certain tissues or organs, such as suspensor cell, root, ovule, fruit, seeds, or flowers. See also "Preferential transcription".

"Stringency" as used herein is a function of probe length, probe composition (G+C content), and salt concentration, organic solvent concentration, and temperature of hybridization or wash conditions. Stringency is typically compared by the parameter $T_m$, which is the temperature at which 50% of the complementary molecules in the hybridization are hybridized, in terms of a temperature differential from $T_m$. High stringency conditions are those providing a condition of $T_m$ minus 5° C. to $T_m$ minus 10° C. Medium or moderate stringency conditions are those providing $T_m$-minus 20° C. to $T_m$ minus 29° C. Low stringency conditions are those providing a condition of $T_m$ minus 40° C. to $T_m$ minus 48° C. The relationship of hybridization conditions to $T_m$ (in ° C.) is expressed in the mathematical equation $$T_m = 81.5 - 16.6(\log_{10}[Na^+]) + 0.41(\%G+C) - (600/N) \quad (1)$$

where N is the length of the probe. This equation works well for probes 14 to 70 nucleotides in length that are identical to the target sequence. The equation below for $T_m$ of DNA-DNA hybrids is useful for probes in the range of 50 to greater than 500 nucleotides, and for conditions that include an organic solvent (formamide).

$$T_m = 81.5 + 16.6 \log \{[Na^+]/(1+0.7[Na^+])\} + 0.41(\%G+C) - 500/L$$
$$0.63(\%formamide) \quad (2)$$

where L is the length of the probe in the hybrid. (P. Tijessen, "Hybridization with Nucleic Acid Probes" in Laboratory Techniques in Biochemistry and Molecular Biology, (P.C. van der Vliet, ed. 1993)). The $T_m$ of equation (2) is affected by the nature of the hybrid; for DNA-RNA hybrids $T_m$ is 10–15° C. higher than calculated, for RNA-RNA hybrids $T_m$ is 20–25° C. higher. Because the $T_m$ decreases about 1° C. for each 1% decrease in homology when a long probe is used (Bonner et al., *J. Mol. Biol.* 81:123 (1973)), stringency conditions can be adjusted to favor detection of identical genes or related family members.

Equation (2) is derived assuming equilibrium and therefore, hybridizations according to the present invention are most preferably performed under conditions of probe excess and for sufficient time to achieve equilibrium. The time required to reach equilibrium can be shortened by inclusion of a hybridization accelerator such as dextran sulfate or another high volume polymer in the hybridization buffer.

Stringency can be controlled during the hybridization reaction or after hybridization has occurred by altering the salt and temperature conditions of the wash solutions used. The formulas shown above are equally valid when used to compute the stringency of a wash solution. Preferred wash solution stringencies lie within the ranges stated above; high stringency is 5–8° C. below $T_m$, medium or moderate stringency is 26–29° C. below $T_m$ and low stringency is 45–48° C. below $T_m$. Hybridization conditions include those in which the salt concentration is less than about 1.0 M sodium ion, typically about 0.1 to 1.0 M sodium ion concentration (or other salts) at pH 7.0 to 8.3 and the temperature is at least about 65° C. or about 60° C., more preferably 55° C. and more preferably 50° C.

A composition containing A is "substantially free of" B when at least 85% by weight of the total A+B in the composition is A. Preferably, A comprises at least about 90% by weight of the total of A+B in the composition, more preferably at least about 95% or even 99% by weight. For example, a plant gene can be substantially free of other plant genes. Other examples include, but are not limited to, ligands substantially free of receptors (and vice versa), a growth factor substantially free of other growth factors and a transcription binding factor substantially free of nucleic acids.

"TATA to start" shall mean the distance, in number of nucleotides, between the primary TATA motif and the start of transcription.

A "transgenic plant" is a plant having one or more plant cells that contain at least one exogenous polynucleotide introduced by recombinant nucleic acid methods.

In the context of the present invention, a "translational start site" is usually an ATG or AUG in a transcript, often the first ATG or AUG. A single protein encoding transcript, however, may have multiple translational start sites.

"Transcription start site" is used in the current invention to describe the point at which transcription is initiated. This point is typically located about 25 nucleotides downstream from a TFIID binding site, such as a TATA box. Transcription can initiate at one or more sites within the gene, and a single polynucleotide to be transcribed may have multiple transcriptional start sites, some of which may be specific for transcription in a particular cell-type or tissue or organ. "+1" is stated relative to the transcription start site and indicates the first nucleotide in a transcript.

An "Upstream Activating Region" or "UAR" is a position or orientation dependent nucleic acid element that primarily directs tissue, organ, cell type, or environmental regulation of transcript level, usually by affecting the rate of transcription initiation. Corresponding DNA elements that have a transcription inhibitory effect are called herein "Upstream Repressor Regions" or "URR"s. The essential activity of these elements is to bind a protein factor. Such binding can be assayed by methods described below. The binding is typically in a manner that influences the steady state level of a transcript in a cell or in vitro transcription extract.

An "untranslated region" or "UTR" is any contiguous series of nucleotide bases that is transcribed, but is not translated. A 5' UTR lies between the start site of the transcript and the translation initiation codon and includes the +1 nucleotide. A 3' UTR lies between the translation termination codon and the end of the transcript. UTRs can have particular functions such as increasing mRNA message stability or translation attenuation. Examples of 3' UTRs include, but are not limited to polyadenylation signals and transcription termination sequences.

The term "variant" is used herein to denote a polypeptide or protein or polynucleotide molecule that differs from others of its kind in some way. For example, polypeptide and protein variants can consist of changes in amino acid sequence and/or charge and/or post-translational modifications (such as glycosylation, etc). It will be understood that there may be sequence variations within sequence or fragments used or disclosed in this application. Preferably, variants will be such that the sequences have at least 80%, preferably at least 90%, 95, 97, 98, or 99% sequence identity. Variants preferably measure the primary biological function of the native polypeptide or protein or polynucleotide.

BRIEF DESCRIPTION OF THE DRAWINGS

FIG. 2 displays the nucleotide sequence (SEQ ID NO:2) of genomic DNA comprising the G564 coding sequence (amino acid sequence=SEQ ID NO:3) and promoter region from Scarlet Runner Bean (*Phaseolus coccineus*). The ATG start codon is displayed in bold and underlined nucleotides indicates intron sequences.

FIG. 3 displays the nucleotide sequence (SEQ ID NO:4) of genomic DNA comprising the G564 coding sequence (amino acid sequence=SEQ ID NO:5) and promoter region from *Arabidopsis thaliana*. The ATG start codon is displayed in bold and underlined nucleotides indicates intron sequences.

FIG. 4 displays the nucleotide sequence (SEQ ID NO:6) of genomic DNA comprising the C541 coding sequence (amino acid sequence=SEQ ID NO:7) and promoter region from Scarlet Runner Bean (*Phaseolus coccineus*). The ATG start codon is displayed in bold and underlined nucleotides indicates intron sequences.

FIG. 5 displays the nucleotide sequence (SEQ ID NO:8) of genomic DNA comprising the C541 coding sequence (amino acid sequence=SEQ ID NO:9) and promoter region from *Arabidopsis thaliana*. The ATG start codon is displayed in bold and underlined nucleotides indicates intron sequences.

FIG. 8 identifies a number of promoter control elements (SEQ ID NOS:15–24) found within sequences −921 to −662 of FIG. 2 (SEQ ID NO:13 and 14) FIG. 1.

DETAILED DESCRIPTION OF THE INVENTION

A. Introduction

Figure 1:
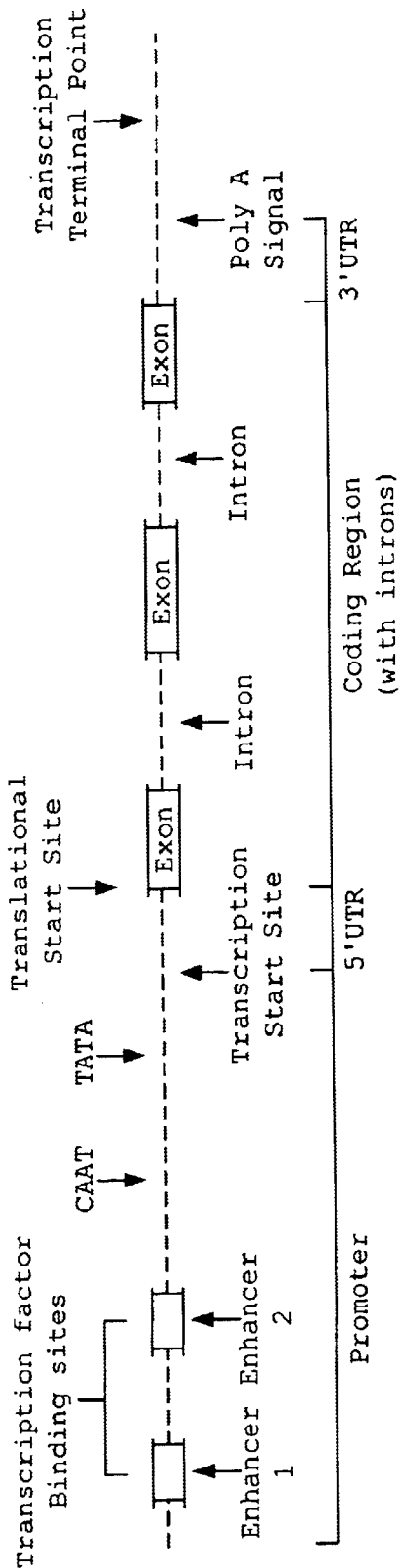
FIG. 1 displays a schematic representation of a gene.

The present invention provides the identification of two Scarlet Runner Bean mRNAs, designated as C541 and G564, that accumulate specifically within the suspensor of globular-stage embryos. At the pre-globular, or four-cell stage, both C541 and G564 mRNAs are present in the two basal cells, but are absent from the two embryo-proper cells. Expression analysis of a chimeric G564/GUS gene in transgenic tobacco embryos showed that the G564 promoter is active specifically within the suspensor during early embryo development.

The present invention provides polynucleotides comprising promoters and promoter control elements which are capable of modulating transcription.

Such promoters and promoter control elements can be used in combination with native or heterologous promoter fragments, control elements or other regulatory sequences to modulate transcription and/or translation.

Specifically, promoters and control elements of the invention can be used to modulate transcription of a desired polynucleotide, which includes without limitation:

(a) antisense;
(b) ribozymes;
(c) coding sequences; or
(d) fragments thereof

The promoter also can modulate transcription in a host genome in cis- or in trans-.

In an organism, such as a plant, the promoters and promoter control elements of the instant invention are useful to produce preferential transcription which results in a desired pattern of transcript levels in a particular cells, tissues, or organs, or under particular conditions.

The present invention also provides new suspensor-specific genes useful in genetically engineering plants. Suspensor-specific promoter sequences from the genes of the invention can be used, for instance, to ablate embryos to make seedless fruit, e.g., by expressing gene products toxic to the suspensor and/or surrounding cells such as the embryo itself. The suspensor-specific promoters can also be operably linked to growth regulator genes, such as gene products regulating gibberellin production, thereby modulating embryo size, shape and/or rate of development.

B. Identifying and Isolating Promoter Sequences or Structural Polynucleotides of the Invention The exemplary promoters and promoter control elements of the present invention (e.g., SEQ ID NO:1 and fragments thereof) were identified from Scarlet Runner bean (*Phaseolus coccineus*). Additional promoter sequences can be identified as described below. SEQ ID NO:1 and SEQ ID NO:2 includes a promoter region of approximately 4200 base pairs upstream of the ATG start codon.

In addition, the coding sequence of a suspensor-specific gene, designated G564, was identified (e.g., nucleotides 4242 to 4349 and 4513 to 4901 of SEQ ID NO:2). The genus of G564 nucleic acid sequences of the invention includes genes and gene products identified and characterized by analysis using the sequences nucleic acid sequences, nucleotides 4242 to 4349 and 4513 to 4901 of SEQ ID NO:2, as well as nucleotides 4242 to 6986 of SEQ ID NO:2, and protein sequences, including SEQ ID NO:3. G564 sequences of the invention include polypeptide sequences having substantial identify to SEQ ID NO:3. The orthologous *Arabidopsis* G564 polynucleotide was also identified (SEQ ID NO:4).

In addition, a polynucleotide designated C541 was also isolated from Scarlet Runner Bean (SEQ ID NO.6). The orthologous *Arabidopsis* C541 sequence is displayed as SEQ ID NO:8. The respective amino acid sequences encoded by the bean and *Arabidopsis* polynucleotides are SEQ ID NO:7 and SEQ ID NO:9.

The promoter sequences of the invention are useful to modulate transcription of polynucleotides. For example, promoter sequences can be operably linked to a polynucleotide of interest to modulate expression of that polynucleotide in desired tissues. Desired tissues for polynucleotide expression include, e.g, suspensor cells and/or the basal region of a plant embryo, the embryo root meristem as well as the plant root tip and plant root meristem.

Alternatively, promoter sequences of the invention, e.g., SEQ ID NO:1, are useful to modulate expression of polynucleotides in desired plant tissues. In addition, the promoter sequences of the invention can also be introduced into a cell in multiple copies, thereby competing with endogenous promoter sequences for transcription factors. By removing some or all of the transcription factors available for a particular promoter, transcription from those endogenous promoters is modulated.

(1) Cloning Methods

Isolation from genomic libraries of polynucleotides comprising the sequences of the genes, promoters and promoter control elements described in SEQ ID NO:1 and SEQ ID NO:2 or other polynucleotides of the present invention is possible using known techniques.

For example, polymerase chain reaction (PCR) can amplify the desired polynucleotides utilizing primers designed from sequences in SEQ ID NO:1, SEQ ID NO:2, SEQ ID NO:4, SEQ ID NO:6 or SEQ ID NO:8. Polynucleotide libraries comprising genomic sequences can be constructed according to Sambrook et al., Molecular Cloning: A Laboratory Manual, 2$^{nd}$ Ed. (1989), for example.

Other procedures for isolating polynucleotides comprising the polynucleotide sequences of the invention include, without limitation, tail-PCR, and 5' rapid amplification of cDNA ends (RACE). For tail-PCR, see, e.g., Liu et al., *Plant J* 8(3): 457–463 (1995); Liu et al., *Genomics* 25: 674–681 (1995); Liu et al., *Nucl. Acids Res.* 21(14): 3333–3334 (1993); and Zoe et al., *BioTechniques* 27(2): 240–248 (1999); for RACE, see, e.g., PCR Protocols: A Guide to Methods and Applications, (1990) Academic Press, Inc.

(2) Chemical Synthesis

In addition, the genes, promoters and promoter control elements of the invention can be chemically synthesized according to techniques in common use. See, e.g., Beaucage et al., *Tet. Lett.* 22: 1859 (1981) and U.S. Pat. No. 4,668,777.

Such chemical oligonucleotide synthesis can be carried out using commercially available devices, such as, Biosearch 4600 or 8600 DNA synthesizer, by Applied Biosystems, a division of Perkin-Elmer Corp., Foster City, Calif., USA; and Expedite by Perceptive Biosystems, Framingham, Mass., USA.

Synthetic RNA, including natural and/or analog building blocks, can be synthesized on the Biosearch 8600 machines, see above.

Oligonucleotides can be synthesized and then ligated together to construct the desired polynucleotide.

C. Isolating Related Polynucleotide Sequences

Included in the present invention are genes, promoters and promoter control elements which are related to those described in SEQ ID NO:1, SEQ ID NO:2, SEQ ID NO:4, SEQ ID NO:6 or SEQ ID NO:8. Such related sequence can be isolated utilizing nucleotide sequence identity;
coding sequence identity; or
common function or gene products.

Relatives can include both naturally occurring genes and promoters and non-natural gene and promoter sequences. Non-natural related gene or promoters include nucleotide substitutions, insertions or deletions of naturally-occurring gene or promoter sequences that do not substantially affect activity of the polynucleotides (e.g., activity of coding sequences or transcription modulation). For example, the binding of relevant DNA binding proteins can still occur with the non-natural promoter sequences and promoter control elements of the present invention.

According to current knowledge, promoter sequences and promoter control elements exist as functionally important regions, such as protein binding sites, and spacer regions. These spacer regions are apparently required for proper positioning of the protein binding sites. Thus, nucleotide substitutions, insertions and deletions can be tolerated in these spacer regions to a certain degree without loss of function.

In contrast, less variation is permissible in the functionally important regions, since changes in the sequence can interfere with protein binding. Nonetheless, some variation in the functionally important regions is permissible so long as function is conserved. In some embodiments, functionally important regions can include nucleotides 3321 to 3580 of SEQ ID NO:1. As described below, nucleotides 3321 to 3580 of SEQ ID NO:2 are useful for modulating transcriptional activity in suspensor cells and/or basal regions of plant embryos.

The effects of substitutions, insertions and deletions to the promoter sequences or promoter control elements may be to increase or decrease the binding of relevant DNA binding proteins to modulate transcript levels of a polynucleotide to be transcribed. Effects may include tissue-specific or condition-specific modulation of transcript levels of the polypeptide to be transcribed. Polynucleotides representing changes to the nucleotide sequence of the DNA-protein contact region by insertion of additional nucleotides, changes to identity of relevant nucleotides, including use of chemically-modified bases, or deletion of one or more nucleotides are considered encompassed by the present invention.

(1) Relatives Based on Nucleotide Sequence Identity

Included in the present invention are polynucleotides comprising genes or promoters exhibiting nucleotide sequence identity to SEQ ID NO:1, SEQ ID NO:2, SEQ ID NO:4, SEQ ID NO:6 or SEQ ID NO:8.

Definition

Typically, such related genes or promoters exhibit at least 50%, sometimes at least 60% or at least 70% or at least 80% sequence identity, preferably at least 85%, more preferably at least 90%, and most preferably at least 95%, even more preferably, at least 96%, 97%, 98% or 99% sequence identity compared to SEQ ID NO:1, SEQ ID NO:2, SEQ ID NO:4, SEQ ID NO:6 or SEQ ID NO:8. Indeed, any percent identity represented by an integer between 50–99 is contemplated for the invention. Such sequence identity can be calculated by the algorithms and computers programs described above.

Usually, such sequence identity is exhibited in an alignment region that is at least 75%, usually at least 80%; more usually, at least 85%, more usually at least 90%, and most usually at least 95%, even more usually, at least 96%, 97%, 98% or 99% of the length of a sequence shown in SEQ ID NO:1.

The percentage of the alignment length is calculated by counting the number of residues of the sequence in region of strongest alignment, e.g., a continuous region of the sequence that contains the greatest number of residues that are identical to the residues between two sequences that are being aligned. The number of residues in the region of strongest alignment is divided by the total residue length of a sequence in SEQ ID NO:1.

These related promoters may exhibit similar preferential transcription as SEQ ID NO:1 or other sequences of the invention such as nucleotides 1–4582 of SEQ ID NO:4, nucleotides 1–3154 of SEQ ID NO:6 or nucleotides 1–1609 of SEQ ID NO:8.

Construction of Polynucleotides

Naturally occurring promoters that exhibit nucleotide sequence identity to those shown in SEQ ID NO:1, SEQ ID NO:2, SEQ ID NO:4, SEQ ID NO:6 or SEQ ID NO:8 can be isolated using the techniques as described above. More specifically, such related promoters can be identified by varying stringencies, as defined above, in typical hybridization procedures such as, Southerns or probing of polynucleotide libraries, for example.

Non-natural promoter variants of those shown in SEQ ID NO:1, SEQ ID NO:2, SEQ ID NO:4, SEQ ID NO:6 or SEQ D NO:8 can be constructed using cloning methods that incorporate the desired nucleotide variation. See, for example, Ho, S. N., et al. *Gene* 77:51–59 (1989), describing a procedure site directed mutagenesis using PCR.

Any related promoter showing sequence identity to those shown in SEQ ID NO:1, SEQ ID NO:2, SEQ ID NO:4, SEQ ID NO:6 or SEQ ID NO:8 can be chemically synthesized as described above.

Also, the present invention includes non-natural promoters that exhibit the above-sequence identity to those in SEQ ID NO:1, SEQ ID NO:2, SEQ ID NO:4, SEQ ID NO:6 or SEQ ID NO:8.

The promoters and promoter control elements of the present invention may also be synthesized with 5' or 3' extensions, to facilitate additional manipulation, for instance.

(2) Relatives Based on Coding Sequence Identity

In addition, the present invention includes promoters of genes that comprise exons that encode polypeptide sequences that show sequence identity to the amino acid sequence displayed in SEQ ID NO:3, SEQ ID NO:5, SEQ ID NO:7, or SEQ ID NO:9.

Definition

Typically, the amino acid sequence of the genes comprising these related polynucleotides exhibit at least that exhibit at least 50%, at least 60%, at least 70% or at least 80% sequence identity to SEQ ID NO:3, SEQ ID NO:5, SEQ ID NO:7, or SEQ ID NO:9, preferably at least 85%, more preferably at least 90%, and most preferably at least 95%, even more preferably, at least 96%, 97%, 98% or 99% sequence identity to SEQ ID NO:3, SEQ ID NO:5, SEQ ID NO:7, or SEQ ID NO:9. Such sequence identity can be calculated by the algorithms and computers programs described above.

Usually, such sequence identity is exhibited in an alignment region that is at least 75% of the length of a sequence encoded by SEQ ID NO:2, SEQ ID NO:4, SEQ ID NO:6 or SEQ ID NO:8 or corresponding full-length sequence; more usually at least 80%; more usually, at least 85%, more usually at least 90%, and most usually at least 95%, even more usually, at least 96%, 97%, 98% or 99% of the length of a sequence encoded by SEQ ID NO:2, SEQ ID NO:4, SEQ ID NO:6 or SEQ ID NO:8.

Construction of Polynucleotides

The isolation of sequences from the genes of the invention may be accomplished by a number of techniques. For instance, oligonucleotide probes based on the sequences disclosed here can be used to identify the desired gene in a cDNA or genomic DNA library from a desired plant species. To construct genomic libraries, large segments of genomic DNA are generated by random fragmentation, e.g. using restriction endonucleases, and are ligated with vector DNA to form econcatemers that can be packaged into the appropriate vector. To prepare a library of embryo-specific cDNAs, mRNA is isolated from embryos and a cDNA library that contains the gene transcripts is prepared from the mRNA.

The cDNA or genomic library can then be screened using a probe based upon the sequence of a cloned embryo-specific gene such as the polynucleotides disclosed here. Probes may be used to hybridize with genomic DNA or cDNA sequences to isolate homologous genes in the same or different plant species.

Alternatively, the nucleic acids of interest can be amplified from nucleic acid samples using amplification techniques. For instance, polymerase chain reaction (PCR) technology to amplify the sequences of the genes directly from mRNA, from cDNA, from genomic libraries or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. Appropriate primers and probes for identifying embryo-specific genes from plant tissues are generated from comparisons of the sequences provided herein. For a general overview of PCR see PCR Protocols: A Guide to Methods and Applications. (Innis, M, Gelfand, D., Sninsky, J. and White, T., eds.), Academic Press, San Diego (1990).

Polynucleotides may also be synthesized by well-known techniques as described in the technical literature. See, e.g., Carruthers et al., Cold Spring Harbor Symp. *Quan. Biol.* 47:411–418 (1982), and Adams et al., *J. Am. Chem. Soc.* 105:661 (1983). Double stranded DNA fragments may then be obtained either by synthesizing the complementary strand and annealing the strands together under appropriate conditions, or by adding the complementary strand using DNA polymerase with an appropriate primer sequence.

Identified cDNA sequences can be aligned to the genomic sequences to identify the promoter region and sequences, which are located upstream of the 5'UTR and downstream of the preceding gene.

cDNA Isolation

The cDNAs can be isolated by various cloning methods described above. For example, probes and/or primer can be designed utilizing the sequences in SEQ ID NO:2, SEQ ID NO:4, SEQ ID NO:6 or SEQ ID NO:8. See, e.g., Ausubel et al. (1992); and Sambrook et al. (1989).

Such probes and primers can be used to identify cDNAs with a comprising at least one transcription start site. Full-length cDNA libraries are useful to identify cDNAs with at least one transcription start site. Such libraries can be constructed as described in the above-captioned applications in the Related Applications Section. Alternatively, tail-PCR or RACE can be used to isolated the 5' end of a cDNA.

Genomic Polynucleotide Isolation

Genomic sequences can be isolated with the sequence from the cDNA also found in the 5' UTR, exons or 3' UTR for probes and/or primers.

Alternatively, the promoter sequences upstream of the transcription start site or translation start site can be isolated using single primers designed having the portions of cDNA sequences 3' of the start codon of a sequence (e.g., SEQ ID NO:2, SEQ ID NO:4, SEQ ID NO:6 or SEQ ID NO:8) and used with random primers to isolate the corresponding upstream portion of genomic DNA.

Alternatively the promoters and promoter control elements of the invention can be identified by "walking" upstream from 5'-most portions of cDNA sequences in a genomic DNA library.

The promoter sequences will those 5' of the transcription start site which can be located using the 5' end of the corresponding cDNA. Alternatively, the start sites of a transcript can be assessed using primer extension assays (King et al., *Gene* 242:125 (2000)).

In addition, the 5' end of the promoter can be identified by either locating the upstream polyA signal or by identifying the cDNA corresponding to the preceding gene using the techniques described above.

D. Identifying Control Elements (1) Types of Transcription Control Elements

Promoter sequences comprise a number of promoter control elements that are capable of initiating transcription, regulating transcription rates and levels, etc. Promoter control elements modulate transcription when such control elements exhibit their transcription related activities, such as hybridizing to target polynucleotides; binding to repressor proteins, transcription factors, proteins or components of the nuclear matrix; able to act as a methylation site, etc. Promoter control elements include cis acting elements such as
  enhancers,
  scaffold/matrix attachment regions (S/MARs),
  locus control regions (LCRs).
Other promoter control elements include, without limitation:
  core or basal promoters,
  TATA boxes,
  initiator sites,
  transcription factor binding sites,
  repressor binding sites;
  and inverted repeats.
See, e.g., T. Boulikas, *J. Cell Biochem.*, 60, 297–316 (1996).

Promoter Control Elements of the Invention

The promoter control elements of the present invention include those that comprise SEQ ID NO:1, nucleotides 1–4582 of SEQ ID NO:4, nucleotides 1–3154 of SEQ ID NO:6 or nucleotides 1–1609 of SEQ ID NO:8, and fragments thereof. A particularly preferred fragment comprises nucleotides 3329 to 3475 of SEQ ID NO:1. As discussed below, this fragment confers suspensor-specific activity to a promoter. Additional promoter control elements include SEQ ID NO:10 and SEQ ID NO:11. Control elements of the invention alone, or as part of a heterologous promoter, are useful for modulation of transcription.

The size of the fragments of SEQ ID NO:1, nucleotides 1–4582 of SEQ ID NO:4, nucleotides 1–3154 of SEQ ID NO:6 or nucleotides 1–1609 of SEQ ID NO:8 can range from 5 bases to about 5 kilobases (kb). Typically, the fragment size is no smaller than 8 bases; more typically, no smaller than 10 or 12; more typically, no smaller than 15 bases; more typically, no smaller than 20 bases; more typically, no smaller than 25 bases; even more typically, no more than 30, 35, 40 or 50 bases.

Usually, the fragment size in no larger than 2 kb bases; more usually, no larger than 1 kb; more usually, no larger than 800 bases; more usually, no larger than 500 bases; even more usually, no more than 250, 200, 150 or 100 bases.

Relatives Based on Nucleotide Sequence Identity

Included in the present invention are promoter control elements exhibiting nucleotide sequence identity to those in SEQ ID NO:1, nucleotides 1–4582 of SEQ ID NO:4, nucleotides 1–3154 of SEQ ID NO:6 or nucleotides 1–1609 of SEQ ID NO:8.

Typically, such related promoters exhibit at least 80% sequence identity, preferably at least 85%, more preferably at least 90%, and most preferably at least 95%, even more preferably, at least 96%, 97%, 98% or 99% sequence identity compared to those shown in SEQ ID NO:1, nucleotides 1–4582 of SEQ ID NO:4, nucleotides 1–3154 of SEQ ID NO:6 or nucleotides 1–1609 of SEQ ID NO:8. Such sequence identity can be calculated by the algorithms and computers programs described above.

Relatives Based on Coding Sequence Identity

In addition, the present invention includes promoter control elements of genes that comprise exons that encode polypeptide sequences that show sequence identity to SEQ ID NO:3, SEQ ID NO:5, SEQ ID NO:7 or SEQ ID NO:9.

Typically, the amino acid sequence of the genes comprising these related promoters exhibit at least 80% sequence identity to those shown in SEQ ID NO:3, SEQ ID NO:5, SEQ ID NO:7 or SEQ ID NO:9, preferably at least 85%, more preferably at least 90%, and most preferably at least 95%, even more preferably, at least 96%, 97%, 98% or 99%. sequence identity to SEQ ID NO:3, SEQ ID NO:5, SEQ ID NO:7 or SEQ ID NO:9. Such sequence identity can be calculated by the algorithms and computers programs described above.

Usually, such sequence identity is exhibited in an alignment region that is at least 75% of the length of SEQ ID NO:3, SEQ ID NO:5, SEQ ID NO:7 or SEQ ID NO:9; more usually at least 80%; more usually, at least 85%, more usually at least 90%, and most usually at least 95%, even more usually, at least 96%, 97%, 98% or 99% of the length of SEQ ID NO:3, SEQ ID NO:5, SEQ ID NO:7 or SEQ ID NO:9.

Promoter Control Element Configuration

A common configuration of the promoter control elements in RNA polymerase II promoters is shown in FIG. 1.

For more description, see, e.g., T. Werner, *Mammalian Genome*, 10, 168–175 (1999).

Promoters are generally modular in nature. Promoters can consist of a basal promoter that functions as a site for assembly of a transcription complex comprising an RNA polymerase, for example RNA polymerase II. A typical transcription complex will include additional factors such as $TF_{II}B$, $TF_{II}D$, and $TF_{II}E$. Of these, $TF_{II}D$ appears to be the only one to bind DNA directly. The promoter might also contain one or more promoter control elements such as the elements discussed above. These additional control elements may function as binding sites for additional transcription factors that have the function of modulating the level of transcription with respect to tissue specificity and of transcriptional responses to particular environmental or nutritional factors, and the like.

One type of promoter control elements are polynucleotide sequences representing binding sites for proteins. Typically, within a particular functional module, protein binding sites constitute regions of 5 to 60, preferably 10 to 30, more preferably 10 to 20 nucleotides. Within such binding sites, there are typically 2 to 6 nucleotides that specifically contact amino acids of the nucleic acid binding protein.

The protein binding sites are usually separated from each other by 10 to several hundred nucleotides, typically by 15 to 150 nucleotides, often by 20 to 50 nucleotides.

Further, protein binding sites in promoter control elements often display dyad symmetry in their sequence. Such elements can bind several different proteins, and/or a plurality of sites can bind the same protein. Both types of elements may be combined in a region of 50 to 1,000 base pairs.

Binding sites for any specific factor have been known to occur almost anywhere in a promoter. For example, functional AP-1 binding sites can be located far upstream, as in the rat bone sialoprotein gene, where an AP-1 site located about 900 nucleotides upstream of the transcription start site suppresses expression. Yamauchi et al., *Matrix Biol.*, 15, 119–130 (1996). Attentively, an AP-1 site located close to the transcription start site plays an important role in the expression of Moloney murine leukemia virus. Sap et al., *Nature*, 340, 242–244 (1989).

(2) Those Identifiable by Bioinformatics

Promoter control elements from the promoters of the instant invention can be identified utilizing bioinformatic or computer driven techniques.

One method uses a computer program AlignACE to identify regulatory motifs in genes that exhibit common preferential transcription across a number of time points. The program identifies common sequence motifs in such genes. See, Roth et al., *Nature Biotechnol.* 16: 949–945 (1998); Tavazoie et al., *Nat Genet* 22(3):281–5 (1999).

Genomatix, also makes available a GEMS Launcher program and other programs to identify promoter control elements and configuration of such elements. Genomatix is located in Munich, Germany.

Other references also describe detection of promoter modules by models independent of overall nucleotide sequence similarity. See, e.g., Klingenhoff et al., *Bioinformatics* 15, 180–186 (1999).

Protein binding sites of promoters can be identified as reported in Frech, et al., *Nucleic Acids Research*, Vol. 21, No. 7, 1655–1664 (1993).

Other programs used to identify protein binding sites include, for example, Signal Scan, Prestridge et al., *Comput. Appl. Biosci.* 12: 157–160 (1996); Matrix Search, Chen et al., *Comput. Appl. Biosci.* 11: 563–566 (1995), available as part of Signal Scan 4.0; MatInspector, Ghosh et al., *Nucl. Acid Res.* 21: 3117–3118 (1993) available http://ww.gsf.de/cgi-bin/matsearch.pl; ConsInspector, Frech et al., *Nucl. Acids Res.* 21: 1655–1664 (1993), available at ftp://ariane.gsf.de/pub/dos; TFSearch; and TESS.

Frech et al., "Software for the analysis of DNA sequence elements of transcription" in Bioinformatics & Sequence Analysis, Vol. 13, no. 1, 89–97 (1997) is a review of different software for analysis of promoter control elements. This paper also reports the usefulness of matrix-based approaches to yield more specific results.

For other procedures, see, Fickett et al., *Curr. Op. Biotechnol.* 11: 19–24 (2000); and Quandt et al., *Nucleic Acids Res.* 23, 4878–4884 (1995).

(3) Those Identifiable by In-Vitro and In-Vivo Assays

Promoter control elements also can be identified with in-vitro assays, such as transcription detection methods; and with in-vivo assays, such as enhancer trapping protocols.

In-Vitro Assays

Examples of in vitro assays include detection of binding of protein factors that bind promoter control elements. Fragments of the instant promoters can be used to identify the location of promoter control elements. Another option for obtaining a promoter control element with desired properties is to modify known promoter sequences. This is based on the fact that the function of a promoter is dependent on the interplay of regulatory proteins that bind to specific, discrete nucleotide sequences in the promoter, termed motifs. Such interplay subsequently affects the general transcription machinery and regulates transcription efficiency. These proteins are positive regulators or negative regulators (repressors), and one protein can have a dual role depending on the context (Johnson, P. F. and McKnight, S. L. *Annu. Rev. Biochem.* 58:799–839 (1989)).

One type of in-vitro assay utilizes a known DNA binding factor to isolate DNA fragments that bind. If a fragment or promoter variant does not bind, then a promoter control element has been removed or disrupted. For specific assays, see, e.g., B. Luo et al., *J. Mol. Biol.* 266:470 (1997), S. Chusacultariachai et al., *J. Biol. Chem.* 274:23591 (1999), D. Fabbro et al., *Biochem. Biophys. Res. Comm.* 213:781 (1995)).

Alternatively, a fragment of DNA suspected of conferring a particular pattern of specificity can be examined for activity in binding transcription factors involved in that specificity by methods such as DNA footprinting (e.g. D. J. Cousins et al., *Immunology* 99:101 (2000); V. Kolla et al., *Biochem. Biophys. Res. Comm.* 266:5 (1999)) or "mobility-shift" assays (E. D. Fabiani et al., *J. Biochem.* 347:147 (2000); N. Sugiura et al., *J. Biochem* 347:155 (2000)) or fluorescence polarization (e.g. Royer et al., U.S. Pat. No. 5,445,935). Both mobility shift and DNA footprinting assays can also be used to identify portions of large DNA fragments that are bound by proteins in unpurified transcription extracts prepared from tissues or organs of interest.

Cell-free transcription extracts can be prepared and used to directly assay in a reconstitutable system (Narayan et al., *Biochemistry* 39:818 (2000)).

In-Vivo Assays

Promoter control elements can be identified with reporter genes in in-vivo assays with the use of fragments of the instant promoters or variants of the instant promoter polynucleotides.

For example, various fragments can be inserted into a vector, comprising a basal promoter, for example, operably linked to a reporter sequence, which, when transcribed, can produce a detectable label. Examples of reporter genes include those encoding luciferase, green fluorescent protein, GUS, neo, cat and bar. Alternatively, reporter sequence can be detected utilizing AFLP and microarray techniques.

In promoter probe vector systems, genomic DNA fragments are inserted upstream of the coding sequence of a reporter gene that is expressed only when the cloned fragment contains DNA having transcription modulation activity (Neve, R. L. et al., *Nature* 277:324–325 (1979)). Control elements are disrupted when fragments or variants lacking any transcription modulation activity. Probe vectors have been designed for assaying transcription modulation in *E. coli* (An, G. et al., *J. Bact.* 140:400–407 (1979)) and other bacterial hosts (Band, L. et al., *Gene* 26:313–315 (1983); Achen, M. G., *Gene* 45:45–49 (1986)), yeast (Goodey, A. R. et al., *Mol. Gen. Genet.* 204:505–511 (1986)) and mammalian cells (Pater, M. M. et al., *J. Mol. App. Gen.* 2:363–371 (1984)).

A different design of a promoter/control element trap includes packaging into retroviruses for more efficient delivery into cells. One type of retroviral enhancer trap was described by von Melchner et al. (Genes Dev. 6(6):919–27 (1992); U.S. Pat. No. 5,364,783). The basic design of this vector includes a reporter protein coding sequence engineered into the U3 portion of the 3' LTR. No splice acceptor consensus sequences are included, limiting its utility to work as an enhancer trap only. A different approach to a gene trap using retroviral vectors was pursued by Friedrich and Soriano (*Genes Dev.* 5(9):1513–23 (1991)), who engineered a lacZ-neo fusion protein linked to a splicing acceptor. LacZ-neo fusion protein expression from trapped loci allows not only for drug selection, but also for visualization of β-galatactosidase expression using the chromogenic substrate, X-gal.

A general review of tools for identifying transcriptional regulatory regions of genomic DNA is provided by J. W. Fickett et al. *Curr. Opn. Biotechnol.* 11:19 (2000).

(4) Non-Natural Control Elements

Non-natural control elements can be constructed by inserting, deleting or substituting nucleotides into the promoter control elements described above. Such control elements are capable of transcription modulation which can be determined using any of the assays described above.

E. Constructing Promoters with Control Elements

(1) Combining Promoters and Promoter Control Elements

The promoter polynucleotides and promoter control elements of the present invention, both naturally occurring and synthetic, can be combined with each other to produce the desired preferential transcription. Also, the polynucleotides of the invention can be combined with other known sequences to obtain other useful promoters to modulate, for example, tissue transcription specific or transcription specific to certain conditions. Such preferential transcription can be determined using the techniques or assays described above.

Fragments, variants, as well as full-length sequences such as those shown in SEQ ID NO:1, nucleotides 1–4582 of SEQ ID NO:4, nucleotides 1–3154 of SEQ ID NO:6 or nucleotides 1–1609 of SEQ ID NO:8 and relatives are useful alone or in combination.

The location and relation of promoter control elements within a promoter can affect the ability of the promoter to modulate transcription. The order and spacing of control elements is a factor when constructing promoters.

(2) Number of Promoter Control Elements

Promoters can contain any number of control elements. For example, a promoter can contain multiple transcription binding sites or other control elements. One element may confer tissue or organ specificity; another element may limit transcription to specific time periods, etc. Typically, promoters will contain at least a basal or core promoter as described above. Any additional element can be included as desired. For example, a fragment comprising a basal promoter can be fused with another fragment with any number of additional control elements.

(3) Spacing Between Control Elements

Spacing between control elements or the configuration or control elements can be determined or optimized to permit the desired protein-polynucleotide or polynucleotide interactions to occur.

For example, if two transcription factors bind to a promoter simultaneously or relatively close in time, the binding sites are spaced to allow each factor to bind without steric hindrance. The spacing between two such hybridizing control elements can be as small as a profile of a protein bound to a control element. In some cases, two protein binding sites can be adjacent to each other when the proteins bind at different times during the transcription process.

Further, when two control elements hybridize the spacing between such elements will be sufficient to allow the promoter polynucleotide to hairpin or loop to permit the two elements to bind. The spacing between two such hybridizing control elements can be as small as a t-RNA loop, to as large as 10 kb.

Typically, the spacing is no smaller than 5 bases; more typically, no smaller than 8; more typically, no smaller than 15 bases; more typically, no smaller than 20 bases; more typically, no smaller than 25 bases; even more typically, no more than 30, 35, 40 or 50 bases.

Usually, the fragment size in no larger than 5 kb bases; more usually, no larger than 2 kb; more usually, no larger than 1 kb; more usually, no larger than 800 bases; more usually, no larger than 500 bases; even more usually, no more than 250, 200, 150 or 100 bases.

Such spacing between promoter control elements can be determined using the techniques and assays described above.

F. Control of G564 or C541 Activity of Gene Expression

(1) Use of Nucleic Acids of the Invention to Inhibit Gene Expression

The isolated sequences prepared as described herein, can be used to prepare expression cassettes useful in a number of techniques. For example, expression cassettes of the invention can be used to suppress endogenous G564 or C541 gene expression. Inhibiting expression can be useful, for instance, to modulate or prevent suspensor cell development and/or embryo size, shape and/or rate of development. Inhibition of expression is also useful for modulating fertility of a plant.

A number of methods can be used to inhibit gene expression in plants. For instance, antisense technology can be conveniently used. To accomplish this, a nucleic acid segment from the desired gene is cloned and operably linked to a promoter such that the antisense strand of RNA will be transcribed. The expression cassette is then transformed into plants and the antisense strand of RNA is produced. In plant cells, it has been suggested that antisense RNA inhibits gene expression by preventing the accumulation of mRNA which encodes the enzyme of interest, see, e.g., Sheehy et al., *Proc. Nat. Acad. Sci. USA,* 85:8805–8809 (1988), and Hiatt et al., U.S. Pat. No. 4,801,340.

The antisense nucleic acid sequence transformed into plants will be substantially identical to at least a portion of the endogenous suspensor-specific gene or genes to be repressed. The sequence, however, does not have to be perfectly identical to inhibit expression. The vectors of the present invention can be designed such that the inhibitory effect applies to other proteins within a family of genes exhibiting homology or substantial homology to the target gene.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. Normally, a sequence of between about 30 or 40 nucleotides and about full length nucleotides should be used, though a sequence of at least about 100 nucleotides is preferred, a sequence of at least about 200 nucleotides is more preferred, and a sequence of at least about 500 nucleotides is especially preferred.

Catalytic RNA molecules or ribozymes can also be used to inhibit expression of embryo-specific genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. *Nature,* 334:585–591 (1988).

Another method of suppression is sense suppression. Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al., *The Plant Cell* 2:279–289 (1990), and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence in the expression cassette, needing less than absolute identity, also need not be full length, relative to either the primary transcription product or fully processed mRNA. This may be preferred to avoid concurrent production of some plants that are overexpressers. A higher identity in a shorter than full-length sequence compensates for a longer, less identical sequence. Furthermore, the introduced sequence need not have the same intron or exon pattern, and identity of non-coding segments will be equally effective. Normally, a sequence of the size ranges noted above for antisense regulation is used.

One of skill in the art will recognize that using technology based on specific nucleotide sequences (e.g., antisense or sense suppression technology), families of homologous genes can be suppressed with a single sense or antisense transcript. For instance, if a sense or antisense transcript is designed to have a sequence that is conserved among a family of genes, then multiple members of a gene family can be suppressed. Conversely, if the goal is to only suppress one member of a homologous gene family, then the sense or antisense transcript should be targeted to sequences with the most variance between family members.

Another means of inhibiting G564 or C541 function in a plant is by creation of dominant negative mutations. In this approach, non-functional, mutant G564 or C541 polypeptides, which retain the ability to interact with wild-type subunits are introduced into a plant.

(2) Use of Nucleic Acids of the Invention to Enhance Gene Expression

Isolated sequences prepared as described herein can also be used to prepare expression cassettes that enhance or increase endogenous G564 or C5541 gene expression. Where overexpression of a gene is desired, the desired gene from a different species may be used to decrease potential sense suppression effects. Enhanced expression of G564 or C541 polynucleotides is useful, for example, to modulate suspensor cell and/or embryo size, shape and/or rate of development. Enhanced expression is also useful for modulating plant fertility.

Any of a number of means well known in the art can be used to increase G564 or C541 activity in plants. Any organ can be targeted, such as shoot vegetative organs/structures (e.g. leaves, stems and tubers), roots, flowers and floral organs/structures (e.g. bracts, sepals, petals, stamens, carpels, anthers and ovules), seed (including apical or basal cells, suspensor, embryo, endosperm, and seed coat) and fruit. Alternatively, one or several G564 or C541 genes can be expressed constitutively (e.g., using the CaMV 35S promoter).

One of skill will recognize that the polypeptides encoded by the genes of the invention, like other proteins, have different domains that perform different functions. Thus, the gene sequences need not be full length, so long as the desired functional domain of the protein is expressed.

(3) Modification of Endogenous G564 or C541 Genes

Methods for introducing genetic mutations into plant genes and selecting plants with desired traits are well known. For instance, seeds or other plant material can be treated with a mutagenic chemical substance, according to standard techniques. Such chemical substances include, but are not limited to, the following: diethyl sulfate, ethylene imine, ethyl methanesulfonate and N-nitroso-N-ethylurea. Alternatively, ionizing radiation from sources such as, X-rays or gamma rays can be used.

Modified protein chains can also be readily designed utilizing various recombinant DNA techniques well known to those skilled in the art and described for instance, in Sambrook et al., supra. Hydroxylamine can also be used to introduce single base mutations into the coding region of the gene (Sikorsli, et al., (1991). *Meth. Enzymol.* 194: 302–318). For example, the chains can vary from the naturally occurring sequence at the primary structure level by amino acid substitutions, additions, deletions, and the like. These modifications can be used in a number of combinations to produce the final modified protein chain.

Alternatively, homologous recombination can be used to induce targeted gene modifications by specifically targeting the G564 or C541 gene in vivo (see, generally, Grewal and Klar, *Genetics* 146: 1221–1238 (1997) and Xu et al., *Genes Dev.* 10: 2411–2422 (1996)). Homologous recombination has been demonstrated in plants (Puchta et al., *Experientia* 50: 277–284 (1994), Swoboda et al., *EMBO J.* 13: 484–489 (1994); Offringa et al., *Proc. Natl. Acad. Sci. USA* 90: 7346–7350 (1993); and Kempin et al. *Nature* 389:802–803 (1997)).

In applying homologous recombination technology to the genes of the invention, mutations in selected portions of an G564 or C541 gene sequences (including 5' upstream, 3' downstream, and intragenic regions) such as those disclosed here are made in vitro and then introduced into the desired plant using standard techniques. Since the efficiency of homologous recombination is known to be dependent on the vectors used, use of dicistronic gene targeting vectors as described by Mountford et al., *Proc. Natl. Acad. Sci. USA* 91: 4303–4307 (1994); and Vaulont et al., *Transgenic Res.* 4: 247–255 (1995) are conveniently used to increase the efficiency of selecting for altered G564 or C541 gene expression in transgenic plants. The mutated gene will interact with the target wild-type gene in such a way that homologous recombination and targeted replacement of the wild-type gene will occur in transgenic plant cells, resulting in suppression of G564 or C541 activity.

Alternatively, oligonucleotides composed of a contiguous stretch of RNA and DNA residues in a duplex conformation with double hairpin caps on the ends can be used. The RNA/DNA sequence is designed to align with the sequence of the target G564 or C541 gene and to contain the desired nucleotide change. Introduction of the chimeric oligonucleotide on an extrachromosomal T-DNA plasmid results in efficient and specific G564 or C541 gene conversion directed by chimeric molecules in a small number of transformed plant cells. This method is described in Cole-Strauss et al., Science 273:1386–1389 (1996) and Yoon et al. Proc. Natl. Acad. Sci. USA 93: 2071–2076 (1996).

G. Heterologous Expression of the G564 or C541 Polynucleotides of the Invention

A DNA sequence coding for the desired polypeptide, for example a cDNA sequence encoding a full length protein, will preferably be combined with transcriptional and translational initiation regulatory sequences which will direct the transcription of the sequence from the gene in the intended tissues of the transformed plant.

For example, for overexpression, a plant promoter fragment may be employed which will direct expression of the gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of Agrobacterium tumafaciens, and other transcription initiation regions from various plant genes known to those of skill.

Alternatively, the plant promoter may direct expression of the polynucleotide of the invention in a specific tissue (tissue-specific promoters) or may be otherwise under more precise environmental control (inducible promoters). Examples of tissue-specific promoters under developmental control include promoters that initiate transcription only in certain tissues, such as fruit, seeds, or flowers. As noted above, the promoters from the G564 or C541 genes described here are particularly useful for directing gene expression so that a desired gene product is located in suspensor cells. Examples of environmental conditions that may affect transcription by inducible promoters include anaerobic conditions, elevated temperature, or the presence of light.

If proper polypeptide expression is desired, a polyadenylation region at the 3'-end of the coding region should be included. The polyadenylation region can be derived from the natural gene, from a variety of other plant genes, or from T-DNA.

The vector comprising the sequences (e.g., promoters or coding regions) from genes of the invention will typically comprise a marker gene which confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

G564 or C541 nucleic acid sequences of the invention are expressed recombinantly in plant cells to enhance and increase levels of endogenous G564 or C541 polypeptides. Alternatively, antisense or other G564 or C541 constructs (described above) are used to suppress G564 or C541 levels of expression. A DNA sequence coding for a G564 or C541 polypeptide, e.g., a cDNA sequence encoding a full length protein, can be combined with cis-acting (promoter) and trans-acting (enhancer) transcriptional regulatory sequences to direct the timing, tissue type and levels of transcription in the intended tissues of the transformed plant. Translational control elements can also be used.

The invention provides a G564 or C541 nucleic acid operably linked to a promoter that, in a preferred embodiment, is capable of driving the transcription of the G564 or C541 coding sequence in plants. The promoter can be, e.g., derived from plant or viral sources. The promoter can be, e.g., constitutively active, inducible, or tissue specific. In construction of recombinant expression cassettes, vectors, transgenic, of the invention, a different promoters can be chosen and employed to differentially direct gene expression, e.g., in some or all tissues of a plant or animal.

Typically, desired promoters are identified by analyzing the 5' sequences of a genomic clone corresponding to the suspensor-specific genes described here. Sequences characteristic of promoter sequences can be used to identify the promoter. Sequences controlling eukaryotic gene expression have been extensively studied. For instance, promoter sequence elements include the TATA box consensus sequence (TATAAT), which is usually 20 to 30 base pairs upstream of the transcription start site. In most instances the TATA box is required for accurate transcription initiation. In plants, further upstream from the TATA box, at positions –80 to –100, there is typically a promoter element wvith a series of adenines surrounding the trinucleotide G (or T) N G. J. Messing et al., in Genetic Engineering in Plants, pp.221–227 (Kosage, Meredith and Hollaender, eds. (1983)). A number of methods are known to those of skill in the art for identifying and characterizing promoter regions in plant genomic DNA (see, e.g., Jordano, et al., Plant Cell, 1: 855–866 (1989); Bustos, et al., Plant Cell, 1:839–854 (1989); Green, et al., EMBO J. 7,4035–4044 (1988); Meier, et al., Plant Cell, 3, 309–316 (1991); and Zhang (1996) Plant Physiology 110:1069–1079).

Constitutive Promoters

A promoter fragment can be employed which will direct expression of G564 or C541 nucleic acid in all transformed cells or tissues, e.g. as those of a regenerated plant. Such promoters are referred to herein as "constitutive" promoters and are active under most environmental conditions and states of development or cell differentiation. Promoters that drive expression continuously under physiological conditions are referred to as "constitutive" promoters and are active under most environmental conditions and states of development or cell differentiation. Examples of constitutive promoters include those from viruses which infect plants, such as the cauliflower mosaic virus (CaMV) 35S transcription initiation region (see, e.g., Dagless (1997) Arch. Virol. 142:183–191); the 1'- or 2'-promoter derived from T-DNA of Agrobacterium tumafaciens (see, e.g., Mengiste (1997) supra; O'Grady (1995) Plant Mol. Biol. 29:99–108); the promoter of the tobacco mosaic virus; the promoter of Figwort mosaic virus (see, e.g., Maiti (1997) Transgenic Res. 6:143–156); actin promoters, such as the Arabidopsis actin gene promoter (see, e.g., Huang (1997) Plant Mol. Biol. 1997 33:125–139); alcohol dehydrogenase (Adh) gene promoters (see, e.g., Millar (1996) Plant Mol. Biol. 31:897–904); ACT11 from Arabidopsis (Huang et al. Plant Mol. Biol. 33:125–139 (1996)), Cat3 from Arabidopsis (GenBank No. U43147, Zhong et al., Mol. Gen. Genet. 251:196–203 (1996)), the gene encoding stearoyl-acyl carrier protein desaturase from Brassica napus (Genbank No. X74782, Solocombe et al. Plant Physiol. 104:1167–1176 (1994)), GPc1 from maize (GenBank No. X15596, Martinez et al. J. Mol. Biol. 208:551–565 (1989)), Gpc2 from maize (GenBank No. U45855, Manjunath et al., Plant Mol. Biol. 33:97–112 (1997)), other transcription initiation regions from various plant genes known to those of skill. See also Holtorf (1995) "Comparison of different constitutive and inducible promoters for the overexpression of transgenes in Arabidopsis thaliana," Plant Mol. Biol. 29:637–646.

Inducible Promoters

Alternatively, a plant promoter may direct expression of the G564 or C541 nucleic acids of the invention under the influence of changing environmental conditions or developmental conditions. Examples of environmental conditions that may effect transcription by inducible promoters include anaerobic conditions, elevated temperature, drought, or the presence of light. Such promoters are referred to herein as "inducible" promoters. For example, the invention incorporates the drought-inducible promoter of maize (Busk (1997) supra); the cold, drought, and high salt inducible promoter from potato (Kirch (1997) *Plant Mol. Biol.* 33:897–909).

Alternatively, plant promoters which are inducible upon exposure to plant hormones, such as auxins, are used to express the nucleic acids of the invention. For example, the invention can use the auxin-response elements E1 promoter fragment (AuxREs) in the soybean (*Glycine max* L.) (Liu (1997) *Plant Physiol.* 115:397–407); the auxin-responsive *Arabidopsis* GST6 promoter (also responsive to salicylic acid and hydrogen peroxide) (Chen (1996) *Plant J.* 10: 955–966); the auxin-inducible parC promoter from tobacco (Sakai (1996) 37:906–913); a plant biotin response element (Streit (1997) *Mol. Plant Microbe Interact.* 10:933–937); and, the promoter responsive to the stress hormone abscisic acid (Sheen (1996) *Science* 274:1900–1902).

Plant promoters which are inducible upon exposure to chemicals reagents which can be applied to the plant, such as herbicides or antibiotics, are also used to express the nucleic acids of the invention. For example, the maize In2-2 promoter, activated by benzenesulfonamide herbicide safeners, can be used (De Veylder (1997) *Plant Cell Physiol.* 38:568–577); application of different herbicide safeners induces distinct gene expression patterns, including expression in the root, hydathodes, and the shoot apical meristem. The G564 or C541 coding sequences can also be under the control of, e.g., a tetracycline-inducible promoter, e.g., as described with transgenic tobacco plants containing the *Avena sativa* L. (oat) arginine decarboxylase gene (Masgrau (1997) *Plant J.* 11:465–473); or, a salicylic acid-responsive element (Stange (1997) *Plant J.* 11:1315–1324.

The following are promoters that are induced under stress conditions and can be combined with those of the present invention: Idh1 (oxygen stress; tomato; see Germain and Ricard *Plant Mol Biol* 35:949–54 (1997)), GPx and CAT (oxygen stress; mouse; see Franco et al., *Free Radic Biol Med* 27:1122–32 (1999), ci7 (cold stress; potato; see Kirch et al. *Plant Mol Biol.* 33:897–909 (1997)), Bz2 (heavy metals; maize; see Marrs and Walbot. *Plant Physiol* 113:93–102 (1997)), HSP32 (hyperthermia; rat; see Raju and Maines. *Biochim Biophys Acta* 1217:273–80 (1994)); MAPKAPK-2 (heat shock; *Drosophila*; see Larochelle and Suter *Gene* 163:209–14 (1995)).

In addition, the following examples of promoters are induced by the presence or absence of light can be used in combination with those of the present invention: Topoisomerase II (pea; see Reddy et al., *Plant Mol Biol* 41:125–37 (1999)), chalcone synthase (soybean; see Wingender et al., *Mol Gen Genet* 218:315–22 (1989)) mdm2 gene (human tumor; see Saucedo et al. *Cell Growth Differ* 9:119–30 (1998)), Clock and BMAL1 (rat; see Namihira et al., *Neurosci Lett* 271:1–4 (1998), PHYA (*Arabidopsis*; see Canton and Quail *Plant Physiol* 121:1207–16 (1999)), PRB-1b (tobacco; see Sessa et al., *Plant Mol Biol* 28:537–47 (1995)) and Ypr10 (common bean; see Walter et al. *Eur J Biochem* 239:281–93 (1996)).

Tissue-Specific Promoters

Alternatively, the plant promoter may direct expression of the polynucleotide of the invention in a specific tissue (tissue-specific promoters). Tissue specific promoters are transcriptional control elements that are only active in particular cells or tissues at specific times during plant development, such as in vegetative tissues or reproductive tissues. Promoters from the G564 or C541 genes of the invention are particularly useful for tissue-specific direction of gene expression so that a desired gene product is generated only or preferentially in suspensors, as described below.

Examples of tissue-specific promoters under developmental control include promoters that initiate transcription only (or primarily only) in certain tissues, such as vegetative tissues, e.g., roots or leaves, or reproductive tissues, such as fruit, ovules, seeds, pollen, pistols, flowers, or any embryonic tissue. Reproductive tissue-specific promoters may be, e.g., ovule-specific, embryo-specific, endosperm-specific, integument-specific, seed and seed coat-specific, pollen-specific, petal-specific, sepal-specific, or some combination thereof.

Suitable seed-specific promoters are derived from the following genes: MAC1 from maize, Sheridan (1996) *Genetics* 142:1009–1020; Cat3 from maize, GenBank No. L05934, Abler (1993) *Plant Mol. Biol.* 22:10131–1038; vivparous-1 from *Arabidopsis*, Genbank No. U93215; atmyc1 from *Arabidopsis*, Urao (1996) *Plant Mol. Biol.* 32:571–57; Conceicao (1994) *Plant* 5:493–505; napA from *Brassica napus*, GenBank No. J02798, Josefsson (1987) JBL 26:12196–1301; the napin gene family from *Brassica napus*, Sjodahl (1995) *Planta* 197:264–271.

The ovule-specific BEL1 gene described in Reiser (1995) *Cell* 83:735–742, GenBank No. U39944, can also be used. See also Ray (1994) *Proc. Natl. Acad. Sci. USA* 91:5761–5765. The egg and central cell specific FIE1 promoter is also a useful reproductive tissue-specific promoter.

Sepal and petal specific promoters are also used to express G564 nucleic acids in a reproductive tissue-specific manner. For example, the *Arabidopsis* floral homeotic gene APETALA1 (AP1) encodes a putative transcription factor that is expressed in young flower primordial and later becomes localized to sepals and petals (see, e.g., Gustafson-Brown (1994) *Cell* 76:131–143; Mandel (1992) *Nature* 360:273–277). A related promoter, for AP2, a floral homeotic gene that is necessary for the normal development of sepals and petals in floral whorls, is also useful (see, e.g., Drews (1991) *Cell* 65:991–1002; Bowman (1991) *Plant Cell* 3:749–758). Another useful promoter is that controlling the expression of the unusual floral organs (ufo) gene of *Arabidopsis*, whose expression is restricted to the junction between sepal and petal primordia (Bossinger (1996) *Development* 122:1093–1102).

A maize pollen-specific promoter has been identified in maize (Guerrero (1990) *Mol. Gen. Genet.* 224:161–168). Other genes specifically expressed in pollen are described, e.g., by Wakeley (1998) *Plant Mol. Biol.* 37:187–192; Ficker (1998) *Mol. Gen. Genet.* 257:132–142; Kulikauskas (1997) *Plant Mol. Biol.* 34:809–814; Treacy (1997) *Plant Mol. Biol.* 34:603–611.

Other suitable promoters include those from genes encoding embryonic storage proteins. For example, the gene encoding the 2S storage protein from *Brassica napus*, Dasgupta (1993) *Gene* 133:301–302; the 2s seed storage protein gene family from *Arabidopsis*; the gene encoding oleosin 20 kD from *Brassica napus*, GenBank No. M63985; the genes encoding oleosin A, Genbank No. U09118, and, oleosin B, Genbank No. U09119, from soybean; the gene encoding oleosin from *Arabidopsis*, Genbank No. Z17657; the gene encoding oleosin 18 kD from maize, GenBank No. J05212, Lee (1994) *Plant Mol. Biol.* 26:1981–1987; and, the gene encoding low molecular weight sulphur rich protein from soybean, Choi (1995) *Mol Gen, Genet.* 246:266–268, can be used. The tissue specific E8 promoter from tomato is particularly useful for directing gene expression so that a desired gene product is located in fruits.

A tomato promoter active during fruit ripening, senescence and abscission of leaves and, to a lesser extent, of flowers can be used (Blume (1997) *Plant J.* 12:731–746). Other exemplary promoters include the pistil specific promoter in the potato (*Solanum tuberosum* L.) SK2 gene, encoding a pistil-specific basic endochitinase (Ficker (1997) *Plant Mol. Biol.* 35:425–431); the Blec4 gene from pea (*Pisum sativum* cv. *Alaska*), active in epidermal tissue of vegetative and floral shoot apices of transgenic alfalfa. This makes it a useful tool to target the expression of foreign genes to the epidermal layer of actively growing shoots.

A variety of promoters specifically active in vegetative tissues, such as leaves, stems, roots and tubers, can also be used to express the G564 or C541 nucleic acids of the invention. For example, promoters controlling patatin, the major storage protein of the potato tuber, can be used, see, e.g., Kim (1994) *Plant Mol. Biol.* 26:603–615; Martin (1997) *Plant J.* 11:53–62. The ORF13 promoter from *Agrobacterium rhizogenes* which exhibits high activity in roots can also be used (Hansen (1997) *Mol. Gen. Genet.* 254:337–343. Other useful vegetative tissue-specific promoters include: the tarin promoter of the gene encoding a globulin from a major taro (*Colocasia esculenta* L. Schott) corm protein family, tarin (Bezerra (1995) *Plant Mol. Biol.* 28:137–144); the curculin promoter active during taro corm development (de Castro (1992) *Plant Cell* 4:1549–1559) and the promoter for the tobacco root-specific gene TobRB7, whose expression is localized to root meristem and immature central cylinder regions (Yamamoto (1991) *Plant Cell* 3:371–382).

Leaf-specific promoters, such as the ribulose biphosphate carboxylase (RBCS) promoters can be used. For example, the tomato RBCS1, RBCS2 and RBCS3A genes are expressed in leaves and light-grown seedlings, only RBCS1 and RBCS2 are expressed in developing tomato fruits (Meier (1997) *FEBS Lett.* 415:91–95). A ribulose bisphosphate carboxylase promoters expressed almost exclusively in mesophyll cells in leaf blades and leaf sheaths at high levels, described by Matsuoka (1994) *Plant J.* 6:311–319, can be used. Another leaf-specific promoter is the light harvesting chlorophyll a/b binding protein gene promoter, see, e.g., Shiina (1997) *Plant Physiol.* 115:477–483; Casal (1998) *Plant Physiol.* 116:1533–1538. The *Arabidopsis thaliana* myb-related gene promoter (Atmyb5) described by Li (1996) *FEBS Lett.* 379:117–121, is leaf-specific. The Atmyb5 promoter is expressed in developing leaf trichomes, stipules, and epidermal cells on the margins of young rosette and cauline leaves, and in immature seeds. Atmyb5 mRNA appears between fertilization and the 16 cell stage of embryo development and persists beyond the heart stage. A leaf promoter identified in maize by Busk (1997) *Plant J.* 11:1285–1295, can also be used.

Another class of useful vegetative tissue-specific promoters are meristematic (root tip and shoot apex) promoters. For example, the "SHOOTMERISTEMLESS" and "SCARECROW" promoters, which are active in the developing shoot or root apical meristems, described by Di Laurenzio (1996) *Cell* 86:423–433; and, Long (1996) *Nature* 379:66–69; can be used. Another useful promoter is that which controls the expression of 3-hydroxy-3-methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto (1995) *Plant Cell.* 7:517–527). Also useful are kn1-related genes from maize and other species which show meristem-specific expression, see, e.g., Granger (1996) *Plant Mol. Biol.* 31:373–378; Kerstetter (1994) *Plant Cell* 6:1877–1887; Hake (1995) *Philos. Trans. R. Soc. Lond. B. Biol. Sci.* 350:45–51. For example, the *Arabidopsis thaliana* KNAT1 promoter. In the shoot apex, KNAT1 tanscript is localized primarily to the shoot apical meristem; the expression of KNAT1 in the shoot meristem decreases during the floral transition and is restricted to the cortex of the inflorescence stem (see, e.g., Lincoln (1994) *Plant Cell* 6:1859–1876).

One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

In another embodiment, a G564 nucleic acid is expressed through a transposable element. This allows for constitutive, yet periodic and infrequent expression of the constitutively active polypeptide. The invention also provides for use of tissue-specific promoters derived from viruses which can include, e.g., the tobamovirus subgenomic promoter (Kumagai (1995) *Proc. Natl. Acad. Sci. USA* 92:1679–1683; the rice tungro bacilliform virus (RTBV), which replicates only in phloem cells in infected rice plants, with its promoter which drives strong phloem-specific reporter gene expression; the cassava vein mosaic virus (CVMV) promoter, with highest activity in vascular elements, in leaf mesophyll cells, and in root tips (Verdaguer (1996) *Plant Mol. Biol.* 31:1129–1139).

The promoters and control elements of the following genes can also be used in combination with the present invention to confer tissue specificity: MipB (iceplant; Yamada et al. *Plant Cell* 7:1129–42 (1995)) and SUCS (root nodules; broadbean; Kuster et al. *Mol Plant Microbe Interact* 6:507–14 (1993)) for roots, OsSUT1 (rice; Hirose et al., *Plant Cell Physiol* 38:1389–96 (1997)) for leaves, Msg (soybean; Stomvik et al., *Plant Mol Biol* 41:217–31 (1999)) for siliques, cell (*Arabidopsis*; Shani et al. *Plant Mol Biol* 34(6):837–42 (1997)) and ACT11 (*Arabidopsis*; Huang et al. *Plant Mol Biol* 33:125–39 (1997)) for inflorescence.

Still other promoters are affected by hormones or participate in specific physiological processes, which can be used in combination with those of present invention. Some examples are the ACC synthase gene that is induced differently by ethylene and brassinosteroids (mung bean; Yi et al. *Plant Mol Biol* 41:443–54 (1999)), the TAPG1 gene that is active during abscission (tomato; Kalaitzis et al., *Plant Mol Biol* 28:647–56 (1995)), and the 1-aminocyclopropane-1-carboxylate synthase gene (carnation; Jones et al., *Plant Mol Biol* 28:505–12 (1995)) and the CP-2/cathepsin L gene (rat; Kim and Wright. *Biol Reprod* 57:1467–77 (1997)), both active during senescence.

H. Vectors

Vectors are a useful component of the present invention. In particular, the present promoters and/or promoter control elements may be delivered to a system such as a cell by way of a vector. For the purposes of this invention, such delivery may range from simply introducing the promoter or promoter control element by itself randomly into a cell to integration of a cloning vector containing the present promoter or promoter control element. Thus, a vector need not be limited to a DNA molecule such as a plasmid, cosmid or bacterial phage that has the capability of replicating autonomously in a host cell. All other manner of delivery of the promoters and promoter control elements of the invention are envisioned. The various T-DNA vector types are a preferred vector for use with the present invention. Many useful vectors are commercially available.

It may also be useful to attach a marker sequence to the present promoter and promoter control element in order to determine activity of such sequences. Marker sequences typically include genes that provide antibiotic resistance, such as tetracycline resistance, hygromycin resistance or ampicillin resistance, or provide herbicide resistance. Specific selectable marker genes may be used to confer resistance to herbicides such as glyphosate, glufosinate or broxynil (Comai et al., *Nature* 317: 741–744 (1985); Gordon-Kamm et al., *Plant Cell* 2: 603–618 (1990); and Stalker et al., *Science* 242: 419–423 (1988)). Other marker genes exist which provide hormone responsiveness.

(1) Modification of Transcription by Promoters and Promoter Control Elements

The promoter or promoter control element of the present invention may be operably linked to a polynucleotide to be transcribed. In this manner, the promoter or promoter control element may modify transcription by modulate transcript levels of that polynucleotide when inserted into a genome.

However, prior to insertion into a genome, the promoter or promoter control element need not be linked, operably or otherwise, to a polynucleotide to be transcribed. For example, the promoter or promoter control element may be inserted alone into the genome in front of a polynucleotide already present in the genome. In this manner, the promoter or promoter control element may modulate the transcription of a polynucleotide that was already present in the genome. This polynucleotide may be native to the genome or inserted at an earlier time.

Alternatively, the promoter or promoter control element may be inserted into a genome alone to modulate transcription. See, for example, Vaucheret, H et al. (1998) *Plant J* 16: 651–659. Rather, the promoter or promoter control element may be simply inserted into a genome or maintained extra-chromosomally as a way to divert transcription resources of the system to itself This approach may be used to down-regulate the transcript levels of a group of polynucleotide(s).

(2) Polynucleotides To Be Transcribed

The nature of the polynucleotide to be transcribed is not limited. Specifically, the polynucleotide may include sequences which will have activity as RNA as well as sequences which result in a polypeptide product. These sequences may include, but are not limited to antisense sequences, ribozyme sequences, spliceosomes, amino acid coding sequences, and fragments thereof.

Specific coding sequences may include, but are not limited to endogenous proteins or fragments thereof, or heterologous proteins including marker genes or fragments thereof.

Promoters and control elements of the present invention are useful for modulating metabolic or catabolic processes. Such processes include, but are not limited to, secondary product metabolism, amino acid synthesis, seed protein storage, oil development, pest defense and nitrogen usage. Some examples of genes, transcripts and peptides or polypeptides participating in these processes, which can be modulated by the present invention: are tryptophan decarboxylase (tdc) and strictosidine synthase (str1), dihydrodipicolinate synthase (DHDPS) and aspartate kinase (AK), 2S albumin and alpha-, beta-, and gamma-zeins, ricinoleate and 3-ketoacyl-ACP synthase (KAS), *Bacillus thuringiensis* (Bt) insecticidal protein, cowpea trypsin inhibitor (CpTI), asparagine synthetase and nitrite reductase. Alternatively, expression constructs can be used to inhibit expression of these peptides and polypeptides by incorporating the promoters in constructs for antisense use, co-suppression use or for the production of dominant negative mutations.

(3) Other Regulatory Elements

As explained above, several types of regulatory elements exist concerning transcription regulation. Each of these regulatory elements may be combined with the present vector if desired.

(4) Other Components of Vectors

Translation of eukaryotic mRNA is often initiated at the codon which encodes the first methionine. Thus, when constructing a recombinant polynucleotide according to the present invention for expressing a protein product, it is preferable to ensure that the linkage between the 3' portion, preferably including the TATA box, of the promoter and the polynucleotide to be transcribed, or a functional derivative thereof, does not contain any intervening codons which are capable of encoding a methionine.

The vector of the present invention may contain additional components. For example, an origin of replication allows for replication of the vector in a host cell. Additionally, homologous sequences flanking a specific sequence allows for specific recombination of the specific sequence at a desired location in the target genome. T-DNA sequences also allow for insertion of a specific sequence randomly into a target genome.

The vector may also be provided with a plurality of restriction sites for insertion of a polynucleotide to be transcribed as well as the promoter and/or promoter control elements of the present invention. The vector may additionally contain selectable marker genes. The vector may also contain a transcriptional and translational initiation region, and a transcriptional and translational termination region functional in the host cell. The termination region may be native with the transcriptional initiation region, may be native with the polynucleotide to be transcribed, or may be derived from another source. Convenient termination regions are available from the Ti-plasmid of *A. tumefaciens*, such as the octopine synthase and nopaline synthase termination regions. See also, Guerineau et al., *Mol. Gen. Genet.* 262:141–144 (199 1); Proudfoot, *Cell* 64:671–674 (1991); Sanfacon et al., *Genes Dev.* 5:141–149 (1991); Mogen et al., *Plant Cell* 2:1261–1272 (1990); Munroe et al., *Gene* 91:151–158 (1990); Ballas et al., *Nucleic Acids Res.* 17:7891–7903 (1989); Joshi et al., *Nucleic Acid Res.* 15:9627–9639(1987).

Where appropriate, the polynucleotide to be transcribed may be optimized for increased expression in a certain host cell. For example, the polynucleotide can be synthesized using preferred codons for improved transcription and translation. See U.S. Pat. Nos. 5,380,831, 5,436,391; see also Murray et al., *Nucleic Acids Res.* 17:477–498 (1989).

Additional sequence modifications include elimination of sequences encoding spurious polyadenylation signals, exon intron splice site signals, transposon-like repeats, and other such sequences well characterized as deleterious to expression. The G-C content of the polynucleotide may be adjusted to levels average for a given cellular host, as calculated by reference to known genes expressed in the host cell. The polynucleotide sequence may be modified to avoid hairpin secondary mRNA structures.

A general description of expression vectors and reporter genes can be found in Gruber, et al., "Vectors for Plant Transformation, in Methods in Plant Molecular Biology &

Biotechnology" in Methods in Plant Molecular Biology & Biotechnology, (Glich et al., eds. 1993) pp. 89–119. Moreover GUS expression vectors and GUS gene cassettes are available from Clonetech Laboratories, Inc., Palo Alto, Calif. while luciferasc expression vectors and luciferase gene cassettes are available from Promega Corp. (Madison, Wis.). GFP vectors are available from Aurora Biosciences.

I. Polynucleotide Insertion into a Host Cell

The polynucleotides according to the present invention can be inserted into a host cell. A host cell includes but is not limited to a plant, mammalian, insect, yeast, and prokaryotic cell, preferably a plant cell.

The method of insertion into the host cell genome is choosen based on convenience. For example, the insertion into the host cell genome may either be accomplished by vectors which integrate into the host cell genome or by vectors which exist independent of the host cell genome.

The nucleic acids of the invention can be used to confer desired traits on essentially any plant. Thus, the invention has use over a broad range of plants, including species from the genera *Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghun, Trigonella, Triticum, Vitis, Vigna*, and, *Zea*.

(1) Polynucleotides Autonomous of the Host Genome

The polynucleotides the present invention can exist autonomous or independent of the host cell genome. Vectors of these types are known in the art and include, for example, certain type of non-integrating viral vectors, autonomously replicating plasmids, artificial chromosomes, and the like.

Additionally, in some cases transient expression of a polynucleotide may be desired.

(2) Polynucleotides Integrated into the Host Genome

The promoter sequences, promoter control elements or vectors of the present invention may be transformed into host cells. These transformations may be into protoplasts or intact tissues or isolated cells. Preferably expression vectors are introduced into intact tissue. General methods of culturing plant tissues are provided for example by Maki et al. "Procedures for Introducing Foreign DNA into Plants" in Methods in Plant Molecular Biology & Biotechnology, (Glich et al., eds. 1993) pp. 67–88; and by Phillips et al. "Cell-Tissue Culture and In-Vitro Manipulation" in Corn & Corn Improvement, 3rd Edition (Sprague et al., *eds.* 1998) pp. 345–387.

Methods of introducing polynucleotides into plant tissue include the direct infection or co-cultivation of plant cell with *Agrobacterium tumefaciens*, Horsch et al., *Science*, 227:1229 (1985). Descriptions of *Agrobacterium* vector systems and methods for *Agrobacterium*-mediated gene transfer provided by Gruber et al., supra.

Alternatively, polynucleotides are introduced into plant cells or other plant tissues using a direct gene transfer method such as microprojectile-mediated delivery, DNA injection, electroporation and the like. More preferably polynucleotides are introduced into plant tissues using the microprojectile media delivery with the biolistic device. See, for example, Tomes et al., "Direct DNA transfer into intact plant cells via microprojectile bombardment" in Plant Cell, Tissue and Organ Culture: Fundamental Methods (: Gamborg and Phillips, eds. 1995).

In another embodiment of the current invention, expression constructs can be used for gene expression in callus culture for the purpose of expressing marker genes encoding peptides or polypeptides which allow identification of transformed plants. Here, a promoter that is operatively linked to a polynucleotide to be transcribed is transformed into plant cells and the transformed tissue is then placed on callus-inducing media. If the transformation is conducted with leaf discs, for example, callus will initiate along the cut edges. Once callus growth has initiated, callus cells can be transferred to callus shoot-inducing or callus root-inducing media Gene expression will occur in the callus cells developing on the appropriate media: callus root-inducing promoters will be activated on callus root-inducing media, etc. Examples of such peptides or polypeptides useful as transformation markers include, but are not limited to barstar, glyphosate, chloramphenicol acetyltransferase (CAT), kanamycin, spectinomycin, streptomycin or other antibiotic resistance enzymes, green fluorescent protein (GFP), and β-glucuronidase (GUS), etc. Some of the promoters of the invention will also be capable of sustaining expression in some tissues or organs after the initiation or completion of regeneration. Examples of these tissues or organs are somatic embryos, cotyledon, hypocotyl, epicotyl, leaf, stems, roots, flowers and seed.

Integration into the host cell genome also can be accomplished by methods known in the art, for example, by the homologous sequences or T-DNA discussed above or using the cre-lox system (A. C. Vergunst et al., *Plant Mol. Biol.* 38:393 (1998)).

J. Utility

Common Uses

The polynucleotides of the invention have a variety of uses. For example, modulation of expression of the gene products of the invention can be used to modulate suspensor cell and/or embryo size, shape or rates of development.

The suspensor-specific promoters of the invention are also useful for expression of any number of polynucleotides in a suspensor-specific fashion. Exemplary gene products that can be expressed under the control of the promoters of the invention include toxic gene products. In some embodiments, toxic gene products are also expressed in the embryo under the control of the same or a second promoter. By preventing development of the suspensor cell and/or the embryo, plants with modulated fertility and/or that produce seedless fruit can be developed.

Examples of toxic genes include, e.g., those which produce toxic substances, disrupt cell function, suppress genes required by the cell (such as by using anti-sense, sense suppression, or ribozymes), and disruption of mitochondrial function. Particular examples include, barnase (Sancho & Fershi, *J. Mol. Biol.* 224:741–47 (1992)). diphtheria toxin (DT) A chain, which adenoribosylates elongation factor EF-2, thus blocking protein synthesis (Herrera et al., *Proc. Natl. Acad. Sci., USA* 91:12999–13003 (1994)), and the thymidine kinase (tk) gene, which provides a conditional cell-lethal function, requiring the presence of a nucleoside analog such as ganciclovir for lethality (Brady et al., *Proc. Natl. Acad. Sci., USA* 91:365–69 (1994)).

Alternatively, growth regulators such as gene products that modulate gibberellin expression, can be specifically expressed within the suspensor, thereby modulating (e.g., increasing or decreasing) the attached embryo's size, shape of rate of development.

An additional utility includes the expression of gene products that induce embryonic features to the suspensor cell, thereby leading to the development of a second embryo. Examples of the gene products that induce embryonic features include the LEC1 (see, e.g., Lotan, et al., *Cell* 93(7):1 195–205 (1998)).

In yet another use, nucleic acids of the invention can be used in the development of apomictic plant lines (i.e., plants in which asexual reproductive processes occur in the ovule, see, Koltunow, A. *Plant Cell* 5: 1425–1437 (1993) for a discussion of apomixis). Aponixis provides a novel means to select and fix complex heterozygous genotypes that cannot be easily maintained by traditional breeding. Thus, for instance, new hybrid lines with desired traits (e.g., hybrid vigor) can be obtained and readily maintained.

In yet another use, expression cassettes comprising the promoter polynucleotides of the invention can be used to express genes that result in apomictic plants. Examples of genes useful in creating apomictic planst include LEC1 nucleic acids as described by Lotan, et al. *Cell* 93: 1195–1205 (1998) and in U.S. Ser. No. 09/026,221 as well as FIE and MEDEA nucleic acids as described in Ohad et al., *Plant Cell* 11:407–415 (1999); Grossniklaus et al., *Science* 280:446–450 (1998) and U.S. Ser. No. 09/177,249. In these embodiments, constructs providing expression of a LEC1, FIE, MEDEA or other nucleic acids capable of inducing apomictic fruit are used alone or in combination.

The following examples are provided for a further understanding of the invention, however, the invention is not to be construed as limited thereto.

EXAMPLES

Materials and Methods

Plant Materials and Maintenance

Seeds of the day neutral Scarlet Runner Bean cultivar 'Hammond's Dwarf Red Flower' (Vermont Bean Seed Company, Fair Haven, Vt.; Nagl, 1990) were germinated in a soil mixture of vermiculite, perlite, sandy-loam soil, sphagnum peat moss, and plaster sand respectively at a ratio of 3:3:2:2. Plants were maintained in a 16:8 hour light/dark cycle in the greenhouse. Flowers were hand-pollinated by lightly brushing the stigma with a watercolor brush containing pollen. Hand-pollinated flowers were tagged and seeds were harvested at specific days after pollination.

Suspensor Isolation

The micropylar half of a 6 days after pollination (DAP) seed was cut and placed upright on its cut side under a dissecting microscope. Approximately 1 mm was sliced from the left and right sides of the seed coat "flat face." The seed was turned on its "flat face" and the remaining seed coat and endosperm were removed from the exposed embryo proper. The entire embryo was isolated and then the suspensor was separated from the embryo proper by microdissection. Generally, ten suspensors were isolated per hour.

RNA Isolation and Gel Blot Analysis

Polysomal RNAs were isolated according to the procedure of Cox and Goldberg (1988). Poly(A) mRNA was isolated from total polysomal RNA using the PolyATract® mRNA isolation system (Promega: Madison, Wis.) and the protocol supplied by the manufacturer. Total RNAs, used for the Differential Display Reverse Transcription Polymerase Chain Reaction (DD-RT-PCR) and RNA gel blot experiments, were isolated using the RNAeasy® plant total RNA kit (Qiagen: Chatsworth, Calif.). RNAs were treated with RNAse-free DNAse (Boehringer Manaheim: Indianapolis, Ind.) following the protocol of Ausubel et al., (1992). RNA gel blots were carried out as described by Sambrook et al. (1989). $^{32}$P-labeled DNA probes for the RNA gel blots were prepared by the random-priming procedure of Feinberg and Vogelstein (1984).

cDNA Library Construction and Screening

A cDNA library of 5–9 DAP Scarlet Runner Bean seeds containing globular-stage embryos was constructed using the ZAP Express® cDNA synthesis kit (Stratagene: La Jolla, Calif.). Poly(A) mRNA was used as a template to generate first-strand cDNA using MMLV reverse transcriptase and a 50-base oligonucleotide linker-primer [5'-(GA)$_{10}$ACTAGTCTCGAG(T)$_{18}$-3' (SEQ ID NO:25)]. Double-strand cDNAs were blunt-ended and ligated to an EcoRI adapter. After phosphorylation of EcoRI 5' ends, the cDNAs were digested with XhoI and size-fractionated on a Sephacryl S-400 column to exclude cDNAs that were smaller than 250 bp. The fractionated cDNAs were ligated to the λZAP vector. About 3,000 recombinants from the unamplified library were differentially screened with $^{32}$P-labeled first-strand cDNAs generated from: (1) 5–9 DAP seed micropylar region poly(A) mRNA and (2) leaf poly(A) mRNA. cDNA clones representing mRNAs preferentially present in the micropylar region were screened two more times following the strategy used in the primary screen.

Differential Display Reverse Transcription Polymerase Chain Reaction

Differential display procedures of Liang and Pardee (Liang, P., et al., *Science*, 257:967–971 (1992)) were followed using the RNAimage™ kit (GenHunter Corp.: Nashville, Tenn.). Differential display reactions were carried out using total RNA templates from: (1) 6–8 DAP dissected suspensors of globular-stage embryos, (2) 6 DAY embryo-containing micropylar seed regions, (3) 6 DAP non-embryo-containing chalazal seed regions, (4) 6–8 DAP isolated globular-stage embryo propers, (5) leaves, (6) ovules, (7) 2 DAY whole seeds, and (8) 3 DAP whole seeds. Briefly, first-strand cDNAs were generated by reverse transcription (RT) of 200 ng of total RNA using MMLV reverse transcriptase and an anchor/reverse primer (G primer: 5'-AAGCT$_{11}$G-3' (SEQ ID NO:26) or C primer: 5'-AAGCT$_{11}$C-3' (SEQ ID NO:27)). Aliquots of the first-strand cDNAs were used as templates for the polymerase chain reaction (PCR) using combinations of forward and anchor/reverse primers in the presence of $^{33}$P-dCTP and AmpliTaq® polymerase (Perkin Elmer; Branchburg, N.J.). The forward primers used were: H-AP49, 5'-AAGCTTTAGTCCA-3' (SEQ ID NO:28); H-AP50; 5'-AAGCTTTGAGACT-3' (SEQ ID NO:29); H-AP51, 5'-AAGCTTCGAAATG-3' (SEQ ID NO:30); H-AP52, 5'-AAGCTTGACCTTT-3' (SEQ ID NO:31); H-AP53, 5'-AAGCTTCCTCTAT-3' (SEQ ID NO:32); H-AP54, 5'-AAGCTTTTGAGGT-3' (SEQ ID NO:33); H-AP55, 5'-AAGCTTACGTTAG-3' (SEQ ID NO:34); and H-AP56, 5'-AAGCTTATGAAGG-3' (SEQ ID NO:35), where H-AP refers to the primers supplied by the RNAimage™ kit. The RT-PCR products were size-fractionated in a 6% acrylamide gel and visualized by autoradiography.

Candidate suspensor-specific cDNAs as bands were identified that were (1) over 200 bp in size, (2) present at the same position in lanes containing cDNAs amplified from 6–8 DAP suspensor and micropylar-region mRNAs, and (3) absent in lanes containing cDNAs amplified from chalazal region, embryo proper, and leaf mRNAs. Isolated cDNA fragments were PCR-amplified, cloned into the pCR2.1® vector (Invitrogen: San Diego, Calif.), and sequenced. cDNAs were designated with (1) a C or G, indicating the anchor/reverse primer used, (2) a two-digit number between 49 and 56, indicating the forward primer used, and (3) a one-digit number indicating, the band position on the DD-RT-PCR gel. For example, C541 represents a cDNA band that was amplified by a C anchor/reverse primer, an H-AP54 forward primer, and that was in position number 1 on the DD-RT-PCR gel.

Gel Blot Analysis of PCR-amplified Population cDNAs

For pre-screening of differential display cDNA clones, PCR-amplified cDNAs from different mRNA populations were generated following the procedures of Kelly et al. (1990), with minor modifications. Suspensor (6 DAP), ovule, 2 DAP seed, 3 DAP seed, 6 DAP micropylar region, 6 DAP chalazal region, and leaf total RNAs were isolated. First-strand cDNA was generated from 5 µg of each RNA using MMLV reverse transcriptase and 50 ng/µl of oligo $(dT_{20})$ (SEQ ID NO:36) as primer. The first-strand cDNAs were 3' tailed with poly(dA) using terminal transferase. PCR amplifications were carried out using tailed first-strand cDNAs as templates and 2 µM of $dT_{20}dN$ (SEQ ID NO:37) (where dN=dG, dC, dA, or dT) as primer in 100 µl containing 20 mM Tris (pH 8.4), 50 mM KCl, 1 mM $MgCl_2$, and 0.2 µM dNTPs at 94° C./1 minute, 42° C./2 minutes, and 72° C./5 minutes for 30 cycles, followed by a 10 minute extension at 72° C. A 1 µl aliquot from each reaction was used to perform another round of amplification using the same conditions. The reactions were extracted with phenol/chloroform and precipitated in ethanol. An aliquot equivalent to 1 µg from each reaction was size-fractionated in a 1% agarose gel, which was then used for DNA gel blot analysis according to the procedures of Sambrook et al., supra.

DNA Sequencing and Analysis

DNA sequencing was performed following the dideoxy sequencing procedures recommended by USBiochemicals (Cleveland, Ohio). For genomic clone pG564g7.2.79, unidirectional, nested deletion set was prepared using the Erase-a-Base® system (Promega: Madison, Wis.). Compilation and analysis of sequences were carried out using the Wisconsin Genetics Computer Group (GCG) software. ORFs and exon-intron junctions were identified by using GENSCAN (http://ccr-081.mit.edu/GENSCAN.html; Burge, C., et al., *Journal of Molecular Biology*, 268:78–94 (1997)). The G564 intron-exon junctions were confirmed by comparing the cDNA and gene sequences. Protein sorting sequences were identified using PSORT (http://psort.nibb.ac.jp; Nakai, K., et al., *Genomics*, 14:897–911 (1992)). DNA and protein sequence comparisons were performed using the NCBI Genbank BLAST programs (http://www.ncbi.nlm.nih.gov; Altschul, S. F., et al., *Nucl. Acids Res.*, 25:3389–3402 (1997)). The complete C541 and 0564 cDNA sequences were based on sequences from (1) DD-RT-PCR cDNA clones, (2) cDNA clones isolated from a 5–9 DAP seed cDNA library, and (3) from cDNAs generated from 5' random amplification of cDNA ends (RACE-RT-PCR; Chenchik, A., et al., *Clontechniques*, 10:5–8 (1995)).

In situ Hybridization

In situ hybridization studies were carried out as described by Cox and Goldberg (Cox, K. H., et al., Plant Molecular Biology: a Practical Approach (C. H. Shaw, ed. 1988) pp. 1–34) and Yadegari et al. (Yadegari, R., et al., *Plant Cell*, 6:1713–1729 (1994)) with minor modifications. Briefly, for Scarlet Runner Bean, unfertilized ovules and individual seeds (4–7 DAP) were harvested from pods, and seeds were cut at their chalazal ends before fixing to enhance penetration of the fixative. For tobacco, seeds up to 7 DAP were collected while still attached to the placenta. Older tobacco seeds were separated from the placenta prior to collection. Tissues were fixed overnight at 4° C. in 1% glutaraldehyde solution prepared in 0.1 M phosphate buffer (pH 7.0) (Meyerowitz, E. M., *Plant Mol. Biol. Rep.*, 5:242–250 (1987)), dehydrated, cleared, and embedded in paraffin. Eight to 10 µm sections were hybridized to $^{33}$P-labeled sense or anti-sense RNA probes at a specific activity of 4–5×10$^8$ dpm/µg. After hybridization and emulsion development, sections were stained with 0.05% toluidine blue in 0.05% borate solution. Photographs were taken using either bright-field or dark-field illumination with a compound microscope (Olympus BH2: Olympus Corporation, Lake Success, N.Y.). The photographs were digitized, adjusted for optimum silver grain resolution using the KPT-Equilizer program (Metacreations Corp., Carpinteria, Calif.), and assembled in Adobe Photoshop 5.0 (Adobe Systems Inc., San Jose, Calif.).

Light Microscopy

Bright-field Microscopy

Seeds and unfertilized ovules from Scarlet Runner Bean were collected as described for in situ hybridization and fixed overnight in 5% glutaraldehyde, 0.1 M phosphate buffer (pH 7.0), and 0.01% Triton X-100 at 4° C. After dehydration, samples were embedded in Spurr's (Spurr, 1969) plastic resin (Polysciences: Warrington, Pa.). 1 µm thick sections were stained for 18 to 20 minutes at 42° C. with 0.05% toluidine blue in 0.05% borate solution. Bright-field photographs were taken with Kodak Gold 100 film (ISO 100/21°) using a compound microscope (Olympus BH-2: Olympus Corporation, Lake Success, N.Y.).

Whole Mount Microscopy

Dark-field photographs of seeds were taken using a dissecting microscope (Olympus SZH). Dark-field and bright-field photographs of dissected embryos were taken using a compound microscope (Olympus BH-2).

G564/GUS Construction and Tobacco Plant Transformation

A 21 kb G564 genomic clone was isolated from a Scarlet Runner Bean λDASHII (Stratagene: La Jolla, Calif.) genomic library by screening with a $^{32}$P-labeled G564 cDNA clone. A 7 kb genomic fragment was recloned in pBluescript (Stratagene: La Jolla, Calif.) generating plasmid pG564g7.2.79. 4.8 kb of this plasmid was sequenced to confirm that the sequence of the coding region corresponded to that of the G564 cDNA clone. The entire G564g7.2.79 genomic clone was transferred into pGV1501AN, a pGV1500-derived plant transformation vector (DeBlaere, R., et al., *Methods in Enzymology*, 153:277–292 (1987)).

The region surrounding the ATG start codon in G564g7.2.79 was converted into an SphI endonuclease restriction site by PCR using a T3 primer and a mulagenic oligo (5'-ATTGGACT GCATGCTTACGCTAGTCTGTGCAGAG-3'; SEQ ID NO:38). A 4.2 kb G564 promoter region was cloned in the SphI site upstream of the *E coli* β-Glucoronidase (GUS) gene coding region (Jefferson, R. A., et al., *EMBO. J.*, 6(13):3901–3907 (1987)) in pGEM5GUS. After cloning, the G564 promoter region was re-sequenced. pGEMSGUS was constructed by inserting the GUS coding region and the Ti-plasmid gene 7 3' end from TPI2/GUS gene (Drews, G. N., et al., *Plant Cell*, 4:1383–1404 (1992)) into the NcoI/NotI sites of pGEM5 (Promega: Madison, Wis.). The G564/GUS gene was transferred to the pHYGA (Hygromycin$^R$) plant transformation vector (Klucher, K. M., et al., *Plant Cell*, 8:137–153 (1996)). Tobacco plants were transformed and regenerated using the leaf disk procedure of Horsch et al. (Horsch, et al., *Science*, 227:1229–1231 (1985)).

GUS Histochemical Assay

Transgenic tobacco seeds were harvested at different stages of development (Barker, S. J., et al., *Proc. Natl Acad. Sci. USA*, 85:458–462 (1988)). Embryos were dissected from seeds in 50 mM sodium phosphate (pH 7.0). Dissected embryos were incubated in GUS assay buffer [50 mM sodium phosphate (pH 7.0), 0.1% Triton X-100, 0.5 mM ferricyanide, 0.5 mM ferrocyanide, 2 mM 5-bromo-4chloro-3indolyl-βD-glucuronide] for 30 minutes to 16 hours at room temperature (Jefferson, R. A., et al., *EMBO. J.,* 6(13):3901–3907 (1987)). Embryos were photographed under bright-field or dark-field illumination using a compound BH2 Olympus microscope.

Results

The Scarlet Runner Bean Embryo Forms a "Giant" Suspensor Early in Development

The early developmental stages of Scarlet Runner Bean embryogenesis were characterized to link these stages to morphological markers of the developing seed and to specific times after pollination. Table 1 summarizes the morphological characteristics of the unfertilized ovule and developing seeds from 0 DAP until maturity at 35 DAP. From the ovule until 7 DAP, the seed length increased from 0.75 mm to 2–4 mm and the seed gradually adopted a green color (Table 1). At 11 DAP, the seed began to acquire red pigmentation in the area contiguous to the hilum region (Table 1) and the red color gradually spread and covered the entire seed by 20–25 DAP (Table 1). At 25 DAP, the seed length had increased and was 15 mm (Table 1). At 35 DAP, the mature dry seed had a purple seed coat with magenta streaks near the hilum and was 20 mm in length (Table 1).

The embryonic stages corresponding to seeds at different DAP were characterized from micrographs of longitudinal sections of the micropylar region containing the embryo. In the unfertilized ovule, the egg cell was identified from the orientation of its nucleus and cytoplasmic-dense region towards the chalaza and its vacuolated region towards the micropyle. These cytological features were inverted in the adjacent synergids. The egg cell and synergids were bordered by the central cell at their chalazal ends. At 2 DAP, the embryonic cells were irregularly organized, the apical and basal regions were morphologically indistinguishable, and endosperm had started to form. Just prior to globular stage (4 DAP), the suspensor of the filamentous embryo was distinguished from the embryo proper by its large and irregularly-shaped cells and was approximately 200–250 $\mu$m in length. By contrast, the embryo-proper cells were smaller and more uniform in size and shape.

The suspensor developed two distinct regions—a file of neck cells that connected suspensor to embryo proper and a set of large basal cells that protruded into the seed tissue. In the suspensor-basal region, the number of cells remained constant and the increase in length of the suspensor-basal region was mainly due to cell enlargement. The total suspensor length increased from 500 $\mu$m to 1000 $\mu$m, which was its maximum size (Table 1). The embryo proper increased in cell size and number, and developed from globular stage to heart stage, to cotyledon stage. At the cotyledon stage, the embryo proper was bigger than the suspensor and contained chlorophyll, whereas the suspensor remained white.

Globular embryos were dissected at the rate of approximately 10 per hour and collect separately the embryo-proper and suspensor regions (see Materials and Methods). Twenty micrograms of total RNA was isolated from 250 suspensors and 300 ng total RNA from 200 embryo-proper regions. Together, these data show that the suspensor of Scarlet Runner Bean embryo developed early in seed development (2–11 DAP) and that it was feasible to surgically dissect globular stage embryos into embryo-proper and suspensor regions in order to isolate region-specific embryo RNAs.

DD-RT-PCR of RNA from Micro-dissected Suspensor Regions Yields Two Suspensor-specific cDNA Clones Two strategies were used to identify suspensor-specific mRNAs (Materials and Methods): (1) differential screening of a 5–9 DAP seed cDNA library representing mRNAs present in seeds containing globular-stage embryos and (2) DD-RT-PCR (Liang, P., et al., *Science,* 257:967–971 (1992)) of total RNA from micro-dissected suspensors of globular-stage embryos. Candidates for suspensor-specific cDNA clones were rescreened using: (1) DNA gel blots containing PCR-amplified population cDNAs (Materials and Methods) and (2) RNA gel blots (Materials and Methods).

Differential Screening

In the first approach, two 'seed-specific' candidates for suspensor cDNA clones were identified, designated as SRB8 and SRB13, which hybridized with a 5–9 DAP micropylar-region seed cDNA probe, but not with a leaf cDNA probe (Materials and Methods). SRB8 and SRB13 were sequenced and used BLAST searches (Altschul, S. F., et al., *Nucl. Acids Res.,* 25:3389–3402 (1997)) to show that the encoded proteins are homologous to ribosomal proteins and Bowman-Birk trypsin inhibitor, respectively (Materials and Methods).

DD-RT-PCR Analysis

In the second approach, 25 candidate suspensor-specific cDNAs were identified that were displayed in the lane containing cDNAs amplified from 6 DAP suspensor RNA and in the lane containing cDNAs amplified from RNA of the micropylar half of 6 DAP seed, and that were not present in lanes containing cDNAs amplified from 6 DAP seed chalazal region RNA, globular-stage-embryo-proper RNA, and leaf RNA. All candidate cDNAs longer than 200 bp were cut from the gel, re-amplified, cloned, and sequenced (Materials and Methods).

Total cDNA Gel Blot Analysis

Because the amount of RNA from the suspensor was too limited to screen a large number of clones by standard RNA blot analysis, a DNA gel blot procedure was devised using PCR-amplified population cDNAs (Kelly, A. J., et al., *Plant Cell,* 2:963–972 (1990)) to pre-screen the candidate cDNA clones (Materials and Methods). Total cDNA blot analysis of SRB8 and SRB13 showed that they hybridized with 6 DAP suspensor cDNA, unfertilized ovule, 2 DAP seed, 3 DAP seed, 6 DAP seed micropylar region cDNAs, and 6 DAP seed chalazal region cDNA but not with leaf cDNA. In addition, three DD-RT-PCR cDNAs were identified that hybridized with suspensor and seed micropylar-region cDNAs, but did not hybridize with ovule, seed chalazal-region, and leaf cDNAs. These three clones were designated as G541, G564, and G563, and represented putative suspensor-specific cDNAs. Sequence analysis and homology searches with these cDNAs indicated that they were not related to any protein of known function. However, G564 and C541 proteins were predicted to be secreted or to be targeted to the vacuole, respectively (Materials and Methods).

RNA Gel Blot Analysis

SRB8, SRB13, G564, C541, and G563 probes were hybridized to gel blots, containing 6 DAP suspensor RNA, unfertilized ovule RNA, 2 DAP seed RNA, 3 DAP seed RNA, 6 DAP seed micropylar region RNA, 6 DAP seed chalazal region RNA, and leaf RNA to verify the results of the total cDNA blots. SRB8 and SRB13 probes hybridized with unfertilized ovule and all seed tissue RNAs, but not with leaf RNA. The SRB8 probe yielded a stronger hybridization signal with micropylar-region RNA than with chalazal-region RNA. By contrast, the SRB13 probe produced a stronger signal with chalazal-region RNA as compared to micropyler-region RNA.

G564 and C541 probes did not hybridize with unfertilized ovule, 2 DAP seed, 3 DAP seed, 6 DAP chalazal region, and leaf RNAs. By contrast, G564 and C541 probes yielded a low signal with 6 DAP seed micropylar-region RNA. This signal was strongly amplified with suspensor RNA isolated from 6 DAP micropylar-region seed, suggesting that the lower signal with 6 DAP seed micropylar-region RNA was caused by dilution of the suspensor RNA by non-embryonic seed tissue RNA. G563 produced a similar hybridization pattern, but yielded equal hybridization signals with suspensor and 6 DAP micropylar RNAs. Together, these data showed that during seed development different patterns and levels of RNA accumulation occur. In addition, the higher hybridization signals from G564 and C541 probes with suspensor RNA versus micropylar RNA suggested that G564 and C541 cDNAs represent suspensor-specific mRNAs.

G564 and C541 are Suspensor-specific Markers

In situ hybridization was used to visualize directly regions that the G564, C541, G563, SRB8, and SRB13 mRNAs were localized in unfertilized ovules and 7 DAP seeds.

Localization of G564 and C541 mRNA

Dark field images of 7 DAP embryo sections hybridized with G564 and C541 anti-mRNA probes showed that G564 and C541 mRNAs were localized specifically in the suspensor. The G564 hybridization signal was spread evenly over the suspensor neck and basal cells. The C541 signal, on the other hand, was higher in the suspensor basal cells than in the suspensor neck cells. In addition, compared to the G564 probe, the C541 probe produced fewer hybridization grains, suggesting that the C541 mRNA is present at a lower prevalence than the G564 mRNA. No hybridization signal was detected above background level in the embryo proper, nor in any other cell or tissue of the developing seed. No G564 or C541 hybridization signals above background were observed in any unfertilized ovule cell or tissue type, similar to that observed with the sense control probe.

Localization of G563 mRNA

The G563 anti-mRNA probe hybridized specifically with transcripts in the endothelial layer surrounding the embryo but not in the embryo or any other seed tissue. The G563 hybridization signal was first detected at 3 DAP. By contrast, no hybridization signal above background level was obtained in the chalazal endotheium, nor in the endothelium or any other tissue of the unfertilized ovule.

Localization of SRB8 and SRB 13 mRNAs

The SRB8 and SRB13 mRNAs were highly prevalent within unfertilized ovule and seed, and were not localized exclusively within the suspensor. However, both mRNAs displayed different and changing accumulation patterns within pre- and post-fertilization ovulelseed. In the ovule, the SRB8 anti-mRNA probe detected transcripts in the endotheium and the epidermal layer. In addition, in the developing seed, SRBS hybridization grains accumulated to a high level in the endosperm and in the embryo. A stronger SRB8 hybridization signal was observed in the embryo proper than in the suspensor. The SRB13 anti-mRNA probe yielded hybridization signal in the outer integument of the unfertilized ovule and seed. Although SRB13 mRNA was present in the suspensor, its prevalence was not as high as in the integument.

Taken together, these data show that in the unfertilized ovule and developing seed various and partially overlapping transcript-accumulation patterns occur that change after fertilization has occurred. In addition, these results show that G563 mRNA is a marker for seed micropylar endothelium and that G564 and C541 mRNAs are suspensor-specific markers.

G564 and C541 Are Markers for the Basal-region of the Four-cell Embryo

In situ hybridization was used to investigate the accumulation pattern of G564 and C541 mRNAs during embryo development. Before fertilization, no hybridization signal was obtained with either G564 or C541 anti-mRNA probes in the egg or the synergids, even after a 6–9 month emulsion exposure. After fertilization, and before the suspensor and embryo-proper region were morphologically distinguishable (2 DAP), the G564 and C541 anti-mRNA probes detected transcripts exclusively in the two basal cells of the four-cell embryo, but did not detect any transcripts in the two apical cells. From early globular stage, after 3 DAP, G564 and C541 transcripts were detectable in the suspensor and not in the embryo proper. In addition, the higher concentration of C541 mRNA in the suspensor-basal region, compared with the suspensor-neck region.

The G564 mRNA accumulation pattern at later stages of embryo development was investigated in 23 DAP early-maturation-stage embryos. The dark field image of an axis and cotyledon section that was hybridized with a G564 anti-mRNA probe showed that G564 transcripts accumulated in the axis, but not in the cotyledons or in any other seed tissue.

Together, these data show that late G564 transcripts mark the embryo axis, and that G564 and C541 mRNAs are suspensor-specific markers. In addition, these results show that within two cell divisions after fertilization, G564 and C541 mRNAs mark the two basal cells of the four-cell embryo.

Basal-region Specific G564 mRNA Accumulation Is Transcriptionally Regulated

The G564 gene was isolated from a Scarlet Runner Bean genomic library to determine whether the basal-region-specific and suspensor-specific G564 mRNA accumulation pattern was regulated at the transcriptional or post-transcriptional levels. A 6.99 kb genomic fragment from the Scarlet Runner Bean was isolated. The G564 coding region was 659 bp long, consisted of 2 exons of 107 and 388 bp, and contained one 164 bp intron. The 5' and 3' regions, included in the genomic fragment, were 4242 bp and 2085 bp in length respectively. In the 5' region, another gene, at position −4214 to −2588, similar to the *Arabidopsis* Pol3 gene (accession no. AC005561) was identified.

G564 mRNA Localization in Transgenic Tobacco Embryos Carrying the Scarlet Runner Bean G564 Gene The Scarlet Runner Bean G564 genomic clone was introduced into tobacco and localized G564 mRNA accumulation in transgenic embryos to investigate whether the basal-region-specific and suspensor-specific G564 mRNA accumulation patterns were conserved in a heterologous plant. At the pie-globular embryo stage, similar to the Scarlet Runner Bean embryo, the G564 mRNA accumulated specifically in the embryo basal region, but not in the apical region. At this stage of tobacco embryo development the suspensor is distinguishable from the embryo proper. At the globular stage, the G564 mRNA was detected in the suspensor and in the hypophyseal region of the embryo proper. In heart- and torpedo-stage embryos, G564 transcripts accumulated in the axis similar to the G564 mRNA accumulation pattern in the Scarlet Runner Bean early maturation-stage embryo. In addition, G564 transcripts accumulated in the endosperm. No hybridization signal above background level was detected in non-transformed tobacco embryos. Together, these results suggested that the basal-region-specific and suspensor-specific G564 mRNA accumulation pattern is conserved across the plant kingdom and that all regulatory elements for correct suspensor-specific G564 mRNA accumulation are contained within the 6.99 kb G564 genomic clone. Analysis of the gene sequence indicated that the coding sequence was interrupted by an intron. As measured from the first identified nucleotide of the G654 cDNA sequence (i.e., position 4242 of SEQ ID NO:2), the first exon is located from positions 1 to 107 and the second exon from positions 271–659.

G564/GUS Expression in Transgenic Tobacco Embryos

A chimeric G564-promoter/GUS gene was introduced (see Materials and Methods) into tobacco and accumulation of GUS mRNA and GUS enzyme activity in transgenic tobacco embryos was monitored to study G564 transcription regulation. The G564/GUS gene was active in the two suspensor cells of the five-cell pre-globular embryo. In the embryo proper, by contrast, no GUS activity was detected. No GUS hybridization grains were detected above background level, indicating that—in the suspensor—GUS mRNA had accumulated below the detection level of the in situ hybridization. At globular stage, both GUS activity and GUS mRNA accumulation were detectable in the suspensor and in the hypophyseal region of the embryo proper. At heart and torpedo stages, GUS activity and mRNA accumulation were detectable in the axis. GUS transcripts were also detected in the endosperm. Together, these data show that in transgenic tobacco embryos, G564/GUS expression and GUS mRNA accumulation follow the same developmental pattern as was observed for G564 transcripts in transgenic tobacco embryos carrying the entire G564 gene and as observed in Scarlet Runner Bean embryos. In addition, these results indicate that the G564 mRNA basal-region-specific and suspensor-specific accumulation is controlled at the transcriptional level by the 4.2 kb 5' upstream region of the G564 gene, and that the transcription-regulatory function of this region was conserved between plant species.

Figure 6:
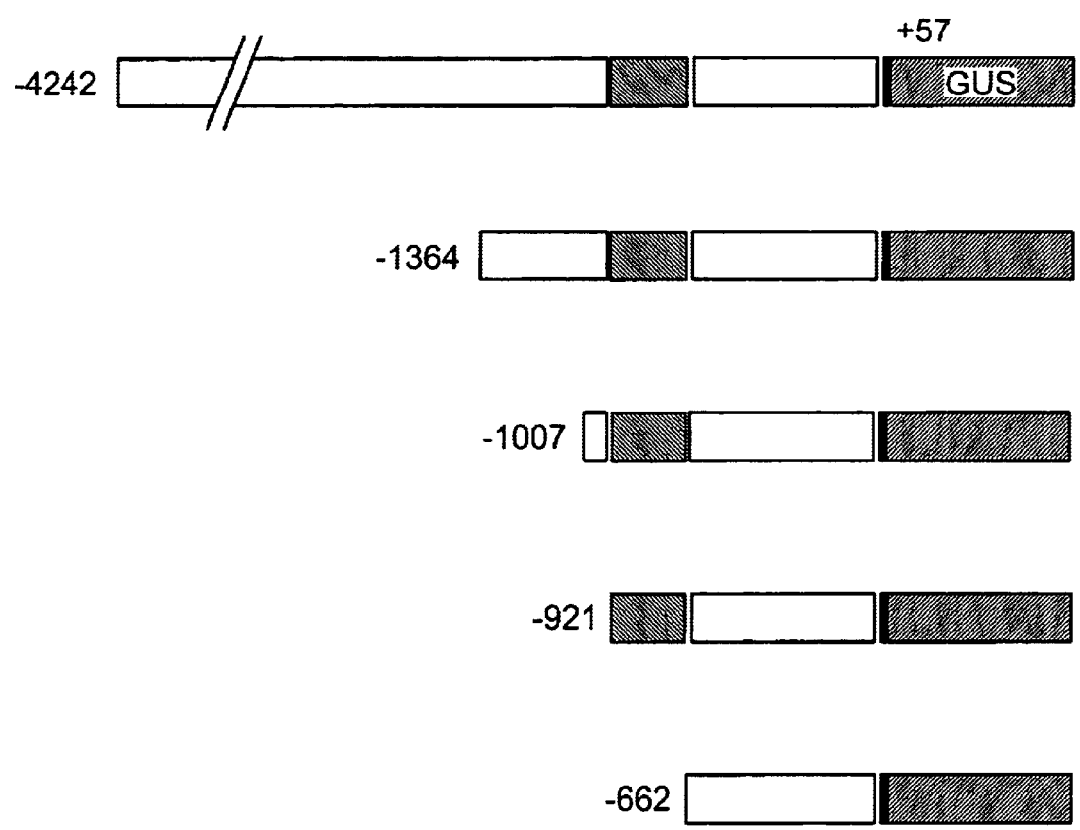
FIG. 6 is a schematic representation of a deletion analysis of the Scarlet Runner Bean G654 promoter. Suspensor-specific GUS expression was observed in all constructs except the shortest (deleted from the 5' end to position −662). This figure demonstrates that a suspensor-specific cis-acting sequence is located between positions −921 and −662 (corresponding to nucleotides 3324–3580 of SEQ ID NO:2).

To further analyze the G564 promoter, a series of 5' deletions were constructed and tested for suspensor-specific activity (FIG. 6). Promoters with deletions of nucleotides −4242 to −921 retained suspensor-specific GUS activity, while promoters with deletions up to nucleotide −662 did not have GUS activity in suspensor cells. These results indicate that a suspensor-specific control element is present between positions −921 and −662.

Sequence analysis of the Scarlet Runner Bean G564 promoter region revealed four sequences of approximately 100 base pairs long within the promoter region. Each repeat is highly homologous to the other repeats. These repeats can be found between positions −1327 to −1225, −1206 to −1103, −1030 to −928, and −908 to −800. Each homologous repeat contains either the sequence GAAAAGCGAA (SEQ ID NO:10) or the related sequence GAAAAGTGAA (SEQ ID NO:11).

Figure 7:
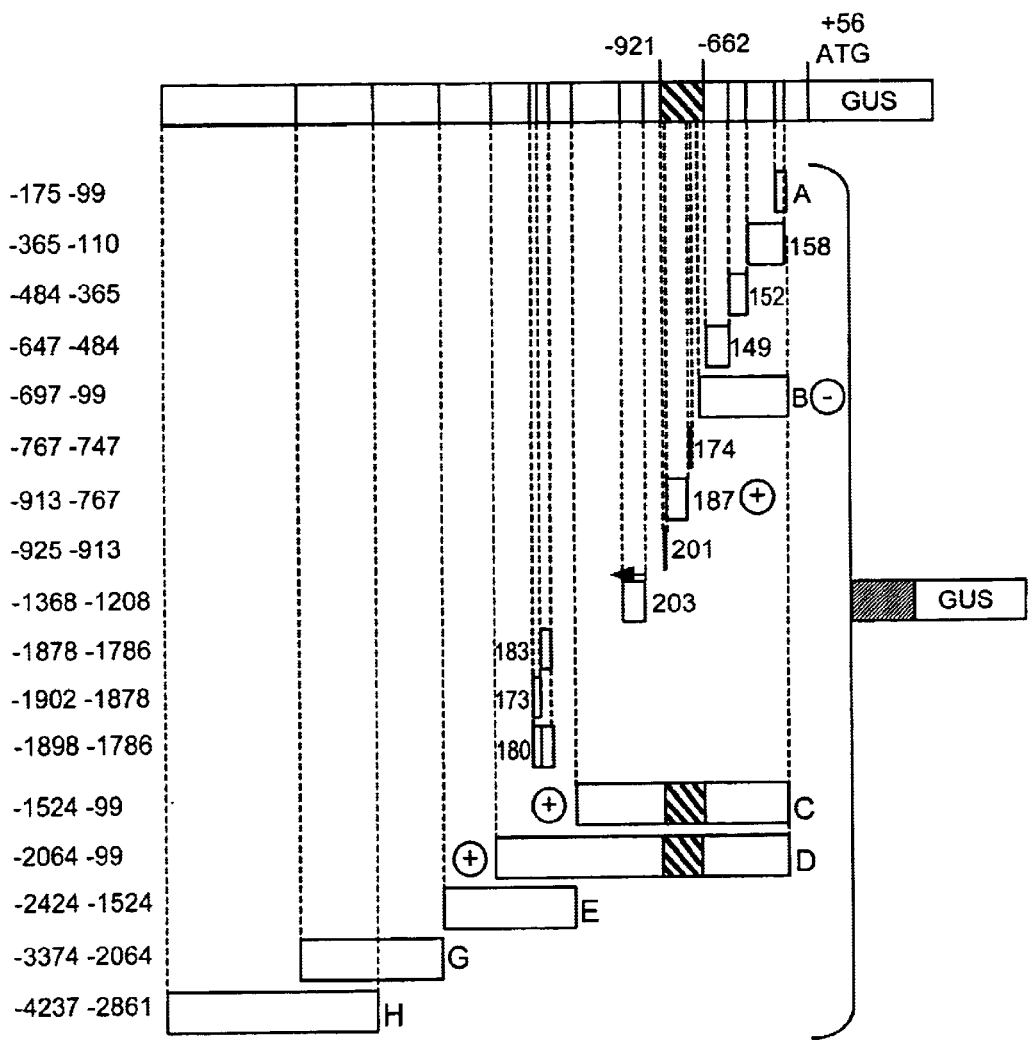
FIG. 7 is a schematic representation of a series of promoter fragments from the Scarlet Runner Bean G564 promoter region fused to a minimal 35S promoter and GUS gene.

Additional promoter fragments from the Scarlet Runner Bean G564 promoter were isolated and linked to a minimal 35S promoter operably linked to the GUS gene. As indicated in FIG. 7, two fragments encompassing the region between −921 and −662 resulted in GUS activity in the suspensor cell. These fragments were from positions −1524 through −99 and −2064 through −99. In addition, a 187 base pair fragment (positions −913 through −767 of FIG. 1) linked to the minimal 35S promoter lead to GUS expression in the suspensor cell. This result suggests that at least one suspensor-specific control element is located within the 187 base pair fragment.

A comparison of the Scarlet Runner Bean G564 promoter (SEQ ID NO:1) and the Scarlet Runner Bean C541 promoter identified a conserved 10 base pair sequence which may confer suspensor-specific activity. Supporting this assertion, the sequence, GAAAAGCGAA (SEQ ID NO:10), is found at positions −846 to −837, i.e., within the area which the deletion results indicate controls suspensor-specific activity. Identical motifs can also be found at positions −1144 through −1135 and between −713 through −704 of FIG. 1. The motif is also found at positions −684 through −675 of the Scarlet Runner Bean C541 promoter region (FIG. 4). Interestingly, the *Arabidopsis* G564 ortholog promoter region comprises a motif (GAAAAGCCAA—SEQ ID NO:12) that is highly homologous to SEQ ID NO:10.

As a further analysis, a series of embryo-specific promoters that do not initiate transcription in the suspensor cell were screened for SEQ ID NO:10. None of the promoters screened (Kti1 (Accession No. 45035), Kti2 (Accession No. S45035), Kti3 (Accession No. K00821) or the lectin promoter (Accession No. S45092)) contained SEQ ID NO:10.

A listing of other motifs identified in the region defined by −921 to −662 of the Scarlet Runner Bean G564 promoter region is provided as FIG. 8.

Discussion

The Scarlet Runner Bean embryo was used as a model system to investigate gene expression programs during early embryogenesis. Two suspensor-specific mRNAs designated as G564 and C541 were identified. In four-cell embryos, G564 and C541 mRNAs accumulate exclusively in the two basal cells, but are not detectable in the two apical cells. A chimeric G564/GUS reporter gene is transcribed specifically in two basal cells of transgenic tobacco embryos at a similar stage (five-cell). From these results it is concluded that as early as the four-cell embryo stage the apical and basal cells transcribe different gene sets and are specified at the molecular level.

The Scarlet Runner Bean Suspensor Is a Novel System to Study the Mechanisms Regulating Specification of the Basal Region of the Early Plant Embryo Scarlet Runner Bean has been used historically to study the role of the suspensor in embryo development. The suspensor size facilitated its micro-dissection (FIG. 1O-Q) and rendered it accessible for physiological and cytological studies (Nagl, W., Z. *Pflanzenphysiol.*, 73:1–44(1974): Sussex, I., et al., *Caryologia*, 25:261–272 (1973); Yeung, E. C., et al., *Protoplasma*, 94:19–40 (1978); Yeung, E. C., et al., *Plant Cell*, 5:1371–1381 (1993); Yeung, E. C., et al., *Zeitschrift fur Pflanzenphysiology*, 91:423–433 (1979)). Because the suspensor is simple, terminally differentiated, and only few cell generations removed from the basal cell, we have adopted this model to study the mechanisms specifying basal-cell fate. Scarlet Runner Bean suspensors were collected separately from embryo propers and used the suspensors to identify two genes, G564 and C541, that are transcribed specifically in the suspensor and in the basal region of the embryo shortly after division of the zygote. The G564 promoter maintains transcriptional activity in suspensors of tobacco embryos. Therefore, this promoter can be used to identify regulatory genes and thus as an entry point to penetrate the regulatory circuits that control basal cell specification. In addition, *Arabidopsis* genes corresponding to G564 and C541 were identified (SEQ ID NO:4 and SEQ ID NO:8, respectively). We can use these genes to find mutants important for suspensor function in embryo development. Thus, the *Arabidopsis* model system is complemented by the Scarlet Runner Bean suspensor as a model to investigate the earliest events in plant embryogenesis.

A Mosaic of Gene Expression Programs Is Active During Seed Development

In flowering plants, fusion of the sperm cells with both the egg cell and central cell initiates embryo and endosperm development, respectively (Table 1). In addition, fertilization causes the integument and the endothelium to differentiate and to contribute to the development of the seed (Table 1 and Embryology of Angiosperms (Johri, B. M., ed. 1984); Miller, S. S., et al., *Annals of Botany London,* 84:297–304 (1999); Embryogensis in Angiosperms: A Developmental and Experimental Study (Raghavan, V., ed. 1986)). Simultaneously, a cascade of different gene expression programs is initiated that are correlated with the various events occurring during embryo and seed development (Goldberg, R. B., et al., *Cell,* 56:149–60 (1989); Goldberg, R. B., et al., *Science,* 266:605–614 (1994)). For example, SRB8 mRNA accumulates in the ovule chalazal endotheliun and after fertilization, it accumulates in endosperm and embryo proper. SRB8 is homologous to a ribosomal protein L10A indicating a greater need for ribosome and protein synthesis in these tissues before and during early seed development SRB13 transcripts accumulate in the integuments and, after fertilization, in the seed coat and to a lesser extent in the developing embryo. SRB13 is homologous to a Bowman-Birk trypsin inhibitor illustrating the protective function of integuments and seed coat.

G563 mRNA starts to accumulate specifically at 3 DAP in the seed micropylar endothelium surrounding the developing embryo. The micropylar-endotheium cell layer is suggested to function as an embryo-nursing tissue by exchanging metabolites with the suspensor via extensive cell wall ingrowths that appear at 3 DAP (Natesh, S., et al., *Embryology of angiosperms*, (ed. B. M. Johri) pp. 377–444, Berlin: Springer Verlag (1984); Yeung, E. C., et al., *Protoplasma,* 94:19–40 (1978); Yeung, E. C., et al., *Can. J. Bot.,* 57:120–136 (1979)). Probably because of this tight contact between endothelium and suspensor, some residual endotheial cells were present in our hand-dissected suspensor preparations, which explains why we were able to identify G563 as a micropylar-endothelium-specific transcript. The correlation of G563 transcript accumulation with the appearance of cell wall ingrowths contiguous to the suspensor of the developing embryo suggests that G563 marks the specification of the micropylar endotheium as an embryo-nursing tissue. Although the function of the predicted G563 protein is unknown, its high glycine and praline content (47.5 and 12.5 percent, respectively) suggests a structural function perhaps in the formation of the specialized cell wall ingrowths.

G564 and C541 transcripts accumulate specifically in the suspensor. G564 transcripts are distributed evenly over the whole suspensor, while C541 transcripts accumulate to a higher concentration in the suspensor-basal region than in the suspensor-neck region. Based on physiological and cytological studies, the main activities of the suspensor are importing, producing and transporting nutrients and growth regulators to the developing embryo proper (Alpi, A., et al., *Planta,* 147:225–228 (1979); Brady, T., *Cell Diferentiation,* 2:65–75 (1973); Ceccarelli, N., et al., *Zeitschrift fur Pflanzenphysiology,* 102:37–44(1981); Clutter, M., et al., *Journal of Cell Biology,* 63:1097–1102 (1974); Schnepf, E., et al., *Protoplasma,* 69:133–143 (1970); Sussex, I., et al., *Caryologia,* 25:261–272 (1973); Yeung, E. C., et al., *Can. J. Bot.,* 57:120–136 (1979); Yeung, E. C., et al., *Plant Cell,* 5:1371–1381 (1993)). The exact functions of G564 and C541 in these activities are unknown, but the fact that G564 protein is predicted to be secreted suggests that it might play a role in metabolite exchange in the intercellular space of the cell wall ingrowths. C541 is predicted to be targeted to the vacuole, which explains the higher concentration of C541 mRNA in the highly vacuolate suspensor-basal region.

Together, the different SRB8, SRB13, G563, G564, and C541 mRNA accumulation patterns illustrate that an array of different gene regulatory programs is active to make a seed. However, how these programs are regulated coordinately remains to be established.

Differentiation of Early-embryo Apical and Basal Regions Is Marked by the Accumulation of Different Transcript Sets The suspensor is derived from the basal cell of the two-cell embryo, however it is not known what mechanisms direct the basal cell to become specified and develop into a suspensor, nor is it known when these mechanisms are active. To gain entry into the mechanisms regulating suspensor development and thus into the mechanisms regulating apical-basal cell specification events, two suspensor-specific transcripts were identified, designated as G564 and C541. The G564 and C541 transcripts first accumulate in the two basal cells of the four-cell embryo, before the suspensor is morphologically distinguishable and thus marking the embryo-basal region for suspensor specification. By contrast, in *Arabidopsis* pro-embryos a homeobox mRNA, designated as ATML1, has been found to accumulate selectively in the apical cell (Lu et al., *Plant Cell* 8(12):2155–68 (1996). Together, this shows that at the four-cell embryo stage the apical and basal regions have differentiated and that this specification process is marked by accumulation of different transcript sets. In addition, it indicates that the mechanisms activating the apical and basal-region-specification processes are active earlier either in he two-cell embryo or in the zygote or egg.

Apical and Basal-region Specific Accumulation of mRNA Is Caused by Specific Transcriptional Programs G564 mRNA accumulation pattern in the basal-region and the suspensor is similar to that in Scarlet Runner Bean embryos. This shows that the 6.99 kb G564 genomic clone is a marker for the specification mechanism of the basal region of the four-cell embryo and that within this 6.99 kb genomic fragment an elements are present that are recognized by this mechanism. In addition, we conclude that although early-embryo cell division patterns are different between Scarlet Runner Bean and tobacco (Kaplan, D. R., et al., *Plant Cell,* 9:1903–1919 (1997); Natesh, S., et al., Embryology of Angiosperms, (B. M. Johri, ed. 1984) 377–444), the mechanisms specifying cell fate are conserved (Goldberg, R. B., et al., *Science,* 266:605–614 (1994)).

In transgenic tobacco embryos containing the chimeric G564/GUS gene, GUS enzyme activity in a basal-region-specific and suspensor-specific pattern are similar to the G564 mRNA accumulation pattern in Scarlet Runner Bean embryos and G564 transgenic tobacco embryos. This shows that the mechanism regulating basal-region specific G564 mRNA accumulation works at the transcriptional level. Therefore, the differentiation of the basal and the apical regions of the early embryo, which is marked by differential accumulation of transcript sets, is caused by specific apical and basal-region transcription programs. Initial analysis was performed of the basal-region transcription program by dissecting the GYM promoter for cis-regulatory elements to identify its regulatory factors. Preliminary data indicate that the elements directing basal-region-specific transcription are present at −921 to −662.

A Model for the Mechanism of Specification fo the Apical and Basal Cell of the Two-cell Embryo How is the G564 transcriptional program activated specifically in the embryo basal region and how does this provide clues to the general mechanism specifying basal-cell fate? A possible explanation might reside in the apical-basal polarized cyto-architecture of the egg cell and zygote (FIG. 1E and Willemse, M. T. M., et al., Embryology of Angiosperms, (B. M. Johri, ed. 1984) 159–196). The asymmetric distribution of cytoplasm, and/or its contents within the egg and/or zygote may play a role in activating specific apical and basal-region transcription programs (Goldberg, R. B., et al., *Science*, 266:605–614 (1994)). Based on this suggestion, a simple model is proposed for the specification of basal cells leading to suspensor differentiation. This model assumes that there is an asymmetric distribution of "morphogenetic factors" (e.g. transcription factors) within either the egg cell or the zygote or both. In addition, it assumes that the basal cell (and suspensor) is specified autonomously as a consequence of inheriting the 'morphogenetic factors' following zygotic division. These factors trigger a cascade of events leading to the transcription of basal-region-specific genes, like G564, and suspensor differentiation (FIG. 8).

The model outlined above is consistent with analogous autonomous specification processes that occur for specific cell types during embryo development in various animal systems (Davidson, E. H., et al., *Development*, 125:3269–3290 (1998)). In plants, this model predicts that the embryobasal-region-specific transcription of G564 (FIGS. 5B, 7B, J) is programmed by one or more basalcell-specific transcription factors, and that these transcription factors are derived initially from the basal region of the egg cell or zygote. It is possible that these regulatory factors are bound by the cytoskeleton to the basal pole of the egg and/or the zygote and that these factors automatically become pan of the basal cell after zygote division. This would be similar to the mechanism responsible for targeting factors to unique intracellular cytoplasmic locations in animal embryos (Lall, S., et al., *Cell*, 98:171–180 (1999); Yisreali, J. K., et al., *Development*, 108:289–298 (1990)) and to the mechanism by which the polarized axis is fixed in *Fucus* eggs (Kropf, D. L., *Plant Cell*, 9:1011–1020 (1997); Quatrano, R., *Cold Spring Harbor Symposia on Quantitative Biology*, 57:65–70 (1997)).

Alternatively, it is also possible that a signalling mechanism is responsible for basal cell specification similar to that which establishes dorsal/ventral polarity in *Drosophila* embryos (Davidson, E. H., et al., *Development*, 125:3269–3290 (1998); Sen, J., et al., *Cell*, 95:471–481 (1998)). In this case, a signal derived from the maternal seed tissues contiguous with the basal cell (e.g. endotheium) would interact with a basal cell ligand which would then trigger a signal transduction cascade leading to transcription of basal-region-specific genes like G564 and suspensor differentiation. One prediction of this model is that the transcription factors which activate G564 transcription should be present in both the apical and basal cells of the embryo, but remain inactive within the apical cell (Davidson, E. H., et al., *Development*, 125:3269–3290 (1998)).

TABLE 1

Description of Scarlet Runner Bean seed development stages.

| Stage | DAPs after Pollination (DAP) | Suspensor length | Seed length | Seed color |
|---|---|---|---|---|
| Ovule | 0 | — | <0.75 mm | white |
| Proembryo | 1 to 4 | <50 μm to 250 μm | 0.75 to 1.5 mm | pale green |
| Globular | 5 to 9 | 320 μm to 600 μm | 2 to 4 mm | green |
| Heart | 10 to 12 | 700 μm to 900 μm | 4.5 to 6 mm | green with red pigment contiguous to the hilum |
| Early cotyledon | 13 to 17 | ~1000 μm | 7 to 9 mm | green with heavy red pigment in the area surrounding the hilum |
| Late cotyledon | ~25 | ND | ~15 mm | scarlet red |
| Mature | ~30 to 35 | ND | ~20 mm | purple |

ND, not determined

It is understood that the example and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. An isolated promoter polynucleotide which specifically initiates transcription in a plant suspensor cell and/or basal region of a plant embryo, the promoter polynucleotide comprising a promoter control element comprising nucleotides 3329–3475 of SEQ ID NO:1 (nucleotides −913 to −767 displayed in FIG. 2).

2. A method of introducing an isolated polynucleotide into a host cell comprising:
   (a) providing an isolated polynucleotide according to claim 1; and
   (b) contacting the polynucleotide with the host cell under conditions that permit insertion of the polynucleotide into the host cell.

3. The isolated promoter polynucleotide of claim 1, wherein the promoter polynucleotide comprises SEQ ID NO:1.

4. The isolated promoter polynucleotide of claim 1, wherein the promoter polynucleotide comprises a heterologous basal promoter sequence.

5. The isolated promoter polynucleotide of claim 4, wherein the heterologous basal promoter comprises a minimal CaMV 35S promoter.

6. An expression cassette comprising the promoter polynucleotide of claim 1 operably linked to a heterologous polynucleotide.

7. The expression cassette of claim 6, wherein the promoter polynucleotide comprises a heterologous basal promoter sequence.

8. The expression cassette of claim 7, wherein the promoter polynucleotide comprises a minimal CaMV 35S promoter.

9. The expression cassette of claim 6, wherein the promoter polynucleotide comprises SEQ ID NO:1.

10. A vector comprising the expression cassette of claim 6.

11. A host cell comprising the expression cassette of claim 6.

12. The host cell of claim 6, wherein the host cell is a plant cell.

13. A plant comprising the expression cassette of claim 6.

* * * * *

SEQUENCE LISTING

```
<160> NUMBER OF SEQ ID NOS: 38

<210> SEQ ID NO 1
<211> LENGTH: 4298
<212> TYPE: DNA
<213> ORGANISM: Phaseolus coccineus
<220> FEATURE:
<221> NAME/KEY: promoter
<222> LOCATION: (1)..(4298)
<223> OTHER INFORMATION: Scarlet Runner Bean G654 promoter
<220> FEATURE:
<221> NAME/KEY: modified_base
<222> LOCATION: (1)..(4298)
<223> OTHER INFORMATION: n = g, a, c or t
```

<400> SEQUENCE: 1

```
gcatgcactg ccacaagtag tgaactcatg gttttacctc ctcaagtaga aaaccttttg      60
agtgaatttg aagatttatt ctcccaagaa ggacccattg ggcttcctcc tcttaggggg     120
atagaacatc aaattgactt tataccgggg gcaagcctac caaataggcc tccttataga    180
accaaccccg aggaaacaaa ggagataaaa tcacaagttc aagacttgtt ggagaagggt    240
tgggttcaaa agagcctaag cccttgtgct gtacctgtct tgttggtgcc aaaaaaagat    300
ggaaaatggc gtatgtgttg tgattgtaga gcaatcaaca acatcaccat caagtatagg    360
catccaatcc caaggcttga cgatatgctt gatgaattgc atgggtcaac tctattctcc    420
aaaattgacc ttaaaagtgg atatcaccaa attcgaatca aggagggtga tgagtggaaa    480
accgctttta agaccaaatt tggattatat gagtggttgg tgatgcccct tggtcttact    540
aacgctccaa gtacattcat gaggcttatg aatcacacct gagggattg tataggtaaa     600
tatgtagtag tttattttga tgatatcctta gtatatagta aaaccctaga agaccatcta    660
agtcacctta gggaagttct tctagttctt aggaaaaata gtcttttttgc caatagggat    720
aagtgtacct tttgtgtaga tagcgtagtc tttttaggct ttatagtaaa ccaaaagggg    780
gtgcatgtag atcccgagaa aatcaaagcc atccgcgagt ggccaactcc acaaaatgta    840
agtgatgtga gaagttttca tgggttagct agcttctata gaaggtttgt tcccaatttt    900
tctagcctag cttctcccctt gaatgaactt gtaaaaaaag atgttgcatt tgttggaat    960
gaaaagcatg agcaagcctt tcaaaggcta aagctcact caccaatgca cccatccctat   1020
ctcttccaaa ttttttccaaa cttttggaga tagagtgtga tgcatcggga gtaggcatag   1080
tgcggttttg ttgcaaggtg gacaccccctt gcttatttta gtgaaaaact ccatggtgcc   1140
accctcacta ccccacctat gacaaagact ctatgctctt gtgcgaccct aaagacttgg   1200
ggaacactac cttgngtccc aaagaatttg gntatccata gtgatcacga gtctttaaaa   1260
tatttaaagg gccaacacaa gctcaataag agacatgcta aatggatgga atttcttgaa   1320
caatttcctt atgtcatcaa atacaagaaa gggagcacca atatagtggc cgatgctctt   1380
tctagacggc acactctctt tcaaaacta ggtgcccaaa ttcttggatt tgaccacata   1440
agagagcttt atcaagaaga tcaagaactc tcatccatct atgcccaatg tctacataga   1500
gcacaaggag gttactatgt gtccgaggga tatcttttta aagaaggaaa actttgcatt   1560
ccccaaggaa cacatagaaa actccttgtc aaagaatcac atgaagggg actcatgggc   1620
catttttggag ttgataaaac tctagacttt taaaagcaaa attttgttgg ccacacatga   1680
ggaaagatgt ccacgacatt gtctagagta tctcatgttt aaaagcaaag tctagaacaa   1740
tgccgctgga ctctacaccc ctttgccgat tgcaaagctc cttgtgaaga cattagcatg   1800
gatttcattt taggacttcc taggactgca agaggccatg actctatctt tgtggtagtg   1860
gaccgttttta gcaaaatgtc tcactttatt ccatgccaca agtagatga tgctcaaaat    1920
atttctaaac tcttctttag agaagtggtg agactccatg gtctccctag aagtatagtg   1980
tccgatagag atcaccttaa atatataatt atacacttgt ttttttttctc ttttttattt   2040
tatcaagtaa aaagtatttg ttctagatta ttatgagtat atacttactt tctgtatttc   2100
atttctttct attttttatg acgatgaaat ttcttattat atccagactt ttcatatata   2160
tttttatttc ttttccatct agatgctctg tactttcctt cagttgaaat ttccactctc   2220
caacaaaaca tcattcaagt tttgtataac actgtgacgt taaccagtta aaataagaaa   2280
atcatgtaat ataaattatt tcagtagata ttttagaatt acaaatacga taaataatta   2340
```

```
aatttaaaaa attattaaac aatgaatttt tttggaaatt aatataaaac ttagacttgt    2400
ggtttcttca ttcagtcaaa acctttttct attgtgtggc gtgtgcgtga acatcgaatt    2460
tgggtgcttt atgccgcttt atcttcatct gcaccttcaa attaataatt taattccgga    2520
aaataataaa cccacacact gttttatgca tatattaaga taaataaaag agaactattt    2580
taaagaatat aaaataataa atgtaacaaa tgatgtcact aaagaagaaa aaattaaca     2640 agaattgtaa tatatttctt tatgaaatgt tttgtgcatt accgagagag gtcgaacatg    2700
atacacgcaa gcatctaact agtttggtaa ttcctttca acatcgntaa gcacatcaca    2760
ctaaaattac tttaaataga taaattagat tcaattggat gacattaatt tataatactc    2820
tatccaaaat tataactata aataaaaagt tattttaga aaataagtaa tgaaaattta    2880
attctaaaat ttataacact tttatgctgt gtttgtttcg aagcatagaa aaataaaaag    2940
ttattgttgg gaatgaaaag tgaagaaaat catgtaataa aaacaaaatg acacgacaat    3000
caaaaaaaaa gttttcatgc aaaacttttt tcaaaattta cacttttatg atgtgtttgt    3060
ttcgaagtgt agaaaaacga aaagttatta ttggtaatga aaagcgaaga aaatcacgta    3120
ataaaaacaa agcaagatgg cacgacaatc aaaaaaaagt ttctacacaa aactttattc    3180
aaaatttaca acacttttat gttgttgttt gtttccgagg tatagaaaaa caagaatta    3240 gtgttggtaa tgaaaagtga agaaaaccat gtaatgaaaa caaaatggca cgacaatcaa    3300
aaaaagtttt cacgcaaaat tttcttcaaa atttataaca ttttcatgtt gtgtttgttt    3360
caaagcctag aaaaacgaag agttactatt ggtaatgaaa agcgaagaaa accacataat    3420
aaaaacaaaa tggcacgaca atcaagaaaa agttttcaca caaaactttt tcaaaattt    3480 actatgttta tttcgaaatt tagaaaaacg aagagttatt attagtaatg aaaagcgaag    3540
aaaactacgt aataaaaaac aaaatggcac gacaataaaa aaagttttca cgcaaaattt    3600
tcttggtgcg cagaaagtta tatatattaa ttaattaatt tcatttact ttttccctt    3660 tttattttaa agttaaatta ttattatttt catttaaaat ataatatta tttaaatata    3720 aaaaatataa ccttaatcaa aacaaagcct aatctaaaa tttacaacac ttttaacctt    3780
aaaattaact ttaaaaggaa aatgatagtg tgacaactaa aaaagttgta tacaaccctg    3840
tcataggttt agaaataaat atatataata aagagtaaat ttgtaattaa atgatataaa    3900
aaagtattaa aataataata tttagagtag taatatggtt gtataaaaaa atgtggttgt    3960
ccatatatca ttattcactt taaaatatca tgacaaatat tttcaccgaa agatggaaag    4020
aacgaaaaga gcgttggata atggaaaaat acaagcaatc tccctccagt actttgcata    4080
acattttgta ttagtgatga gttttttatc atatatattt agaatatagg aaaattttag    4140
aatcacgtgg atagctatat aatagtaata ttttaattta taatgtagtt gattttattt    4200
gtcaactggt atacataaat atgtgttgat agtgggtgac ttgtggctta agaaatgtc    4260 cagaggctga caacaactct gcacagacta gcgtaaac                            4298
```

<210> SEQ ID NO 2
<211> LENGTH: 4921
<212> TYPE: DNA
<213> ORGANISM: Phaseolus coccineus
<220> FEATURE:
<223> OTHER INFORMATION: Scarlet Runner Bean G654 genomic region
<220> FEATURE:
<221> NAME/KEY: exon
<222> LOCATION: (4299)..(4346)
<220> FEATURE:
<221> NAME/KEY: intron

```
<222> LOCATION: (4347)..(4509)
<220> FEATURE:
<221> NAME/KEY: exon
<222> LOCATION: (4510)..(4734)
<220> FEATURE:
<221> NAME/KEY: modified_base
<222> LOCATION: (1)..(4921)
<223> OTHER INFORMATION: n = g, a, c or t

<400> SEQUENCE: 2
gcatgcactg ccacaagtag tgaactcatg gttttacctc ctcaagtaga aaaccttttg      60
agtgaatttg aagatttatt ctcccaagaa ggacccattg ggcttcctcc tcttaggggg     120
atagaacatc aaattgactt tataccgggg gcaagcctac caaataggcc tccttataga     180
accaaccccg aggaaacaaa ggagatagaa tcacaagttc aagacttgtt ggagaagggt     240
tgggttcaaa agagcctaag cccttgtgct gtacctgtct tgttggtgcc aaaaaaagat     300
ggaaaatggc gtatgtgttg tgattgtaga gcaatcaaca acatcaccat caagtatagg     360
catccaatcc caaggcttga cgatatgctt gatgaattgc atgggtcaac tctattctcc     420
aaaattgacc ttaaaagtgg atatcaccaa attcgaatca aggagggtga tgagtggaaa     480
accgctttta agaccaaatt tggattatat gagtggttgg tgatgcccct tggtcttact     540
aacgctccaa gtacattcat gaggcttatg aatcacacct tgagggattg tataggtaaa     600
tatgtagtag tttattttga tgatatctta gtatatagta aaaccctaga agaccatcta     660
agtcaccttta gggaagttct tctagttctt aggaaaaata gtcttttttgc caatagggat     720
aagtgtacct tttgtgtaga tagcgtagtc ttttttaggct ttatagtaaa ccaaaagggg     780
gtgcatgtag atcccgagaa aatcaaagcc atccgcgagt ggccaactcc acaaaatgta     840
agtgatgtga aagttttca tgggttagct agcttctata aaggtttgt tcccaatttt     900
tctagcctag cttctccctt gaatgaactt gtaaaaaaag atgttgcatt ttgttggaat     960
gaaaagcatg agcaagcctt tcaaaggcta aagctcact caccaatgca cccatcctat    1020
ctcttccaaa tttttccaaa cttttggaga tagagtgtga tgcatcggga gtaggcatag    1080
tgcggttttg ttgcaaggtg gacaccccct gcttatttta gtgaaaaact ccatggtgcc    1140
accctcacta ccccacctat gacaaagact ctatgctctt gtgcgaccct aaagacttgg    1200
ggaacactac cttgngtccc aaagaatttg gntatccata gtgatcacga gtctttaaaa    1260
tatttaaagg gccaacacaa gctcaataag agacatgcta aatggatgga atttcttgaa    1320
caatttcctt atgtcatcaa atacaagaaa gggagcacca atatagtggc cgatgctctt    1380
tctagacggc acactctctt ttcaaaacta ggtgcccaaa ttcttggatt tgaccacata    1440
agagagcttt atcaagaaga tcaagaactc tcatccatct atgcccaatg tctacataga    1500
gcacaaggag gttactatgt gtccgaggga tatctttta aagaaggaaa actttgcatt    1560
ccccaaggaa cacatagaaa actccttgtc aaagaatcac atgaaggggg actcatgggc    1620
cattttggag ttgataaaac tctagacttt taaaagcaaa attttgttgg ccacacatga    1680
ggaaagatgt ccacgacatt gtctagagta tctcatgttt aaaagcaaag tctagaacaa    1740
tgccgctgga ctctacaccc ctttgccgat tgcaaagctc cttgtgaaga cattagcatg    1800
gatttcattt taggacttcc taggactgca agaggccatg actctatctt tgtggtagtg    1860
gaccgttta gcaaaatgtc tcactttatt ccatgccaca agtagatga tgctcaaaat    1920
atttctaaac tcttctttag agaagtggtg agactccatg gtctccctag aagtatagtg    1980
tccgatagag atcaccttaa atatataatt atacacttgt ttttttctc tttttattt    2040
```

| | |
|---|---|
| tatcaagtaa aaagtatttg ttctagatta ttatgagtat atacttactt tctgtatttc | 2100 |
| atttctttct attttttatg acgatgaaat ttcttattat atccagactt ttcatatata | 2160 |
| tttttatttc ttttccatct agatgctctg tactttcttt cagttgaaat ttccactctc | 2220 |
| caacaaaaca tcattcaagt tttgtataac actgtgacgt taaccagtta aaataagaaa | 2280 |
| atcatgtaat ataaattatt tcagtagata ttttagaatt acaaatacga taaataatta | 2340 |
| aatttaaaaa attattaaac aatgaatttt tttggaaatt aatataaaac ttagacttgt | 2400 |
| ggtttcttca ttcagtcaaa acctttttct attgtgtggc gtgtgcgtga acatcgaatt | 2460 |
| tgggtgcttt atgccgcttt atcttcatct gcaccttcaa attaataatt taattccgga | 2520 |
| aaataataaa cccacacact gttttatgca tatattaaga taaataaaag agaactattt | 2580 |
| taaagaatat aaaataataa atgtaacaaa tgatgtcact aaagaagaaa aaattaaca | 2640 |
| agaattgtaa tatatttctt tatgaaatgt tttgtgcatt accgagagag gtcgaacatg | 2700 |
| atacacgcaa gcatctaact agtttggtaa ttccttttca acatcgntaa gcacatcaca | 2760 |
| ctaaaattac tttaaataga taaattagat tcaattggat gacattaatt tataatactc | 2820 |
| tatccaaaat tataactata aataaaaagt tattttaga aaataagtaa tgaaaattta | 2880 |
| attctaaaat ttataacact tttatgctgt gtttgtttcg aagcatagaa aaataaaaag | 2940 |
| ttattgttgg gaatgaaaag tgaagaaaat catgtaataa aaacaaaatg acacgacaat | 3000 |
| caaaaaaaaa gttttcatgc aaaactttt tcaaaattta cacttttatg atgtgtttgt | 3060 |
| ttcgaagtgt agaaaaacga aagttatta ttggtaatga aagcgaaga aaatcacgta | 3120 |
| ataaaaacaa agcaagatgg cacgacaatc aaaaaaaagt ttctacacaa aactttattc | 3180 |
| aaaatttaca acactttat gttgttgttt gtttccgagg tatagaaaaa caagaatta | 3240 |
| gtgttggtaa tgaaagtga agaaaaccat gtaatgaaaa caaaatggca cgacaatcaa | 3300 |
| aaaaagtttt cacgcaaaat tttcttcaaa atttataaca ttttcatgtt gtgtttgttt | 3360 |
| caaagcctag aaaaacgaag agttactatt ggtaatgaaa agcgaagaaa accacataat | 3420 |
| aaaaacaaaa tggcacgaca atcaagaaaa agttttcaca caaaactttt ttcaaaattt | 3480 |
| actatgttta tttcgaaatt tagaaaaacg aagagttatt attagtaatg aaaagcgaag | 3540 |
| aaaactacgt aataaaaaac aaaatggcac gacaataaaa aaagttttca cgcaaaattt | 3600 |
| tcttggtgcg cagaaagtta tatatattaa ttaattaatt ttcatttact ttttcccctt | 3660 |
| tttatttaa agttaaatta ttattatttt catttaaaat ataaatatta tttaaatata | 3720 |
| aaaatataa ccttaatcaa aacaaagcct taatctaaaa tttacaacac ttttaacctt | 3780 |
| aaaattaact ttaaaggaa aatgatagtg tgacaactaa aaagttgta tacaaccctg | 3840 |
| tcataggttt agaaataaat atatataata aagagtaaat ttgtaattaa atgatataaa | 3900 |
| aaagtattaa aataataata tttagagtag taatatggtt gtataaaaaa atgtggttgt | 3960 |
| ccatatatca ttattcactt taaaatatca tgacaaatat tttcaccgaa agatggaaag | 4020 |
| aacgaaaaga gcgttggata atggaaaaat acaagcaatc tccctccagt actttgcata | 4080 |
| acattttgta ttagtgatga gttttttatc atatatattt agaatatagg aaaattttag | 4140 |
| aatcacgtgg atagctatat aatagtaata ttttaattta taatgtagtt gatttatttt | 4200 |
| gtcaactggt atacataaat atgtgttgat agtgggtgac ttgtggctta aagaaatgtc | 4260 |
| cagaggctga caacaactct gcacagacta gcgtaaac atg aag tcc aat ttt | 4313 |
|            Met Lys Ser Asn Phe       |      |
|            1               5         |      |
| gct att ttc gta gtc ttt tct ctt ctt ctt ctg gtacctcttc aatcttctct | 4366 |

```
Ala Ile Phe Val Val Phe Ser Leu Leu Leu Leu
            10                  15 acaaaaactc tgttgctctt tcacctctgt ttgtaatttt gtttacactt ttggaaaatt      4426
gaagctgata tatatgtaac aacctttcag ttttgtctgc actgaaactg atagaaaaat      4486
atacgttttg tggatatata tag gtt ggc agt tgc agc tgc gca aga aaa          4536
                          Val Gly Ser Cys Ser Cys Ala Arg Lys
                                       20                  25 gac atg aga ggg tat tgg aag gat atg atg aag gag caa cct atg cca        4584
Asp Met Arg Gly Tyr Trp Lys Asp Met Met Lys Glu Gln Pro Met Pro
             30                  35                  40 gaa gca atc aaa gac ctt att gag gat tca gaa gaa gtg tca gaa gca        4632
Glu Ala Ile Lys Asp Leu Ile Glu Asp Ser Glu Glu Val Ser Glu Ala
            45                  50                  55 ggg aag ggt cgt ttt gtt agg gac ttc gat gta aag cct aat gtc ata        4680
Gly Lys Gly Arg Phe Val Arg Asp Phe Asp Val Lys Pro Asn Val Ile
        60                  65                  70 tta tat cac aca cat gtt gtg ccc atg aag cag agg cag aag aat aaa        4728
Leu Tyr His Thr His Val Val Pro Met Lys Gln Arg Gln Lys Asn Lys
    75                  80                  85 gat tga agactatgtg attggcagtt tcagacttat ttggcaccaa atttatgatg         4784
Asp
 90 ctcttgttgc tgtttcaaaa tttgtactca aactttgaac cctttgcagc atcttgcttc      4844 tttttggtct tgctgaattt tgtcacagtt atactgtcac gaatagtttc tcttcataat      4904 aagcaacttt tcctctc                                                     4921

<210> SEQ ID NO 3
<211> LENGTH: 90
<212> TYPE: PRT
<213> ORGANISM: Phaseolus coccineus
<220> FEATURE:
<223> OTHER INFORMATION: Scarlet Runner Bean G654

<400> SEQUENCE: 3

Met Lys Ser Asn Phe Ala Ile Phe Val Val Phe Ser Leu Leu Leu Leu
 1               5                  10                  15

Val Gly Ser Cys Ser Cys Ala Arg Lys Asp Met Arg Gly Tyr Trp Lys
            20                  25                  30

Asp Met Met Lys Glu Gln Pro Met Pro Glu Ala Ile Lys Asp Leu Ile
        35                  40                  45

Glu Asp Ser Glu Glu Val Ser Glu Ala Gly Lys Gly Arg Phe Val Arg
    50                  55                  60

Asp Phe Asp Val Lys Pro Asn Val Ile Leu Tyr His Thr His Val Val
65                  70                  75                  80

Pro Met Lys Gln Arg Gln Lys Asn Lys Asp
            85                  90

<210> SEQ ID NO 4
<211> LENGTH: 6250
<212> TYPE: DNA
<213> ORGANISM: Arabidopsis thaliana
<220> FEATURE:
<223> OTHER INFORMATION: Arabidopsis G654 genomic region
<220> FEATURE:
<221> NAME/KEY: exon
<222> LOCATION: (5484)..(5540)
<220> FEATURE:
<221> NAME/KEY: intron
<222> LOCATION: (5541)..(5620)
<220> FEATURE:
```

-continued

```
<221> NAME/KEY: exon
<222> LOCATION: (5621)..(5812)

<400> SEQUENCE: 4
caaaacaaaa gcaaatgccg gttttcttat tattatttcg aactttagac cttttttgtaa      60
cgtttcttta atttttttcc ttgataaaga accctattat atcttagcta aatatttacc     120
tcattttgtt tatgagctaa accaccccaa aaatattgta gttttgcttt cggatttaac     180
tgccaagcaa gtgattagat atattaaagg aaaatgaatg aaaggacaaa aaaatataaa     240
cgacaatatt tgaatactga tatttatctc cattctcaaa tattttttgat ttattgtgac    300
aatatttggt tgtttcccat ttgctacatc tttgaggaca tgaaatgata acatatatat    360
gaacgagtat aatacattct cgtttcattt tacaaataat gtcaatttat gctaacattt    420
tttatttaaa aattatcctt ataagatttc agtgtattat tttaccatgg tactgtaaag    480
tcggatgcta tatatatata tatatatata tatatcaaaa atgacactga agaatttatt    540
tgaactaaaa ctaaaaacgt aaaataaaaa gaattttttca aaaatcaaaa attttatata   600
aaaatataga taaaatgtta atatagtaca acttctattc aaacagagag ataaatcttt   660
ctatagacag tgaatatcca ttataataac gagcaatagt tgtaatgttg cagtacaaaa   720
agagaattgt aatatttgtg catgattgag aaatctaagt tgactttgaa ttaaaaggct   780
aattccaaca agtacatgta gaagttgact atagctatat atttactaca aattgatcat   840
ttcaagaaag acatttaaat taagatatgc atgcatgact tgattgaacc ccactcgctt   900
gcttcgtgcc attcgacaag atgttacttt taaatgcaag gtaaattatg gatatactct   960
tctgtatttt ttgtagtaga tatttttacg aaaattgttt tttttccaaa atcaaatgat  1020
attattaat tttcaatata gaattaatta aattttaatt aattttgaag atttatatgc   1080
tgcagattag attaccattg gtgaaatcat gtttaggtaa ataataaatg atgttgtagt  1140
ttaggaaaaa aaaaaattct ttaatcttta tgtaagaatg ttaaacttca attataaaaa   1200
tatgaagcag tattatataa gatgtttaac taatcgaata atattttttg ggatgaaatt   1260
ttcttgcata tgtttctaaa aaaataatat gtgaaaaatt aacattcatt gtatgtttat   1320
aagaaatata tgtgagtttt gtttagataa ataatactta aaattaagaa tttgtaaagt   1380
tatactgcac ttcaaatatg ttatttttc cttttattta aaatatcagc aacattctaa    1440
atgattttat tttctttaaa aaattgaaaa aatgaaatta gcaaatatgt aaaatttaaa   1500
acgaatttaa gaaaaaactt tgtaaagata tgatatgctt tataaaaaaa acttggtggc   1560
gtacctacta aatatgatca cattagagat ttgtatcctt tagcatatag tatgtagtat   1620
agatatctat atttttattt attaaagagc atattcataa ataggtatt atatgttaat    1680
tacaataaac gttcaattcg ttatgttagt ttttagaaaa cttattgcgt gtgcatatca   1740
atgtgagaaa gcgactccac atgtgagatg ttggtctgag aaagctttct gcacttggtc   1800
ggaactactt catggactag aatgcaatcc atctattcaa agaaaagcag ttgtccatgc   1860
atgcctcggt ttttcacatt tggaagcagc gcaacaatgt cttacataat atgcgatcga   1920
tcactctgca accaatattc aagtacatag accatgacat caaaaacatt atcacaccga   1980
gaagaaagaa acgtcaattt ggtaacttaa tggcgttatg cctgcggtga attctcctaa   2040
gagttctccc aaattttatt gattccttgt ttttaacttt ttcgccaaag aatcatacat   2100
atagatttga caccatttca acttatcaaa tacaagtgaa taaataattt caagcttgaa   2160
aggaatttaa tcatgatcta aacctaaacg acaaattctt cacaagtgag aatcactaat   2220
```

```
tgactacccc ttggtcgcat atacatcatt gttgtaaatc tgaaaattgg tttggatttg   2280
atctgatatg tcattcatat aaaacttgta ttatttattt tagaattttg ccgcaaacag   2340
ataaatcatc atctatttag aaaattttca tttgcaccac aattaatcag gggaaaaggt   2400
gaaatcacat atcttatcta cactctttat taattaaacg ccataatata acaaattttc   2460
aaataccact tatgagaagc actaagatca ccttttctt tatgactttc tttctaaagc    2520
taagctggta gtcatgactc atgattatcc ttttcctaat gggaatattg tggaagcggt   2580
ttcaaatctt tagacaaaat tccatggcca ctaaaagtta gcaaagttaa aataagttta   2640
aaaaaatatg agtgtacttg gccatatgcc atattgttga gatcataaca agagaaataa   2700
tagtttattg aagtttagat cataatcaca atacatcatt gccttcatca acattttcca   2760
tggatttgag aggatcaact tcaatactaa tggtggggtc ttattcatcc attgctctct   2820
agccaattaa gcagttaggt tatttgtgta ctctagtagt tgccaaatca atcttaatat   2880
tcacaatgtt gtaatttcta attacgtata gataaatgac tagataacac gtggctttgg   2940
ttttatcagg aaagttttcc aaatcatata tatgaatgta gaatagtgtt cttcattaat   3000
tattaattag catctcacca tctgagactg ggagcatgtg acaagttgac atgtgtatta   3060
agagaacttt gagaaaacca cttttatgat actcccatct gagactggga tgagtaccat   3120
tttataaaaa tatgagtagt gaaaaaatat tcaaaaaaaa ttctaacatg tccttttaaaa  3180 cattttaacc ttataatttt aacaaacatc ttccaatatg cgttatgaaa actttataaa   3240
acttttttat aacatgcttt tgaaaatttt ataaatctgt atttttagaa acaaagtgat   3300 actttgaaa atagacaaat gaagtgctat tttttaaaat tgatatcata agtcttaact    3360
gtggtttgtt tgaattttat ttatatactt gtcaaaataa aactaaataa ataaattaaa   3420
ttattttata atcatgaaga taatattatc ataaagata aatataaaat caacaaattt     3480
atatttgtta ataaaaatac tttgagctct tcttcataag acttttccag cttccatcta   3540
gaaaatcaca taaattaaaa gataaataac cgaataaaca tagttcacat tctaactctt   3600
agtcttagat ttgttttaat tttcaaaggt ttaggtattg tatatgtttt ttttattggg   3660
ttgctagatt ttgatccaag aagaaatgac gggttgtagt atagatggtt tgtttgagtt   3720 ttttccccctt ggtttacttc gtttggtttt tgtccccaga attgttcttg tactcgctgg   3780
tttatgtctc tacaaagtcc acgaccattg ccggctcttt gtatttcaac ttgaattcta   3840
aattcgattg atgaaaaaaa aatgtatctc ttaaagtcca ttagtaccaa aaataactat   3900
atcattacta cataaaatag tcttgggttt tccaaagtat ttcgttgata tatgttaaga   3960
gttcgaaata gacacataga tataatgttg aaatgggacc tctcacataa ttatctcctt   4020
ttctcttcat ttctctacct ctcaagtttc caatcccacc ctaaggtaat ttatttctta   4080
acctaagtaa atttgttaac aaatcttaac tagctacaaa tgtgtattac aagtcttaaa   4140
taaaaaccta ctttaattca aaggtattaa accttcctaa attgatactt acttagtatc   4200
gatcggtcta gtttagggtt tggacaacac accatcatgg ggacgaaatt agtcattcta   4260
cggtgtccaa gacacaaatc tcggactcga tgtggatatg acacttcatt ataacttttta  4320 acttcataaa aactaactat taggaggaag aatcggaatc tgcatatcaa tcacaataga   4380
ctatagtata cttagatttt gatctaatca atgggctcct tcaactaata agtagcccac   4440
taccaataat gaaatcataa gacattatta aattaatcaa tgttctaaaa atactttggt   4500
tatgtgtccc gtagagctaa tgtgcacaca caatgaaagt tgacccgttt cacttgtccc   4560
acttttatga tcttttcttt taggttaaat ccaacttttta taatctcatc ttgttatcaa   4620
```

```
acaaaactttt tggcctgtct ttttcataat ttaaagtaac tctcacggag aaaagccaac    4680
attttcttct tgttttattc tttttaagaa aaatgaattc aaggggaccc caaatttaaa    4740
aggaaaacca aaactccttt ctatgtattt attacttgaa gttttctatg taatcaacaa    4800
tcctaacagt agagaataaa aaacatcgtt ttgggaggtt ttatattagc atatgagaat    4860
agttctaaaa ttgttttaca caaaaattag attttctttt cctctgtcaa tggagctata    4920
tcacttgtca ttttgcttaa ccctttgcgg gaagattgtt atgaaacagt tttaatggaa    4980
ttctagttgc caatgtcacg tttaatatgt tttgtcccta tactttattg aatcttataa    5040
tctttgttat agaattatct actttttagta ttttacatta acataatcta tagaattctt    5100
ctttgttcta tacaattaaa caagtaatat attcttaata catattaaaa atggtggtgt    5160
tgctatctga gctgtaatag ttgattgctc cagagaagaa tagacaaaaa tccttactta    5220
agaggcccac cactctgaaa atttagacaa gaaaaattaa acaaaattag gttacacata    5280
ttatcattta tatatatgca caacacaaag ttgaccttgc aatgtactat tgaataaaat    5340
aaataaatgc aagaagagag ggaattatca ctgttaccaa gaaaacaact tcctctaaac    5400
aggtctctat atatataaac tttaacacct aaagaattaa cacagatcaa gaaaaaatcc    5460
tcaaaacaaa agttaaagca gac atg aag caa cag caa cgt tac ttg gtc       5510
                        Met Lys Gln Gln Gln Arg Tyr Leu Val
                          1               5 gtc ttc atc gtc ctt tta agc ttt ctt ctg gtaaagcttc ttccttaatt       5560
Val Phe Ile Val Leu Leu Ser Phe Leu Leu
 10              15 atattaaaac cctaattaag atctcatata tctgaatgtt gtatatattt gttggtatag   5620 ttt gtg aat ctg agt gaa gga aga aca gga gga gtt gca gaa gaa tat     5668
Phe Val Asn Leu Ser Glu Gly Arg Thr Gly Gly Val Ala Glu Glu Tyr
 20              25                  30                  35 tgg aag aag atg atg aag aat gaa ccg ttg cct gaa cca atc aaa gag     5716
Trp Lys Lys Met Met Lys Asn Glu Pro Leu Pro Glu Pro Ile Lys Glu
             40                  45                  50 ctt ctc aac aat cct ttt agg acc gca caa gag aga ttc atc cag aat     5764
Leu Leu Asn Asn Pro Phe Arg Thr Ala Gln Glu Arg Phe Ile Gln Asn
         55                  60                  65 ttc gac acc aaa tct gtt gtc atc atc tac cac aat cct aat gaa taa    5812
Phe Asp Thr Lys Ser Val Val Ile Ile Tyr His Asn Pro Asn Glu
         70                  75                  80 tcaatgaagt ctctcatata gatatctatg actttaattt gtgtttatgt atggatcgac   5872
ttatacgtgc acgtatatgt tattaattaa gaaaagaaaa agctgcttga gttgttgtgt   5932
tatacacgta tactaaatat gttctgttta gtgcagaaat gttaacccta gctataaggg   5992 atttttttgtt cttttttttt tgttaccatt aatgtgagtg agtgagtttt gtgtgatgaa   6052
aattagattt gcttcacatt ttgttttgat atatataaat caatatactg tgcctttcgt   6112
gtcttgtttc ttatattatt ttgtgacatt aattaattat cttatcaaaa atttatttta   6172
ttaactgtgt cctatggaaa aagatgaaca atatgagtta acctcatctc aaggagattc   6232 tttttttgttt tgtttttc                                                 6250

<210> SEQ ID NO 5
<211> LENGTH: 82
<212> TYPE: PRT
<213> ORGANISM: Arabidopsis thaliana
<220> FEATURE:
<223> OTHER INFORMATION: Arabidopsis G654
```

```
<400> SEQUENCE: 5

Met Lys Gln Gln Gln Arg Tyr Leu Val Val Phe Ile Val Leu Leu Ser
 1               5                  10                  15

Phe Leu Leu Phe Val Asn Leu Ser Glu Gly Arg Thr Gly Gly Val Ala
             20                  25                  30

Glu Glu Tyr Trp Lys Lys Met Met Lys Asn Glu Pro Leu Pro Glu Pro
         35                  40                  45

Ile Lys Glu Leu Leu Asn Asn Pro Phe Arg Thr Ala Gln Glu Arg Phe
 50                  55                  60

Ile Gln Asn Phe Asp Thr Lys Ser Val Val Ile Ile Tyr His Asn Pro
 65                  70                  75                  80

Asn Glu

<210> SEQ ID NO 6
<211> LENGTH: 4846
<212> TYPE: DNA
<213> ORGANISM: Phaseolus coccineus
<220> FEATURE:
<223> OTHER INFORMATION: Scarlet Runner Bean C541 genomic region
<220> FEATURE:
<221> NAME/KEY: CDS
<222> LOCATION: (3154)..(3552)
<223> OTHER INFORMATION: Scarlet Runner Bean C541
<220> FEATURE:
<221> NAME/KEY: modified_base
<222> LOCATION: (1)..(4846)
<223> OTHER INFORMATION: n = g, a, c or t

<400> SEQUENCE: 6
aagctttaca aatgtccccc aaagatgaaa ccacgttatt attagtaaat cctgaaaagg      60
ttaacgcttc tgttcctcga attctaaacc atctgaaata tctagtggtt taaaatggag     120
acttgaggat atagtctcct gaaccagctg tcacggctga gttagataac attactgaat     180
ttctacggga gcggttgaaa tcactttcgc ccctttaaga agaagcctac accgggcacc     240
ttctttacgc aattcgaaat ttagtcttgc caggcagtcg ttggatcgaa ggtcttttc      300 gataccgagg aatctgactt tgcaaggaat aattcctaat cacaccaccc caaccctga      360 atacacttca ggaccctctg aaaccaactt cgtttcggct aaatcacaag aatctcccac     420
tcattccgat tttagccaat taaatatgat atcggtctgg gaagccgata aggaaattct     480
acaaaaagag tttatgaatg aggaaaataa ggaaagagaa gaactatttt ttaggtaccc     540
tgaaagagaa cgagaaaaat ttagaaaaaa atactactct catctgtaca ctgttcaaaa     600
gaatatccnn nnnaatggtt agataatata agaaaaggat aagtatgatt aaactgaaac     660
cacgtcggca gaaacaaagt gaattccccc ctttagagga agttcgtttc ttaaatatag     720
aaaacaaaga agtagtcgcc tcccttttta aaatgatctc agaaaacgaa gaagtaagta     780
taaaagatat tcaaaatcta cacagtcaac taaattttac taatcaaatg cttttttcaat     840 tagcaaataa aaaacaaaag aaaaaagmga aattgaaga aaaatcgtta ataaaaccat     900
ttaaattctc agaagaagag ataaaacagt taaaaattgg tcaaactttg gattctttat     960
acgatgaagt aaaacaaaag ttatctatct cggtaataaa agaaaaaccg aaatctaata    1020
atgatatgcc caaaggaca aatccaaatc aagaagtttt agcgaaatc gaaaagagat     1080 taaaacaaac tctgaacgac acaataaatg tgatagaaga aactaaaaac tcagactcat    1140
gttcagagtc tcccgatcgt attgaaaaaa taaacgtaa taatcagag atttccagta     1200 agccgaaatt tttacactcg ccccaccttc gatatcatcg agatggcgat ggacacctca    1260
```

-continued

```
gcattgatgg aatggatact gagtgatatg atggatgaca gatgatgaat atagaaaaac    1320
tcacgaaata acaatggccg ctacagcata tagagtaaaa cataccgagg aacaaacaat    1380
aaaattaatt atatctggat tcacgggagt attaaaaggc tggtgggata attacctcat    1440
gccagaacaa aagaattatg ttctaagctg tgtaaaaata gaaaacgaag aaggaatacc    1500
actaatggtg gaaacattgg tggtagcaat aattcataac tttataggag atccaaagat    1560
ttttgaagaa agaacatctt tattacttca taatctaaga tgtccaacct taggtgactt    1620
tagatggtat tcagaaaatt ttttagctat ggttttaaca agggaagatt gtagagaacc    1680
tttctggaaa gaacggttta tagctggatt accggatatc tttgctgaaa aggtaaaaga    1740
aaatttacaa aaggaatgcc caaacaccca attaaaagat gtaccatacg ggaaaataag    1800
ttcagttgta aaaaatacag gtcttcagtt atgcaataat atgaaaatag aaaataagat    1860 aaaaagagt gagagtcagg gcatcaagga attagggaa ttttgtactc aatacggtta    1920
tgaacgaaat acccctccat caaaaaataa aagaaaata gcaaaagaa aacagggag    1980 aaacaagcgc taaacaagc gctaaaccag cacgtaaaaa ttttagaaaa acggttaatt    2040
ttagaaaacc atgaaagtct aatgataagc ccactatagt ctgttataaa tgtggacgca    2100
taggacacat gaagcgagac tgtagactaa agaaaaaat tagtaatttg accataagtg    2160
atgaattaaa agaacaaatg gaaaaacttc tgataaattc ctccagaaga ggaagaaaca    2220
gaagaatcaa taggagattc tgattacgaa gtattggaca tgaggataac aattgtaatt    2280
gtgtctataa aataaatacg ataagtagtg aattaaaatt tgcgttagat tgcattgata    2340
aaattaataa tccggaggaa aagaccaaag ccttaataga catgaaaagg ctactcgttg    2400
aaaaagatga acccagttca tcttcacaaa aacctgaatt tataggatat gatttttaaag    2460 aaatattgag aaaagcgaaa acatcacata aagaaataac cattagcgat cttaatagtg    2520
aaataaataa attaaaagcc gaaatcgaat ctataaaagt cgagctacaa gaattaaaag    2580
ataaaattat acatgaggaa tccatctcct ctgccgacga aaattcacaa gaagaggaag    2640
ctagtagacc ttccatcaaa gaaataacat acaaaagaca aaagtggcat gtaaaaaatag    2700 ccctagaatt tgtttgttt gtgaccgttt cattgtggtc aaagatgagt ccttacctaa    2760
cacaataaaa aacgttactc ttaaatatca aggagagct acaaatatca atgaatgaat    2820
gacattaata tttttcttta gttttaaaac ttgaatgagt tgttttcata aatatctgac    2880
tgactgacat ttttattttt tctgaaaatg aggaaggttt attacgttaa caccatatat    2940
atatttttat ctcaaagtca acgaaatatt ataaagaat caattaaaaa aaattattct    3000
tttgcagaaa aaaaaattaa aaatatgaaa ctcctccaca ccatattacc atattataaa    3060
tataaaaaaa cctctcacaa atgtgcattc tggaattctt tatgttgaga gattaatctc    3120
taaagaaaaa aggttgagaa aggtgcagca aca atg tct cca ttc tgt aga aac    3174
                                    Met Ser Pro Phe Cys Arg Asn
                                      1               5 ttt tca atg gca tgg gtg ctt atg gca ttt gtg ttg ttt gca aac agt    3222
Phe Ser Met Ala Trp Val Leu Met Ala Phe Val Leu Phe Ala Asn Ser
       10                  15                  20 gct atg ccc aca aat gga tcc act gtt ggg gta aaa aac atg ttg ggt    3270
Ala Met Pro Thr Asn Gly Ser Thr Val Gly Val Lys Asn Met Leu Gly
   25                  30                  35 ggt aaa ttg atg cta aac gtt tta tgt ccc cat att gat aag caa cac    3318
Gly Lys Leu Met Leu Asn Val Leu Cys Pro His Ile Asp Lys Gln His
40                  45                  50                  55 att atc ccg aat ggt ggt tca ttt gag tgg aag tac aat ggt ggt gct    3366
```

-continued

| | | | | | | | | | | | | |
|---|---|---|---|---|---|---|---|---|---|---|---|---|
|Ile|Ile|Pro|Asn|Gly|Gly|Ser|Phe|Glu|Trp|Lys|Tyr|Asn|Gly|Gly|Ala|
| | | |60| | | |65| | | |70| |

```
cca cca ata gga caa tca cca ttc atg tgt ttc ttt cgg tgg aat aat    3414
Pro Pro Ile Gly Gln Ser Pro Phe Met Cys Phe Phe Arg Trp Asn Asn
            75                  80                  85 gtt cat cac tcc ctt gat ctg tgt tca cca agc aag tat act ggt tgt    3462
Val His His Ser Leu Asp Leu Cys Ser Pro Ser Lys Tyr Thr Gly Cys
        90                  95                  100 gaa aat gcc att tgg gaa atc aaa gaa aag caa ttt tgt agg tac aga    3510
Glu Asn Ala Ile Trp Glu Ile Lys Glu Lys Gln Phe Cys Arg Tyr Arg
    105                 110                 115 ggt gga cct att aat tat ttt tgc tat gac tgg gat gat tag           3552
Gly Gly Pro Ile Asn Tyr Phe Cys Tyr Asp Trp Asp Asp
120             125                 130 ttatatagat tattcatgtt tcatctcaat aaaaaaatga ctttagagtg attcttagtt  3612
tgcttaacat tcttacatat tcctaactat tccgtcacta ccacccgtaa ctatatttat  3672
ttaaaattag tatctgtcac agttttattt ttaaaaaagg ttatgtggat tagaagagag  3732
ataaatatgt agacggtcac caaccttaat ttttgaacta tgtaagacta tattgaccaa  3792
gaatatatgt ttaaactcat tcatttaaag actatatctc catttatgat tatgcaaatg  3852
caattagttt ttttttttcat tgaagaattc aaaagaaagt tatcattaaa agtatcatt  3912
aaatcactta tatgttgttt cttaatatcc ttattgttaa tagaataatt ttttttatcc  3972
tttaattaag gttattacta cttttttttc atatcttcat tattttgaaa tatttttaaa  4032
atttatcaat ttttgtaaca ccccagaaaa tacatgtaac tatcactttt tttttatatt  4092
acaaatttat gacttataga aatacaaata ttaaaaatat aaggttcaaa actacatcct  4152
aaagtctttc agaccctctg acacatgtat catctgctcg tatatgtgat acagtcatcg  4212
cagttcacaa gataacaaga aaaccaaggg taagctaatg aaaaaaaatt ccataacata  4272
tttaattcat gcaaaagaa ccagtcaaag taatcattta taaacatttc tttaaatatt  4332
gttatataaa atttcaatat caatttcatc attcatatag accacacatg gatctatttt  4392
caatcacaat cattggattt catttaatc ctacttcgnc ttccagaaga ctcattaagt  4452
atgcccctac cagagactaa cacctaatca agagaaatg atcaaggtaa gttcaaacat  4512
ccaataacga gtgcctacag tgggacccaa tgtgtatgaa ctccttatca gcttctcacc  4572
acctgatatc ttattctata tgacgtagat catcagtgaa actagaggat ctccgttaaa  4632
catatgtttt ttatacttaa tgtcatcaaa caacaactca cacattatcc caaatgtatg  4692
acatcaattt catacaattt tcatcattca tatataatac atatcattga atcacataac  4752
atttaaaaat tcataccatt caagaacttt tccaacatca aaagcaatat ttactttcaa  4812
actatcaaaa tataattatt atttaataaa gctt                              4846
```

<210> SEQ ID NO 7
<211> LENGTH: 132
<212> TYPE: PRT
<213> ORGANISM: Phaseolus coccineus
<220> FEATURE:
<223> OTHER INFORMATION: Scarlet Runner Bean C541

<400> SEQUENCE: 7

| | | | | | | | | | | | | | | |
|---|---|---|---|---|---|---|---|---|---|---|---|---|---|---|
|Met|Ser|Pro|Phe|Cys|Arg|Asn|Phe|Ser|Met|Ala|Trp|Val|Leu|Met|Ala|
|1| | | |5| | | | |10| | | | |15| |

| | | | | | | | | | | | | | | |
|---|---|---|---|---|---|---|---|---|---|---|---|---|---|---|
|Phe|Val|Leu|Phe|Ala|Asn|Ser|Ala|Met|Pro|Thr|Asn|Gly|Ser|Thr|Val|
| | | | |20| | | | |25| | | | |30| |

```
Gly Val Lys Asn Met Leu Gly Gly Lys Leu Met Leu Asn Val Leu Cys
         35                  40                  45

Pro His Ile Asp Lys Gln His Ile Ile Pro Asn Gly Gly Ser Phe Glu
     50                  55                  60

Trp Lys Tyr Asn Gly Gly Ala Pro Pro Ile Gly Gln Ser Pro Phe Met
 65                  70                  75                  80

Cys Phe Phe Arg Trp Asn Asn Val His His Ser Leu Asp Leu Cys Ser
                 85                  90                  95

Pro Ser Lys Tyr Thr Gly Cys Glu Asn Ala Ile Trp Glu Ile Lys Glu
             100                 105                 110

Lys Gln Phe Cys Arg Tyr Arg Gly Gly Pro Ile Asn Tyr Phe Cys Tyr
         115                 120                 125

Asp Trp Asp Asp
         130

<210> SEQ ID NO 8
<211> LENGTH: 2601
<212> TYPE: DNA
<213> ORGANISM: Arabidopsis thaliana
<220> FEATURE:
<223> OTHER INFORMATION: Arabidopsis C541 genomic region
<220> FEATURE:
<221> NAME/KEY: CDS
<222> LOCATION: (1693)..(2178)
<223> OTHER INFORMATION: Arabidopsis C541

<400> SEQUENCE: 8
ttatcttatt tccatataat tgttgtttta ctttcaaaat ttttaatttt ttatatttat      60 cttttacag tttaaaatta ataaaatgaa acttttttc ttaaatgtgt taaaatataa     120
aatcaaaaaa gttgttatat ggtacatggc acaatccttaa aaattattaa tttgaaaacg    180
atactttata taataaaatt atcttagttg acatttttat tagtgttttc aatcatattt    240
ttgtttgctt gataagcgta aaacaaatca aacttaacga tactttatat aataaaatta    300
tcttagttga cattttttatt agtgtcttca atcatatctt tgtttgcttg ataagcgtaa    360
aacaaatcaa gtaaagttgg gcacctcaat tgttttaaaa aagtttgggt acctcaaaaa    420
ttaataggtc ttgtcagatt cttacaaaaa aaatctggaa gaatttatga agaaggggg    480 gggagggggg gaggggggggg aagtgaagat gaatattcaa caaagagggg taggcatgat    540
gttaagtgag ttaaaaaact atgttaatgg agacaatttt ctgttaacaa acccgttaat    600
tgaaaacgat agcattcttc tctaacaatg taaaacgata ttgtttttatc ataactactc    660 attaaatttc tgagtttcaa atcatataaa gatttagggg ggtgtattca attaaggatt    720
tgaaatgatt tgtattaaaa tgacaaatcc catgttatttt caaacatgaa ttgtaaaaac    780 tttttttaaaa tcaagtgtta ttagattagt gattttaaaaa tgtacaacca aacccactgt    840
tattggaaac attttaagta gtggatttaa aatgacttga gtgatttttgg gtgggattgc    900 agaaaattc ttagttaaga attcaaacat ccaaatctca tggtttcaag tagaatttgg    960
gagaatttta ataacaaatc tcctaattta ccaaaagtca ccaaaatcat ttaaaaactc   1020
attaaaattt aaatgatttc aaatctccag ttgaatacat cccctttggaa ttagagattt   1080 tgctcgattt gggacctaag attgaatttt gggggatttag tttaatcgtt acaacaaaat   1140
gacatcgtat tattgttata ggaaacaatg tcgttttcag ttgacatgta tgttaataga   1200
aaattaactc tattaacggg atttgctaac ccatttaaca tcgtaactaa atggtcaagt   1260
caataaaagt ttggtattta tttgaaaagt caacgtaagt ttgatattta tttgaaaagt   1320
```

```
caacataaat ttgatatctt atttcgtttc gacagacata aggatttaca tcaatgtttt      1380
taataaatta aagattatta tgacattttt tccatttaaa attgccaatg ttttcgaaac      1440
caagatactc aaaattgaca tacctaattc aatctacatt tgtttgacag caattcacgt      1500
gccttgacca catggcacat actggcaata catcaatttt aaggaaaagg tagattcgga      1560
tacaatataa tggaaataag tggaaaggat cattgactac ttgacttgta acaaacaaca      1620
cacagtatat aactcattcg acatttacaa acaacattgt gctagcttaa actccctctc      1680
```

```
ctattcaaaa aa atg gat att cca aag caa tat cta tca cta ttc ata ttg      1731
              Met Asp Ile Pro Lys Gln Tyr Leu Ser Leu Phe Ile Leu
              1               5                   10 att atc ttc ata act aca aaa tta tca caa gcc gac cat aaa aac gac        1779
Ile Ile Phe Ile Thr Thr Lys Leu Ser Gln Ala Asp His Lys Asn Asp
    15                  20                  25 att cca gtt ccc aac gat cca tca tca aca aat tct gtg ttt cct acc        1827
Ile Pro Val Pro Asn Asp Pro Ser Ser Thr Asn Ser Val Phe Pro Thr
30              35                  40                  45 tcg aaa aga acc gtg gaa atc aat aat gat ctc ggt aat cag cta acg        1875
Ser Lys Arg Thr Val Glu Ile Asn Asn Asp Leu Gly Asn Gln Leu Thr
                50                  55                  60 tta ctg tat cat tgt aaa tca aaa gac gat gat tta ggt aac cgg act        1923
Leu Leu Tyr His Cys Lys Ser Lys Asp Asp Asp Leu Gly Asn Arg Thr
            65                  70                  75 ctg caa cca ggt gag tcg tgg tct ttt agt ttc ggg cgt caa ttc ttt        1971
Leu Gln Pro Gly Glu Ser Trp Ser Phe Ser Phe Gly Arg Gln Phe Phe
        80                  85                  90 gga agg acg ttg tat ttt tgt agt ttt agt tgg cca aat gaa tcg cat        2019
Gly Arg Thr Leu Tyr Phe Cys Ser Phe Ser Trp Pro Asn Glu Ser His
    95                  100                 105 tcg ttc gat ata tat aaa gac cat cga gat agc ggc ggt gat aac aag        2067
Ser Phe Asp Ile Tyr Lys Asp His Arg Asp Ser Gly Gly Asp Asn Lys
110                 115                 120                 125 tgc gag agc gac agg tgt gtg tgg aag ata aga aga aac gga cct tgt        2115
Cys Glu Ser Asp Arg Cys Val Trp Lys Ile Arg Arg Asn Gly Pro Cys
                130                 135                 140 agg ttt aac gat gaa acg aag cag ttt gat ctt tgt tat cct tgg aat        2163
Arg Phe Asn Asp Glu Thr Lys Gln Phe Asp Leu Cys Tyr Pro Trp Asn
            145                 150                 155 aaa tct ttg tat tga caacaatatg ctgatgttct gtcttttacg actcatggag        2218
Lys Ser Leu Tyr
            160
```

```
tttcattgtt tgaaacaata atataaaaca tataaaattt ctattattcc aagttccaac      2278
ttataataat ttgataatca tatcatatta tcatcttaag cattcaatgc tacaaagata      2338
atacccccaa gctattttac attaaaagct gaaacagaga cacaatacta acgataaaag      2398
ttcgtagtat ctttatgcaa ccatacatac atatacacaa agatagacag gtagtgtcct      2458
aataattcta cttgggtgag gtatgaacag cagcaacagt agataccatt gtatccatac      2518
cacacatatt atgaggccct ctgcagattt tgtagtaacc atgctctccc cacatcgctc      2578
cccacgagtt cttgataatc caa                                              2601
```

<210> SEQ ID NO 9
<211> LENGTH: 161
<212> TYPE: PRT
<213> ORGANISM: Arabidopsis thaliana
<220> FEATURE:
<223> OTHER INFORMATION: Arabidopsis C541

<400> SEQUENCE: 9

```
Met Asp Ile Pro Lys Gln Tyr Leu Ser Leu Phe Ile Leu Ile Phe
 1               5                  10                 15

Ile Thr Thr Lys Leu Ser Gln Ala Asp His Lys Asn Asp Ile Pro Val
            20                  25                  30

Pro Asn Asp Pro Ser Ser Thr Asn Ser Val Phe Pro Thr Ser Lys Arg
            35                  40                  45

Thr Val Glu Ile Asn Asn Asp Leu Gly Asn Gln Leu Thr Leu Leu Tyr
        50                  55                  60

His Cys Lys Ser Lys Asp Asp Leu Gly Asn Arg Thr Leu Gln Pro
65              70                  75                  80

Gly Glu Ser Trp Ser Phe Ser Phe Gly Arg Gln Phe Gly Arg Thr
                85                  90                  95

Leu Tyr Phe Cys Ser Phe Ser Trp Pro Asn Glu Ser His Ser Phe Asp
            100                 105                 110

Ile Tyr Lys Asp His Arg Asp Ser Gly Gly Asp Asn Lys Cys Glu Ser
            115                 120                 125

Asp Arg Cys Val Trp Lys Ile Arg Arg Asn Gly Pro Cys Arg Phe Asn
130                 135                 140

Asp Glu Thr Lys Gln Phe Asp Leu Cys Tyr Pro Trp Asn Lys Ser Leu
145                 150                 155                 160

Tyr

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence:promoter
      control region homologous repeat of Scarlet
      Runner Bean G564 and C541 promoter region

<400> SEQUENCE: 10
gaaaagcgaa                                                          10

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence:promoter
      control element homologous repeat of Scarlet
      Runner Bean G564 promoter region

<400> SEQUENCE: 11
gaaaagtgaa                                                          10

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence:promoter
      control element of Arabidopsis G564 ortholog
      promoter region

<400> SEQUENCE: 12
gaaaagccaa                                                          10

<210> SEQ ID NO 13
<211> LENGTH: 450
<212> TYPE: DNA
```

<213> ORGANISM: Phaseolus coccineus
<220> FEATURE:
<223> OTHER INFORMATION: Scarlet Runner Bean G564 promoter (-921 to
      -662) PLACE database Signal Scan search sequence

<400> SEQUENCE: 13

```
tgaaaagtga agaaaaccat gtaatgaaaa caaaatggca cgacaatcaa aaaaagttttt     60
cacgcaaaat tttcttcaaa atttataaca ttttcatgtt gtgtttgttt caaagcctag    120
aaaaacgaag agttactatt ggtaatgaaa agcgaagaaa accacataat aaaaacaaaa    180
tggcacgaca atcaagaaaa agttttcaca caaaactttt ttcaaaattt actatgttta    240
tttcgaaatt tagaaaaacg aagagttatt attagtaatg aaaagcgaag aaaactacgt    300
aataaaaaac aaaatggcac gacaataaaa aagttttca cgcaaaattt tcttggtgcg     360
cagaaagtta tatatattaa ttaattaatt ttcatttact ttttttccctt tttattttaa   420
agttaaatta ttattatttt catttaaaat                                      450
```

<210> SEQ ID NO 14
<211> LENGTH: 448
<212> TYPE: DNA
<213> ORGANISM: Phaseolus coccineus
<220> FEATURE:
<223> OTHER INFORMATION: Scarlet Runner Bean G564 promoter (-921 to
      -662) PlantCARE database Signal Scan search sequence

<400> SEQUENCE: 14

```
gaaaagtgaa gaaaaccatg taatgaaaac aaaatggcac gacaatcaaa aaaagttttc     60
acgcaaaatt ttcttcaaaa tttataacat tttcatgttg tgtttgtttc aaagcctaga   120
aaaacgaaga gttactattg gtaatgaaaa gcgaagaaaa ccacataata aaacaaaat    180
ggcacgacaa tcaagaaaaa gttttcacac aaaacttttt tcaaaattta ctatgtttat   240
ttcgaaattt agaaaaacga agagttatta ttagtaatga aaagcgaaga aaactacgta   300
ataaaaaaca aaatggcacg acaataaaaa agttttcacg caaaatttt cttggtgcgc    360
agaaagttat atatattaat taattaattt tcatttactt ttttcccttt ttattttaaa   420
gttaaattat tattatttc atttaaaa                                        448
```

<210> SEQ ID NO 15
<211> LENGTH: 10
<212> TYPE: DNA
<213> ORGANISM: Artificial Sequence
<220> FEATURE:
<223> OTHER INFORMATION: Description of Artificial Sequence:site
      #S000067 MARTBOX signal sequence promoter control element

<400> SEQUENCE: 15

```
ttwtwttwtt                                                            10
```

<210> SEQ ID NO 16
<211> LENGTH: 10
<212> TYPE: DNA
<213> ORGANISM: Artificial Sequence
<220> FEATURE:
<223> OTHER INFORMATION: Description of Artificial Sequence:3-AF1
      binding site promoter control element

<400> SEQUENCE: 16

```
aagagttatt                                                            10
```

<210> SEQ ID NO 17
<211> LENGTH: 10

```
<212> TYPE: DNA
<213> ORGANISM: Artificial Sequence
<220> FEATURE:
<223> OTHER INFORMATION: Description of Artificial Sequence:Hordeum
      vulgare ABRE and Petroselinum crispum ACE promoter control element

<400> SEQUENCE: 17
actacgtaat                                                              10

<210> SEQ ID NO 18
<211> LENGTH: 12
<212> TYPE: DNA
<213> ORGANISM: Artificial Sequence
<220> FEATURE:
<223> OTHER INFORMATION: Description of Artificial Sequence:Solanum
      tuberosum AT1-motif promoter control element

<400> SEQUENCE: 18
ttttatttta aa                                                           12

<210> SEQ ID NO 19
<211> LENGTH: 10
<212> TYPE: DNA
<213> ORGANISM: Artificial Sequence
<220> FEATURE:
<223> OTHER INFORMATION: Description of Artificial Sequence:TC-rich
      repeat promoter control element

<400> SEQUENCE: 19
gttttcttca                                                              10

<210> SEQ ID NO 20
<211> LENGTH: 10
<212> TYPE: DNA
<213> ORGANISM: Artificial Sequence
<220> FEATURE:
<223> OTHER INFORMATION: Description of Artificial Sequence:TC-rich
      repeat promoter control element

<400> SEQUENCE: 20
attttcttca                                                              10

<210> SEQ ID NO 21
<211> LENGTH: 10
<212> TYPE: DNA
<213> ORGANISM: Artificial Sequence
<220> FEATURE:
<223> OTHER INFORMATION: Description of Artificial Sequence:TC-rich
      repeat promoter control element

<400> SEQUENCE: 21
gttttcttcg                                                              10

<210> SEQ ID NO 22
<211> LENGTH: 10
<212> TYPE: DNA
<213> ORGANISM: Artificial Sequence
<220> FEATURE:
<223> OTHER INFORMATION: Description of Artificial Sequence:TC-rich
      repeat promoter control element

<400> SEQUENCE: 22
ttttcttga                                                               10

<210> SEQ ID NO 23
<211> LENGTH: 10
<212> TYPE: DNA
```

```
<213> ORGANISM: Artificial Sequence
<220> FEATURE:
<223> OTHER INFORMATION: Description of Artificial Sequence:TC-rich
      repeat promoter control element

<400> SEQUENCE: 23
tttttctaaa                                                            10

<210> SEQ ID NO 24
<211> LENGTH: 10
<212> TYPE: DNA
<213> ORGANISM: Artificial Sequence
<220> FEATURE:
<223> OTHER INFORMATION: Description of Artificial Sequence:TC-rich
      repeat promoter control element

<400> SEQUENCE: 24
attttcttgg                                                            10

<210> SEQ ID NO 25
<211> LENGTH: 50
<212> TYPE: DNA
<213> ORGANISM: Artificial Sequence
<220> FEATURE:
<223> OTHER INFORMATION: Description of Artificial Sequence:
      oligonucleotide linker-primer

<400> SEQUENCE: 25
gagagagaga gagagagaga actagtctcg agttttttttt tttttttttt               50

<210> SEQ ID NO 26
<211> LENGTH: 16
<212> TYPE: DNA
<213> ORGANISM: Artificial Sequence
<220> FEATURE:
<223> OTHER INFORMATION: Description of Artificial Sequence:
      anchor/reverse primer G primer

<400> SEQUENCE: 26
aagctttttt tttttg                                                     16

<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence:
      anchor/reverse primer C primer

<400> SEQUENCE: 27
aagctttttt tttttc                                                     16

<210> SEQ ID NO 28
<211> LENGTH: 13
<212> TYPE: DNA
<213> ORGANISM: Artificial Sequence
<220> FEATURE:
<223> OTHER INFORMATION: Description of Artificial Sequence:H-AP49
      forward primer

<400> SEQUENCE: 28
aagctttagt cca                                                        13

<210> SEQ ID NO 29
<211> LENGTH: 13
<212> TYPE: DNA
<213> ORGANISM: Artificial Sequence
```

```
<220> FEATURE:
<223> OTHER INFORMATION: Description of Artificial Sequence:H-AP50
      forward primer

<400> SEQUENCE: 29
aagctttgag act                                                             13

<210> SEQ ID NO 30
<211> LENGTH: 13
<212> TYPE: DNA
<213> ORGANISM: Artificial Sequence
<220> FEATURE:
<223> OTHER INFORMATION: Description of Artificial Sequence:H-AP51
      forward primer

<400> SEQUENCE: 30
aagcttcgaa atg                                                             13

<210> SEQ ID NO 31
<211> LENGTH: 13
<212> TYPE: DNA
<213> ORGANISM: Artificial Sequence
<220> FEATURE:
<223> OTHER INFORMATION: Description of Artificial Sequence:H-AP52
      forward primer

<400> SEQUENCE: 31
aagcttgacc ttt                                                             13

<210> SEQ ID NO 32
<211> LENGTH: 13
<212> TYPE: DNA
<213> ORGANISM: Artificial Sequence
<220> FEATURE:
<223> OTHER INFORMATION: Description of Artificial Sequence:H-AP53
      forward primer

<400> SEQUENCE: 32
aagcttcctc tat                                                             13

<210> SEQ ID NO 33
<211> LENGTH: 13
<212> TYPE: DNA
<213> ORGANISM: Artificial Sequence
<220> FEATURE:
<223> OTHER INFORMATION: Description of Artificial Sequence:H-AP54
      forward primer

<400> SEQUENCE: 33
aagcttttga ggt                                                             13

<210> SEQ ID NO 34
<211> LENGTH: 13
<212> TYPE: DNA
<213> ORGANISM: Artificial Sequence
<220> FEATURE:
<223> OTHER INFORMATION: Description of Artificial Sequence:H-AP55
      forward primer

<400> SEQUENCE: 34
aagcttacgt tag                                                             13

<210> SEQ ID NO 35
<211> LENGTH: 13
<212> TYPE: DNA
<213> ORGANISM: Artificial Sequence
<220> FEATURE:
```

```
<223> OTHER INFORMATION: Description of Artificial Sequence:H-AP56
      forward primer

<400> SEQUENCE: 35
aagcttatga agg                                                          13

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence:oligo(dT-20)
      primer

<400> SEQUENCE: 36
tttttttttt tttttttttt                                                   20

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence:dT-20dN
      primer
<220> FEATURE:
<221> NAME/KEY: modified_base
<222> LOCATION: (21)
<223> OTHER INFORMATION: n = g, c, a or t

<400> SEQUENCE: 37
tttttttttt tttttttttt n                                                 21

<210> SEQ ID NO 38
<211> LENGTH: 34
<212> TYPE: DNA
<213> ORGANISM: Artificial Sequence
<220> FEATURE:
<223> OTHER INFORMATION: Description of Artificial Sequence:mutagenic
      oligo

<400> SEQUENCE: 38
attggactgc atgcttacgc tagtctgtgc agag                                   34
```